(12) United States Patent
Crimaldi et al.

(10) Patent No.: US 11,559,430 B2
(45) Date of Patent: *Jan. 24, 2023

(54) GLAUCOMA STENT AND METHODS THEREOF FOR GLAUCOMA TREATMENT

(71) Applicant: Glaukos Corporation, San Clemente, CA (US)

(72) Inventors: Douglas Daniel Crimaldi, San Marcos, CA (US); Charles Raymond Kalina, Jr., Irvine, CA (US)

(73) Assignee: Glaukos Corporation, Aliso Viejo, CA (US)

( * ) Notice: Subject to any disclaimer, the term of this patent is extended or adjusted under 35 U.S.C. 154(b) by 522 days.

This patent is subject to a terminal disclaimer.

(21) Appl. No.: 16/717,957

(22) Filed: Dec. 17, 2019

(65) Prior Publication Data

US 2020/0179171 A1    Jun. 11, 2020

Related U.S. Application Data

(63) Continuation of application No. 14/207,240, filed on Mar. 12, 2014, now Pat. No. 10,517,759.

(60) Provisional application No. 61/794,832, filed on Mar. 15, 2013.

(51) Int. Cl.
   *A61F 9/007* (2006.01)

(52) U.S. Cl.
   CPC .................. *A61F 9/00781* (2013.01)

(58) Field of Classification Search
   CPC ................... A61F 9/00781; A61F 9/00772
   See application file for complete search history.

(56) References Cited

U.S. PATENT DOCUMENTS

| 2,031,754 A | 2/1936 | Mills |
| 2,127,903 A | 8/1938 | Bowen |
| 3,159,161 A | 12/1964 | Ness |
| 3,416,530 A | 12/1968 | Ness |
| 3,710,795 A | 1/1973 | Higuchi et al. |

(Continued)

FOREIGN PATENT DOCUMENTS

| AU | 199876197 | 2/1999 |
| AU | 200072059 A1 | 7/2001 |

(Continued)

OTHER PUBLICATIONS

Johnson et al., "Schlemm's Canal Becomes Smaller After Successful Filtration Surgery", (reprinted) ARCM Ophthalmol/vol. 118, Sep. 2000 (www.archophthalmol.com) p. 1251-1256.

(Continued)

*Primary Examiner* — Benjamin J Klein
(74) *Attorney, Agent, or Firm* — Knobbe Martens Olson & Bear LLP

(57) ABSTRACT

The invention relates generally to medical devices and methods for reducing the intraocular pressure in an animal eye and, more particularly, to stent type devices for permitting aqueous outflow from the eye's anterior chamber and associated methods thereof for the treatment of glaucoma. Some aspects provide a self-trephining glaucoma stent and methods thereof which advantageously allow for a "one-step" procedure in which the incision and placement of the stent are accomplished by a single device and operation. This desirably allows for a faster, safer, and less expensive surgical procedure.

17 Claims, 37 Drawing Sheets

(56) References Cited

U.S. PATENT DOCUMENTS

| | | |
|---|---|---|
| 3,717,151 A | 2/1973 | Collett |
| 3,788,327 A | 1/1974 | Donowitz et al. |
| 3,827,700 A | 8/1974 | Kaller |
| 3,863,623 A | 2/1975 | Trueblood et al. |
| 3,915,172 A | 10/1975 | Krejci et al. |
| 3,948,271 A | 4/1976 | Akiyama |
| 3,948,871 A | 4/1976 | Butterfield et al. |
| 3,961,628 A | 6/1976 | Arnold |
| 4,030,480 A | 6/1977 | Meyer |
| 4,037,604 A | 7/1977 | Newkirk |
| 4,043,346 A | 8/1977 | Mobley et al. |
| 4,093,708 A | 6/1978 | Zaffaroni et al. |
| 4,113,088 A | 9/1978 | Binkhorst |
| 4,168,697 A | 9/1979 | Cantekin |
| 4,175,563 A | 11/1979 | Arenberg et al. |
| 4,402,681 A | 9/1983 | Haas et al. |
| 4,428,746 A | 1/1984 | Mendez |
| 4,449,974 A | 5/1984 | Messingschlager |
| 4,450,150 A | 5/1984 | Sidman |
| 4,457,757 A | 7/1984 | Molteno |
| 4,468,216 A | 8/1984 | Muto |
| 4,501,274 A | 2/1985 | Skjaerpe |
| 4,554,918 A | 11/1985 | White |
| 4,604,087 A | 8/1986 | Joseph |
| 4,632,842 A | 12/1986 | Karwoski et al. |
| 4,634,418 A | 1/1987 | Binder |
| 4,692,142 A | 9/1987 | Dignam et al. |
| 4,718,907 A | 1/1988 | Karwoski et al. |
| 4,722,724 A | 2/1988 | Schocket |
| 4,733,665 A | 3/1988 | Palmaz |
| 4,743,248 A | 5/1988 | Bartoo et al. |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,828,439 A | 5/1989 | Giannuzi |
| 4,846,172 A | 7/1989 | Berlin |
| 4,853,224 A | 8/1989 | Wong |
| 4,886,488 A | 12/1989 | White |
| 4,936,825 A | 6/1990 | Ungerleider |
| 4,946,436 A | 8/1990 | Smith |
| 4,955,881 A | 9/1990 | Eckenhoff |
| 4,968,296 A | 11/1990 | Ritch et al. |
| 4,986,810 A | 1/1991 | Semrad |
| 4,997,652 A | 3/1991 | Wong |
| 5,005,577 A | 4/1991 | Frenekl |
| 5,017,381 A | 5/1991 | Maruyama et al. |
| 5,041,081 A | 8/1991 | Odrich |
| 5,073,163 A | 12/1991 | Lippman |
| 5,092,837 A | 3/1992 | Ritch et al. |
| 5,116,327 A | 5/1992 | Seder et al. |
| 5,127,901 A | 7/1992 | Odrich |
| 5,128,145 A | 7/1992 | Edgren et al. |
| 5,139,502 A | 8/1992 | Berg et al. |
| 5,164,188 A | 11/1992 | Wong |
| 5,171,213 A | 12/1992 | Price, Jr. |
| 5,178,604 A | 1/1993 | Baerveldt et al. |
| 5,180,362 A | 1/1993 | Worst |
| 5,207,685 A | 5/1993 | Cinberg et al. |
| 5,246,451 A | 9/1993 | Trescony et al. |
| 5,248,231 A | 9/1993 | Denham et al. |
| 5,300,020 A | 4/1994 | L'Esperance, Jr. |
| 5,318,513 A | 6/1994 | Leib et al. |
| 5,326,345 A | 7/1994 | Price, Jr. |
| 5,334,137 A | 8/1994 | Freeman |
| 5,338,291 A | 8/1994 | Speckman et al. |
| 5,342,370 A | 8/1994 | Simon et al. |
| 5,346,464 A | 9/1994 | Camras |
| 5,358,492 A | 10/1994 | Feibus |
| 5,360,399 A | 11/1994 | Stegmann |
| 5,370,607 A | 12/1994 | Memmen |
| 5,370,641 A | 12/1994 | O'Donnell, Jr. |
| 5,372,577 A | 12/1994 | Ungerleider |
| 5,378,474 A | 1/1995 | Morella et al. |
| 5,378,475 A | 1/1995 | Smith et al. |
| 5,380,290 A | 1/1995 | Makower et al. |
| 5,397,300 A | 3/1995 | Baerveldt et al. |
| 5,433,701 A | 7/1995 | Rubinstein |
| 5,443,505 A | 8/1995 | Wong et al. |
| 5,454,796 A | 10/1995 | Krupin |
| 5,476,445 A | 12/1995 | Baerveldt et al. |
| 5,486,165 A | 1/1996 | Stegmann |
| 5,520,631 A | 5/1996 | Nordquist et al. |
| 5,558,629 A | 9/1996 | Baerveldt et al. |
| 5,558,630 A | 9/1996 | Fisher |
| 5,562,641 A | 10/1996 | Flomenblit et al. |
| RE35,390 E | 12/1996 | Smith |
| 5,626,558 A | 5/1997 | Suson |
| 5,626,559 A | 5/1997 | Solomon |
| 5,629,008 A | 5/1997 | Lee |
| 5,639,278 A | 6/1997 | Dereume et al. |
| 5,643,321 A | 7/1997 | McDevitt |
| 5,651,782 A | 7/1997 | Simon et al. |
| 5,676,679 A | 10/1997 | Simon et al. |
| 5,681,275 A | 10/1997 | Ahmed |
| 5,702,414 A | 12/1997 | Richter et al. |
| 5,702,419 A | 12/1997 | Berry et al. |
| 5,704,907 A | 1/1998 | Nordquist et al. |
| 5,713,844 A | 2/1998 | Peyman |
| 5,722,948 A | 3/1998 | Gross |
| 5,723,005 A | 3/1998 | Herrick |
| 5,725,529 A | 3/1998 | Nicholson et al. |
| 5,741,333 A | 4/1998 | Frid |
| 5,743,868 A | 4/1998 | Brown et al. |
| 5,752,928 A | 5/1998 | de Roulhac et al. |
| 5,762,625 A | 6/1998 | Igaki |
| 5,766,242 A | 6/1998 | Wong et al. |
| 5,766,243 A | 6/1998 | Christensen et al. |
| 5,773,019 A | 6/1998 | Ashton et al. |
| 5,785,674 A | 7/1998 | Mateen |
| 5,800,376 A | 9/1998 | Vaskelis |
| 5,807,302 A | 9/1998 | Wandel |
| 5,810,870 A | 9/1998 | Myers et al. |
| 5,824,071 A | 10/1998 | Nelson et al. |
| 5,824,072 A | 10/1998 | Wong |
| 5,830,171 A | 11/1998 | Wallace |
| 5,865,831 A | 2/1999 | Cozean et al. |
| 5,868,697 A | 2/1999 | Richter et al. |
| 5,869,079 A | 2/1999 | Wong et al. |
| 5,879,319 A | 3/1999 | Pynson et al. |
| 5,882,327 A | 3/1999 | Jacob |
| 5,902,598 A | 5/1999 | Chen et al. |
| 5,908,449 A | 6/1999 | Bruchman et al. |
| 5,913,852 A | 6/1999 | Magram |
| 5,932,299 A | 8/1999 | Katoot |
| 5,980,548 A | 11/1999 | Evans |
| 6,007,510 A | 12/1999 | Nigam |
| 6,007,511 A | 12/1999 | Prywes |
| 6,033,434 A | 3/2000 | Borghi |
| 6,050,970 A | 4/2000 | Baeverldt |
| 6,077,299 A | 6/2000 | Adelberg et al. |
| 6,102,045 A | 8/2000 | Nordquist et al. |
| 6,142,990 A | 11/2000 | Burk |
| 6,146,387 A | 11/2000 | Trott et al. |
| 6,165,210 A | 12/2000 | Lau et al. |
| 6,168,575 B1 | 1/2001 | Soltanpour |
| 6,174,305 B1 | 1/2001 | Mikus et al. |
| 6,186,974 B1 | 2/2001 | Allan et al. |
| 6,196,993 B1 | 3/2001 | Cohan et al. |
| 6,203,513 B1 | 3/2001 | Yaron et al. |
| 6,231,597 B1 | 5/2001 | Deem et al. |
| 6,241,721 B1 | 6/2001 | Cozean et al. |
| 6,261,256 B1 | 7/2001 | Ahmed |
| 6,290,684 B1 | 9/2001 | Herrick |
| 6,306,114 B1 | 10/2001 | Freeman et al. |
| 6,328,758 B1 | 12/2001 | Tornier et al. |
| 6,331,313 B1 | 12/2001 | Wong et al. |
| 6,358,222 B1 | 3/2002 | Grundei |
| 6,363,938 B2 | 4/2002 | Saadat et al. |
| 6,375,642 B1 | 4/2002 | Grieshaber et al. |
| 6,375,972 B1 | 4/2002 | Guo et al. |
| 6,423,001 B1 | 7/2002 | Abreu |
| 6,443,893 B1 | 9/2002 | Schnakenberg et al. |

(56) References Cited

U.S. PATENT DOCUMENTS

| | | |
|---|---|---|
| 6,450,984 B1 | 9/2002 | Lynch et al. |
| 6,464,724 B1 | 10/2002 | Lynch et al. |
| 6,468,283 B1 | 10/2002 | Richter et al. |
| 6,494,857 B1 | 12/2002 | Neuhann |
| 6,508,779 B1 | 1/2003 | Suson |
| 6,517,483 B2 | 2/2003 | Park et al. |
| 6,524,275 B1 | 2/2003 | Lynch et al. |
| 6,533,768 B1 | 3/2003 | Hill |
| 6,544,249 B1 | 4/2003 | Yu et al. |
| 6,582,453 B1 | 6/2003 | Tran et al. |
| 6,585,753 B2 | 7/2003 | Eder et al. |
| 6,589,198 B1 | 7/2003 | Soltanpour et al. |
| 6,589,203 B1 | 7/2003 | Mitrev |
| 6,595,945 B2 | 7/2003 | Brown |
| 6,605,053 B1 | 8/2003 | Kamm et al. |
| 6,623,283 B1 | 9/2003 | Torigian et al. |
| 6,626,858 B2 | 9/2003 | Lynch et al. |
| 6,638,239 B1 | 10/2003 | Bergheim et al. |
| 6,666,213 B2 | 12/2003 | Svadovskiy |
| 6,666,841 B2 | 12/2003 | Gharib et al. |
| 6,682,500 B2 | 1/2004 | Soltanpour et al. |
| 6,699,211 B2 | 3/2004 | Savage |
| 6,712,764 B2 | 3/2004 | Jeffries et al. |
| 6,726,666 B2 | 4/2004 | de Juan, Jr. |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,764,698 B1 | 7/2004 | Byun et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,893,413 B2 | 5/2005 | Martin |
| 6,939,298 B2 | 9/2005 | Brown et al. |
| 6,939,299 B1 | 9/2005 | Petersen et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,981,958 B1 | 1/2006 | Gharib et al. |
| 6,998,137 B2 | 2/2006 | Shih et al. |
| 7,094,225 B2 | 8/2006 | Tu et al. |
| 7,101,402 B2 | 9/2006 | Phelps et al. |
| 7,101,567 B1 | 9/2006 | Sano et al. |
| 7,135,009 B2 | 11/2006 | Tu et al. |
| 7,144,616 B1 | 12/2006 | Unger et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,192,484 B2 | 3/2007 | Chappa et al. |
| 7,220,238 B2 | 5/2007 | Lynch et al. |
| 7,252,006 B2 | 8/2007 | Tai et al. |
| 7,273,475 B2 | 9/2007 | Tu et al. |
| 7,294,115 B1 | 11/2007 | Wilk |
| 7,297,130 B2 | 11/2007 | Bergheim et al. |
| 7,331,984 B2 | 2/2008 | Tu et al. |
| 7,364,564 B2 | 4/2008 | Sniegowski et al. |
| 7,431,710 B2 | 10/2008 | Tu et al. |
| 7,445,793 B2 | 11/2008 | Niwa et al. |
| 7,488,303 B1 | 2/2009 | Haffner et al. |
| RE40,722 E | 6/2009 | Chappa |
| 7,563,241 B2 | 7/2009 | Tu et al. |
| 7,641,627 B2 | 1/2010 | Camras et al. |
| 7,678,065 B2 | 3/2010 | Haffner et al. |
| 7,695,135 B1 | 4/2010 | Rosenthal |
| 7,708,711 B2 | 5/2010 | Tu et al. |
| 7,776,024 B2 | 8/2010 | Santini et al. |
| 7,811,268 B2 | 10/2010 | Maldon Ado Bas |
| 7,815,592 B2 | 10/2010 | Coroneo |
| 7,850,637 B2 | 12/2010 | Lynch et al. |
| 7,857,782 B2 | 12/2010 | Tu et al. |
| 7,862,531 B2 | 1/2011 | Yaron et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,951,155 B2 | 5/2011 | Smedley et al. |
| 7,997,460 B2 | 8/2011 | Badawi et al. |
| 8,007,459 B2 | 8/2011 | Haffner et al. |
| D645,489 S | 9/2011 | Gille et al. |
| D645,490 S | 9/2011 | Gille et al. |
| 8,034,016 B2 | 10/2011 | Yaron et al. |
| 8,034,105 B2 | 10/2011 | Stegmann et al. |
| 8,062,244 B2 | 11/2011 | Tu et al. |
| 8,070,290 B2 | 12/2011 | Gille et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,267,882 B2 | 9/2012 | Euteneuer et al. |
| 8,267,995 B2 | 9/2012 | Castillejos |
| 8,273,050 B2 | 9/2012 | Bergheim et al. |
| 8,333,742 B2 | 12/2012 | Bergheim et al. |
| 8,337,445 B2 | 12/2012 | Tu et al. |
| 8,348,877 B2 | 1/2013 | Tu et al. |
| 8,388,568 B2 | 3/2013 | Lynch et al. |
| 8,404,269 B2 | 3/2013 | Snyder et al. |
| 8,414,518 B2 | 4/2013 | Schieber et al. |
| 8,419,673 B2 | 4/2013 | Rickard |
| 8,425,449 B2 | 4/2013 | Wardle et al. |
| 8,439,972 B2 | 5/2013 | Badawi et al. |
| 8,444,589 B2 | 5/2013 | Silvestrini |
| 8,454,582 B2 | 6/2013 | Dejuan et al. |
| 8,475,374 B2 | 7/2013 | Irazoqui et al. |
| 8,506,515 B2 | 8/2013 | Burns et al. |
| 8,545,431 B2 | 10/2013 | Rickard |
| 8,579,846 B2 | 11/2013 | Tu et al. |
| 8,579,848 B2 | 11/2013 | Field et al. |
| 8,585,631 B2 | 11/2013 | Dacquay |
| 8,585,664 B2 | 11/2013 | Dos Santos et al. |
| 8,603,024 B2 | 12/2013 | Bohm et al. |
| 8,617,094 B2 | 12/2013 | Smedley et al. |
| 8,656,958 B2 | 2/2014 | Unger et al. |
| 8,657,776 B2 | 2/2014 | Wardle et al. |
| 8,721,580 B2 | 5/2014 | Rickard et al. |
| 8,753,305 B2 | 6/2014 | Field et al. |
| 8,771,217 B2 | 7/2014 | Lynch et al. |
| 8,771,220 B2 | 7/2014 | Nissan |
| 8,801,648 B2 | 8/2014 | Bergheim et al. |
| 8,808,219 B2 | 8/2014 | Bergheim et al. |
| 8,808,222 B2 | 8/2014 | Schieber et al. |
| 8,808,224 B2 | 8/2014 | Rickard |
| 8,814,820 B2 | 8/2014 | Bergheim et al. |
| 8,840,578 B2 | 9/2014 | Dos Santos et al. |
| 8,864,701 B2 | 10/2014 | Dos Santos et al. |
| 8,882,781 B2 | 11/2014 | Smedley et al. |
| 8,956,320 B2 | 2/2015 | Ovchinnikov et al. |
| 8,986,240 B2 | 3/2015 | Dos Santos et al. |
| 8,998,838 B2 | 4/2015 | Yalamanchili |
| 9,022,967 B2 | 5/2015 | Oliver et al. |
| 9,066,782 B2 | 6/2015 | Tu et al. |
| 9,072,588 B2 | 7/2015 | Bohm et al. |
| 9,125,721 B2 | 9/2015 | Field |
| 9,132,034 B2 | 9/2015 | Dos Santos |
| 9,155,653 B2 | 10/2015 | Field |
| 9,155,654 B2 | 10/2015 | Tu et al. |
| 9,173,775 B2 | 11/2015 | Haffner et al. |
| 9,220,632 B2 | 12/2015 | Smedley et al. |
| 9,226,851 B2 | 1/2016 | Gunn |
| 9,283,115 B2 | 3/2016 | Lind et al. |
| 9,289,324 B2 | 3/2016 | Johnson et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,603,741 B2 | 3/2017 | Berlin |
| 9,636,255 B2 | 5/2017 | Haffner et al. |
| 9,668,915 B2 | 6/2017 | Haffner et al. |
| 9,730,638 B2 | 8/2017 | Haffner et al. |
| 9,789,001 B2 | 10/2017 | Tu et al. |

(56) References Cited

U.S. PATENT DOCUMENTS

| | | | |
|---|---|---|---|
| 9,827,143 | B2 | 11/2017 | Lynch |
| 9,833,357 | B2 | 12/2017 | Berlin |
| 9,962,290 | B2 | 5/2018 | Burns et al. |
| 9,987,472 | B2 | 6/2018 | Tu et al. |
| 9,993,368 | B2 | 6/2018 | Bergheim et al. |
| D833,008 | S | 11/2018 | Kalina, Jr. et al. |
| 10,159,601 | B2 | 12/2018 | Berlin |
| 10,183,551 | B2 | 1/2019 | Rangel-Friedman et al. |
| 10,206,813 | B2 | 2/2019 | Haffner et al. |
| D846,738 | S | 4/2019 | Kalina, Jr. et al. |
| 10,245,178 | B1 | 4/2019 | Heitzmann et al. |
| 10,271,989 | B2 | 4/2019 | Haffner et al. |
| 10,285,853 | B2 | 5/2019 | Rangel-Friedman et al. |
| 10,285,856 | B2 | 5/2019 | Tu et al. |
| 10,406,029 | B2 | 9/2019 | Tu et al. |
| 10,485,701 | B2 | 11/2019 | Haffner et al. |
| 10,485,702 | B2 | 11/2019 | Bergheim et al. |
| 10,492,950 | B2 | 12/2019 | Lynch et al. |
| 10,499,809 | B2 | 12/2019 | Kalina, Jr. et al. |
| 10,517,759 | B2 * | 12/2019 | Grimaldi ............. A61F 9/00781 |
| 10,568,762 | B2 | 2/2020 | Lynch et al. |
| D886,997 | S | 6/2020 | Kalina, Jr. et al. |
| 10,674,906 | B2 | 6/2020 | Kalina, Jr. et al. |
| 10,813,789 | B2 | 10/2020 | Haffner et al. |
| D901,683 | S | 11/2020 | Kalina, Jr. et al. |
| 10,828,195 | B2 | 11/2020 | Burns et al. |
| 10,828,473 | B2 | 11/2020 | Haffner et al. |
| 10,959,941 | B2 | 3/2021 | Haffner |
| 11,019,996 | B2 | 6/2021 | Kalina, Jr. et al. |
| 11,019,997 | B2 | 6/2021 | Kalina, Jr. et al. |
| 11,116,625 | B2 | 9/2021 | Kalina, Jr. |
| D938,585 | S | 12/2021 | Kalina, Jr. et al. |
| 11,197,780 | B2 | 12/2021 | Haffner et al. |
| 11,253,394 | B2 | 2/2022 | Haffner et al. |
| 11,426,306 | B2 | 3/2022 | Haffner et al. |
| 11,318,043 | B2 | 5/2022 | Heitzrnann et al. |
| 11,376,040 | B2 | 7/2022 | Kalina, Jr. et al. |
| 2001/0000527 | A1 | 4/2001 | Yaron et al. |
| 2001/0053873 | A1 | 12/2001 | Schaaf et al. |
| 2002/0013546 | A1 | 1/2002 | Grieshaber et al. |
| 2002/0013572 | A1 | 1/2002 | Berlin |
| 2002/0026200 | A1 | 2/2002 | Savage |
| 2002/0052640 | A1 | 5/2002 | Bigus et al. |
| 2002/0082591 | A1 | 6/2002 | Haefliger |
| 2002/0087111 | A1 | 7/2002 | Ethier et al. |
| 2002/0099434 | A1 | 7/2002 | Buscemi et al. |
| 2002/0102307 | A1 | 8/2002 | Guo et al. |
| 2002/0133168 | A1 | 9/2002 | Smedley et al. |
| 2002/0143284 | A1 | 10/2002 | Tu et al. |
| 2002/0156413 | A1 | 10/2002 | Williams et al. |
| 2002/0169468 | A1 | 11/2002 | Brown |
| 2002/0177856 | A1 | 11/2002 | Richter et al. |
| 2002/0188308 | A1 | 12/2002 | Tu et al. |
| 2002/0193725 | A1 | 12/2002 | Odrich |
| 2003/0019833 | A1 | 1/2003 | Unger et al. |
| 2003/0055372 | A1 | 3/2003 | Lynch et al. |
| 2003/0060752 | A1 | 3/2003 | Bergheim et al. |
| 2003/0079329 | A1 | 5/2003 | Yaron et al. |
| 2003/0083646 | A1 | 5/2003 | Sirhan et al. |
| 2003/0088260 | A1 | 5/2003 | Smedley et al. |
| 2003/0097151 | A1 | 5/2003 | Smedley et al. |
| 2003/0135149 | A1 | 7/2003 | Cullen et al. |
| 2003/0139729 | A1 | 7/2003 | Stegmann et al. |
| 2003/0153863 | A1 | 8/2003 | Patel |
| 2003/0176854 | A1 | 9/2003 | Rodstrom |
| 2003/0181848 | A1 | 9/2003 | Bergheim et al. |
| 2003/0187384 | A1 | 10/2003 | Bergheim et al. |
| 2003/0208163 | A1 | 11/2003 | Yaron et al. |
| 2003/0212383 | A1 | 11/2003 | Cote et al. |
| 2003/0229303 | A1 | 12/2003 | Haffner et al. |
| 2003/0236483 | A1 | 12/2003 | Ren |
| 2003/0236484 | A1 | 12/2003 | Lynch et al. |
| 2004/0024345 | A1 | 2/2004 | Gharib et al. |
| 2004/0059248 | A1 | 3/2004 | Messner et al. |
| 2004/0076676 | A1 | 4/2004 | Tojo et al. |
| 2004/0076868 | A1 | 4/2004 | Tojo et al. |
| 2004/0088048 | A1 | 5/2004 | Richter et al. |
| 2004/0092856 | A1 | 5/2004 | Dahan |
| 2004/0102729 | A1 | 5/2004 | Haffner et al. |
| 2004/0111050 | A1 | 6/2004 | Smedley et al. |
| 2004/0111080 | A1 | 6/2004 | Harper et al. |
| 2004/0115268 | A1 | 6/2004 | Ashton et al. |
| 2004/0127843 | A1 | 7/2004 | Tu et al. |
| 2004/0147870 | A1 | 7/2004 | Burns et al. |
| 2004/0154946 | A1 | 8/2004 | Solovay et al. |
| 2004/0162545 | A1 | 8/2004 | Brown et al. |
| 2004/0176341 | A1 | 9/2004 | Chou et al. |
| 2004/0180075 | A1 | 9/2004 | Robinson et al. |
| 2004/0193095 | A1 | 9/2004 | Shadduck |
| 2004/0193262 | A1 | 9/2004 | Shadduck |
| 2004/0210181 | A1 | 10/2004 | Vass et al. |
| 2004/0210185 | A1 | 10/2004 | Tu et al. |
| 2004/0215126 | A1 | 10/2004 | Ahmed |
| 2004/0216749 | A1 | 11/2004 | Tu |
| 2004/0225250 | A1 | 11/2004 | Yablonski |
| 2004/0254519 | A1 | 12/2004 | Tu et al. |
| 2004/0254520 | A1 | 12/2004 | Porteous et al. |
| 2004/0254521 | A1 | 12/2004 | Simon |
| 2004/0260227 | A1 | 12/2004 | Lisk, Jr. et al. |
| 2004/0260228 | A1 | 12/2004 | Lynch et al. |
| 2005/0008673 | A1 | 1/2005 | Snyder et al. |
| 2005/0038498 | A1 | 2/2005 | Dubrow et al. |
| 2005/0049578 | A1 | 3/2005 | Tu et al. |
| 2005/0055075 | A1 | 3/2005 | Pinchuk et al. |
| 2005/0107734 | A1 | 5/2005 | Coroneo |
| 2005/0119601 | A9 | 6/2005 | Lynch et al. |
| 2005/0119737 | A1 | 6/2005 | Bene et al. |
| 2005/0125003 | A1 | 6/2005 | Pinchuk et al. |
| 2005/0137538 | A1 | 6/2005 | Kunzler et al. |
| 2005/0159660 | A1 | 7/2005 | Montegrande et al. |
| 2005/0171507 | A1 | 8/2005 | Christian et al. |
| 2005/0175708 | A1 | 8/2005 | Carrasquillo et al. |
| 2005/0182350 | A1 | 8/2005 | Nigam |
| 2005/0184004 | A1 | 8/2005 | Rodgers et al. |
| 2005/0186279 | A1 | 8/2005 | Guo et al. |
| 2005/0192527 | A1 | 9/2005 | Gharib et al. |
| 2005/0209549 | A1 | 9/2005 | Bergheim et al. |
| 2005/0232972 | A1 | 10/2005 | Odrich |
| 2005/0240143 | A1 | 10/2005 | Dohlman |
| 2005/0244461 | A1 | 11/2005 | Nivaggioli et al. |
| 2005/0244467 | A1 | 11/2005 | Nivaggioli et al. |
| 2005/0244477 | A1 | 11/2005 | Hughes et al. |
| 2005/0250788 | A1 | 11/2005 | Tu et al. |
| 2005/0261624 | A1 | 11/2005 | Wilcox |
| 2005/0267397 | A1 | 12/2005 | Bhalla |
| 2005/0267398 | A1 | 12/2005 | Protopsaltis et al. |
| 2005/0273033 | A1 | 12/2005 | Grahn et al. |
| 2005/0276841 | A1 | 12/2005 | Davis et al. |
| 2005/0277864 | A1 | 12/2005 | Haffner et al. |
| 2005/0281861 | A1 | 12/2005 | Hughes et al. |
| 2005/0288619 | A1 | 12/2005 | Savage |
| 2006/0009498 | A1 | 1/2006 | Whitcup |
| 2006/0020253 | A1 | 1/2006 | Prescott |
| 2006/0032507 | A1 | 2/2006 | Tu |
| 2006/0036207 | A1 | 2/2006 | Koonmen et al. |
| 2006/0067978 | A1 | 3/2006 | Heiler et al. |
| 2006/0069340 | A1 | 3/2006 | Simon |
| 2006/0074375 | A1 | 4/2006 | Bergheim et al. |
| 2006/0079828 | A1 | 4/2006 | Brown |
| 2006/0083772 | A1 | 4/2006 | DeWitt et al. |
| 2006/0084907 | A1 | 4/2006 | Bergheim et al. |
| 2006/0116626 | A1 | 6/2006 | Smedley et al. |
| 2006/0129129 | A1 | 6/2006 | Smith |
| 2006/0155300 | A1 | 7/2006 | Stamper et al. |
| 2006/0173397 | A1 | 8/2006 | Tu et al. |
| 2006/0195055 | A1 | 8/2006 | Bergheim et al. |
| 2006/0195056 | A1 | 8/2006 | Bergheim et al. |
| 2006/0200113 | A1 | 9/2006 | Haffner et al. |
| 2006/0210604 | A1 | 9/2006 | Dadey et al. |
| 2006/0235367 | A1 | 10/2006 | Takashima et al. |
| 2006/0241749 | A1 | 10/2006 | Tu et al. |
| 2006/0246112 | A1 | 11/2006 | Snyder et al. |
| 2006/0257450 | A1 | 11/2006 | Mudumba et al. |
| 2006/0257451 | A1 | 11/2006 | Varner et al. |

(56) References Cited

U.S. PATENT DOCUMENTS

| | | |
|---|---|---|
| 2006/0276738 A1 | 12/2006 | Becker |
| 2006/0276739 A1 | 12/2006 | Brown |
| 2006/0292222 A1 | 12/2006 | Jonasse |
| 2007/0004998 A1 | 1/2007 | Rodgers et al. |
| 2007/0031472 A1 | 2/2007 | Huang et al. |
| 2007/0032734 A1 | 2/2007 | Najafi et al. |
| 2007/0059336 A1 | 3/2007 | Hughes et al. |
| 2007/0073390 A1 | 3/2007 | Lee |
| 2007/0078371 A1 | 4/2007 | Brown et al. |
| 2007/0088014 A1 | 4/2007 | Edelman et al. |
| 2007/0088432 A1 | 4/2007 | Solovay et al. |
| 2007/0093740 A1 | 4/2007 | Shetty |
| 2007/0106199 A1 | 5/2007 | Krivoy et al. |
| 2007/0106200 A1 | 5/2007 | Levy |
| 2007/0112263 A1 | 5/2007 | Fink et al. |
| 2007/0118065 A1 | 5/2007 | Pinchuk et al. |
| 2007/0118066 A1 | 5/2007 | Pinchuk et al. |
| 2007/0123767 A1 | 5/2007 | Montegrande et al. |
| 2007/0123812 A1 | 5/2007 | Pinchuk et al. |
| 2007/0129623 A1 | 6/2007 | Fleischman et al. |
| 2007/0154621 A1 | 7/2007 | Raad |
| 2007/0156079 A1 | 7/2007 | Brown |
| 2007/0179426 A1 | 8/2007 | Selden |
| 2007/0185468 A1 | 8/2007 | Prywes |
| 2007/0191863 A1 | 8/2007 | De Juan, Jr. et al. |
| 2007/0207186 A1 | 9/2007 | Scanlon et al. |
| 2007/0212386 A1 | 9/2007 | Patravale et al. |
| 2007/0212387 A1 | 9/2007 | Patravale et al. |
| 2007/0212388 A1 | 9/2007 | Patravale et al. |
| 2007/0212393 A1 | 9/2007 | Patravale et al. |
| 2007/0212395 A1 | 9/2007 | Donello et al. |
| 2007/0219632 A1 | 9/2007 | Castillejos |
| 2007/0233037 A1 | 10/2007 | Gifford, III et al. |
| 2007/0260201 A1 | 11/2007 | Prausnitz et al. |
| 2007/0276315 A1 | 11/2007 | Haffner |
| 2007/0276316 A1 | 11/2007 | Haffner |
| 2007/0282244 A1 | 12/2007 | Tu et al. |
| 2007/0282245 A1 | 12/2007 | Tu et al. |
| 2007/0292470 A1 | 12/2007 | Thornton |
| 2007/0292474 A1 | 12/2007 | Hsu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2007/0298073 A1 | 12/2007 | Whitcup et al. |
| 2007/0298074 A1 | 12/2007 | Robinson et al. |
| 2008/0027304 A1 | 1/2008 | Pardo et al. |
| 2008/0038316 A1 | 2/2008 | Wong et al. |
| 2008/0039931 A1 | 2/2008 | Jelle et al. |
| 2008/0045878 A1 | 2/2008 | Bergheim et al. |
| 2008/0057101 A1 | 3/2008 | Roorda |
| 2008/0057102 A1 | 3/2008 | Roorda |
| 2008/0057103 A1 | 3/2008 | Roorda |
| 2008/0058704 A1 | 3/2008 | Hee et al. |
| 2008/0081064 A1 | 4/2008 | Jelle et al. |
| 2008/0082078 A1 | 4/2008 | Berlin |
| 2008/0107694 A1 | 5/2008 | Trogden et al. |
| 2008/0108932 A1 | 5/2008 | Rodgers |
| 2008/0108934 A1 | 5/2008 | Berlin |
| 2008/0112923 A1 | 5/2008 | Hughes et al. |
| 2008/0125691 A1 | 5/2008 | Yaron et al. |
| 2008/0131484 A1 | 6/2008 | Robinson et al. |
| 2008/0147021 A1 | 6/2008 | Jani |
| 2008/0147168 A1 | 6/2008 | Ransbury et al. |
| 2008/0152694 A1 | 6/2008 | Lobl et al. |
| 2008/0161741 A1 | 7/2008 | Bene et al. |
| 2008/0161907 A1 | 7/2008 | Chen et al. |
| 2008/0177153 A1 | 7/2008 | Bachman et al. |
| 2008/0200860 A1 | 8/2008 | Tu et al. |
| 2008/0210322 A1 | 9/2008 | Unger et al. |
| 2008/0221501 A1 | 9/2008 | Cote et al. |
| 2008/0228127 A1 | 9/2008 | Burns et al. |
| 2008/0236669 A1 | 10/2008 | Unger et al. |
| 2008/0243243 A1 | 10/2008 | Williams et al. |
| 2008/0243247 A1 | 10/2008 | Poley et al. |
| 2008/0277007 A1 | 11/2008 | Unger et al. |
| 2008/0289710 A1 | 11/2008 | Unger et al. |
| 2008/0292679 A1 | 11/2008 | Lyons et al. |
| 2008/0306429 A1 | 12/2008 | Shields et al. |
| 2009/0036768 A1 | 2/2009 | Seehusen et al. |
| 2009/0036818 A1 | 2/2009 | Grahn et al. |
| 2009/0043321 A1 | 2/2009 | Conston et al. |
| 2009/0069648 A1 | 3/2009 | Irazoqui et al. |
| 2009/0076436 A2 | 3/2009 | Gharib et al. |
| 2009/0082321 A1 | 3/2009 | Edelman et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0104248 A1 | 4/2009 | Rapacki et al. |
| 2009/0118702 A1 | 5/2009 | Lazar |
| 2009/0123515 A1 | 5/2009 | Taylor et al. |
| 2009/0132040 A1 | 5/2009 | Frion et al. |
| 2009/0137992 A1 | 5/2009 | Mallakrishnan |
| 2009/0138081 A1 | 5/2009 | Bergheim et al. |
| 2009/0148498 A1 | 6/2009 | Libin et al. |
| 2009/0149947 A1 | 6/2009 | Frohwitter |
| 2009/0151422 A1 | 6/2009 | Unger et al. |
| 2009/0155338 A1 | 6/2009 | Conway et al. |
| 2009/0177138 A1 | 7/2009 | Brown et al. |
| 2009/0204053 A1 | 8/2009 | Nissan et al. |
| 2009/0214619 A1 | 8/2009 | Reiff et al. |
| 2009/0220572 A1 | 9/2009 | Deschatelets et al. |
| 2009/0227933 A1 | 9/2009 | Karageozian |
| 2009/0227934 A1 | 9/2009 | Eutenever et al. |
| 2009/0264861 A1 | 10/2009 | Jain et al. |
| 2009/0275924 A1 | 11/2009 | Lattanzio et al. |
| 2009/0280158 A1 | 11/2009 | Butuner |
| 2009/0287136 A1 | 11/2009 | Castillejos |
| 2009/0326432 A1 | 12/2009 | Schmidt et al. |
| 2010/0004635 A1 | 1/2010 | Lin et al. |
| 2010/0015195 A1 | 1/2010 | Jain et al. |
| 2010/0025613 A1 | 2/2010 | Tai et al. |
| 2010/0042209 A1 | 2/2010 | Guarnieri |
| 2010/0056977 A1 | 3/2010 | Wandel |
| 2010/0056979 A1 | 3/2010 | Smedley et al. |
| 2010/0057055 A1 | 3/2010 | Camras et al. |
| 2010/0087774 A1 | 4/2010 | Haffner et al. |
| 2010/0106073 A1 | 4/2010 | Haffner et al. |
| 2010/0114006 A1 | 5/2010 | Baerveldt |
| 2010/0121342 A1 | 5/2010 | Schieber et al. |
| 2010/0125237 A1 | 5/2010 | Schocket |
| 2010/0145180 A1 | 6/2010 | Abreu |
| 2010/0158980 A1 | 6/2010 | Kopczynski et al. |
| 2010/0168644 A1 | 7/2010 | Brown |
| 2010/0175767 A1 | 7/2010 | Unger et al. |
| 2010/0185138 A1 | 7/2010 | Yaron et al. |
| 2010/0191103 A1 | 7/2010 | Stamper et al. |
| 2010/0191329 A1 | 7/2010 | Badawi et al. |
| 2010/0222733 A1 | 9/2010 | Schieber et al. |
| 2010/0225061 A1 | 9/2010 | Bath |
| 2010/0234791 A1 | 9/2010 | Lynch et al. |
| 2010/0241046 A1 | 9/2010 | Pinchuk et al. |
| 2010/0249691 A1 | 9/2010 | Van der Mooren et al. |
| 2010/0255061 A1 | 10/2010 | de Juan, Jr. et al. |
| 2010/0274259 A1 | 10/2010 | Yaron et al. |
| 2010/0278898 A1 | 11/2010 | Hughes et al. |
| 2011/0009874 A1 | 1/2011 | Wardle et al. |
| 2011/0009958 A1 | 1/2011 | Wardle et al. |
| 2011/0046536 A1 | 2/2011 | Stegmann et al. |
| 2011/0046728 A1 | 2/2011 | Shareef et al. |
| 2011/0054418 A1 | 3/2011 | Pugh et al. |
| 2011/0066098 A1 | 3/2011 | Stergiopulos |
| 2011/0071454 A1 | 3/2011 | Dos Santos et al. |
| 2011/0071456 A1 | 3/2011 | Rickard |
| 2011/0071458 A1 | 3/2011 | Rickard |
| 2011/0071459 A1 | 3/2011 | Rickard et al. |
| 2011/0071505 A1 | 3/2011 | Rickard et al. |
| 2011/0086095 A1 | 4/2011 | Jacob et al. |
| 2011/0092878 A1 | 4/2011 | Tu et al. |
| 2011/0098627 A1 | 4/2011 | Wilcox |
| 2011/0098640 A1 | 4/2011 | Horne et al. |
| 2011/0098809 A1 | 4/2011 | Wardle et al. |
| 2011/0105987 A1 | 5/2011 | Bergheim et al. |
| 2011/0106006 A1 | 5/2011 | Martin et al. |
| 2011/0112475 A1 | 5/2011 | Benson |

(56) References Cited

U.S. PATENT DOCUMENTS

| | | |
|---|---|---|
| 2011/0118649 A1 | 5/2011 | Stegmann et al. |
| 2011/0118835 A1 | 5/2011 | Silvestrini et al. |
| 2011/0130831 A1 | 6/2011 | Badawi et al. |
| 2011/0144559 A1 | 6/2011 | Lafdi et al. |
| 2011/0196487 A1 | 8/2011 | Badawi et al. |
| 2011/0224597 A1 | 9/2011 | Stegmann et al. |
| 2011/0244014 A1 | 10/2011 | Williams et al. |
| 2011/0245753 A1 | 10/2011 | Williams et al. |
| 2011/0248671 A1 | 10/2011 | Dos Santos et al. |
| 2011/0251568 A1 | 10/2011 | Beeley et al. |
| 2011/0257623 A1 | 10/2011 | Marshall et al. |
| 2011/0319806 A1 | 12/2011 | Wardle |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0035528 A1 | 2/2012 | Coppeta et al. |
| 2012/0059338 A1 | 3/2012 | Beeley et al. |
| 2012/0059461 A1 | 3/2012 | Badawi et al. |
| 2012/0071809 A1 | 3/2012 | Tu et al. |
| 2012/0078158 A1 | 3/2012 | Haffner et al. |
| 2012/0078362 A1 | 3/2012 | Haffner et al. |
| 2012/0089072 A1 | 4/2012 | Cunningham, Jr. |
| 2012/0089073 A1 | 4/2012 | Cunningham, Jr. |
| 2012/0109040 A1 | 5/2012 | Smedley et al. |
| 2012/0130467 A1 | 5/2012 | Selden et al. |
| 2012/0165933 A1 | 6/2012 | Haffner et al. |
| 2012/0179087 A1 | 7/2012 | Schieber et al. |
| 2012/0184892 A1 | 7/2012 | Bigler et al. |
| 2012/0197217 A1 | 8/2012 | Coldren |
| 2012/0203160 A1 | 8/2012 | Kahook et al. |
| 2012/0238994 A1 | 9/2012 | Nazzaro et al. |
| 2012/0257167 A1 | 10/2012 | Gille et al. |
| 2012/0259195 A1 | 10/2012 | Haffner et al. |
| 2012/0289883 A1 | 11/2012 | Meng et al. |
| 2012/0302861 A1 | 11/2012 | Marshall et al. |
| 2012/0310072 A1 | 12/2012 | Grieshaber |
| 2012/0323159 A1 | 12/2012 | McDonnell et al. |
| 2013/0006164 A1 | 1/2013 | Yaron et al. |
| 2013/0006165 A1 | 1/2013 | Eutenener et al. |
| 2013/0018295 A1 | 1/2013 | Haffner et al. |
| 2013/0018296 A1 | 1/2013 | Bergheim et al. |
| 2013/0079701 A1 | 3/2013 | Schieber et al. |
| 2013/0090534 A1 | 4/2013 | Burns et al. |
| 2013/0102949 A1 | 4/2013 | Baerveldt |
| 2013/0144202 A1 | 6/2013 | Field et al. |
| 2013/0150770 A1 | 6/2013 | Horvath et al. |
| 2013/0150773 A1 | 6/2013 | Nissan et al. |
| 2013/0150774 A1 | 6/2013 | Field et al. |
| 2013/0150776 A1 | 6/2013 | Bohm et al. |
| 2013/0150777 A1 | 6/2013 | Bohm et al. |
| 2013/0150779 A1 | 6/2013 | Field |
| 2013/0150959 A1 | 6/2013 | Schieber et al. |
| 2013/0158381 A1 | 6/2013 | Rickard |
| 2013/0158462 A1 | 6/2013 | Wardle et al. |
| 2013/0165840 A1 | 6/2013 | Orge |
| 2013/0172804 A1 | 7/2013 | Schieber et al. |
| 2013/0184631 A1 | 7/2013 | Pinchuk |
| 2013/0245532 A1 | 9/2013 | Tu et al. |
| 2013/0253404 A1 | 9/2013 | Tu |
| 2013/0253405 A1 | 9/2013 | Tu |
| 2013/0253528 A1 | 9/2013 | Haffner et al. |
| 2013/0281910 A1 | 10/2013 | Tu et al. |
| 2013/0310930 A1 | 11/2013 | Tu et al. |
| 2014/0034607 A1 | 2/2014 | Meng et al. |
| 2014/0046437 A1 | 2/2014 | Renke |
| 2014/0052046 A1 | 2/2014 | Peartree et al. |
| 2014/0135916 A1 | 5/2014 | Clauson et al. |
| 2014/0276332 A1 | 9/2014 | Crimaldi et al. |
| 2015/0148730 A1 | 5/2015 | Lynch et al. |
| 2015/0223981 A1 | 8/2015 | Smedley et al. |
| 2015/0342875 A1 | 12/2015 | Haffner |
| 2015/0374546 A1 | 12/2015 | Hill |
| 2016/0354309 A1 | 12/2016 | Heitzmann et al. |
| 2017/0135857 A1 | 5/2017 | Haffner et al. |
| 2017/0156848 A1 | 6/2017 | Schieber |
| 2017/0273829 A1 | 9/2017 | Tu et al. |
| 2018/0021170 A1 | 1/2018 | Haffner et al. |
| 2018/0028361 A1 | 2/2018 | Haffner et al. |
| 2018/0036172 A1 | 2/2018 | Haffner et al. |
| 2018/0085065 A1 | 3/2018 | Haffner et al. |
| 2018/0104102 A1 | 4/2018 | Lynch et al. |
| 2018/0161205 A1 | 6/2018 | Tu et al. |
| 2018/0280194 A1 | 10/2018 | Heitzmann et al. |
| 2018/0303665 A1 | 10/2018 | Heitzmann et al. |
| 2018/0325732 A1 | 11/2018 | Burns et al. |
| 2018/0333296 A1 | 11/2018 | Heitzmann et al. |
| 2018/0369017 A1 | 12/2018 | Schieber et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0083307 A1 | 3/2019 | Burns et al. |
| 2019/0083313 A1 | 3/2019 | Berlin |
| 2019/0104936 A1 | 4/2019 | Gunn et al. |
| 2019/0105077 A1 | 4/2019 | Kalina, Jr. et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2020/0155349 A1 | 5/2020 | Haffner et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |
| 2022/0233349 A1 | 7/2022 | Haffner et al. |
| 2022/0233354 A1 | 7/2022 | Haffner et al. |

FOREIGN PATENT DOCUMENTS

| | | |
|---|---|---|
| AU | 2004264913 | 12/2011 |
| AU | 2009251058 B2 | 12/2013 |
| CA | 2273331 C | 6/1998 |
| CA | 2244646 A1 | 2/1999 |
| CA | 2311244 C | 6/1999 |
| CA | 2442652 C | 1/2011 |
| CA | 2766131 | 1/2011 |
| CA | 2683224 C | 12/2014 |
| CA | 2830555 | 4/2015 |
| CA | 2762536 | 11/2020 |
| CH | 92111244 | 7/1993 |
| CN | 101396335 | 4/2009 |
| DE | 19840047 A1 | 3/2000 |
| DE | 10127666 A1 | 1/2003 |
| EP | 0550791 A1 | 7/1993 |
| EP | 0858788 A1 | 8/1998 |
| EP | 0898947 A2 | 3/1999 |
| EP | 1114627 A1 | 7/2001 |
| EP | 1592407 | 11/2005 |
| EP | 1977724 A1 | 10/2008 |
| EP | 2260803 A2 | 12/2010 |
| EP | 2260804 A2 | 12/2010 |
| EP | 2263621 A1 | 12/2010 |
| EP | 2351589 A1 | 8/2011 |
| EP | 2982354 A1 | 2/2016 |
| EP | 2985012 A1 | 2/2016 |
| FR | 2553658 A1 | 4/1985 |
| FR | 2710269 A1 | 3/1995 |
| FR | 9311476 | 3/1995 |
| FR | 2721499 A1 | 12/1995 |
| FR | 2757068 A1 | 6/1998 |
| GB | 2296663 A | 7/1996 |
| JP | 2005-502811 | 5/1993 |
| JP | 2010-248869 | 9/1998 |
| JP | 2011-123205 | 5/1999 |
| JP | 2001-523519 | 11/2001 |
| JP | 2002-541977 | 12/2002 |
| JP | 2001-507969 | 1/2003 |
| JP | 2004-518450 | 6/2004 |
| JP | 3703721 B2 | 7/2005 |

(56) References Cited

FOREIGN PATENT DOCUMENTS

| | | |
|---|---|---|
| JP | 2005-525835 | 9/2005 |
| JP | 2007-535386 | 12/2007 |
| JP | 2008-500878 | 1/2008 |
| JP | 4031836 B2 | 1/2008 |
| JP | 2009-523540 | 6/2009 |
| JP | 2009-542370 | 12/2009 |
| JP | 2010-533565 | 10/2010 |
| JP | 4688444 B2 | 2/2011 |
| JP | 2011-520805 | 7/2011 |
| JP | 2011-522575 | 8/2011 |
| JP | 2012-516224 | 7/2012 |
| JP | 2012-198134 | 9/2012 |
| JP | 2013-063308 | 4/2013 |
| JP | 5255402 B2 | 4/2013 |
| JP | 5323011 B2 | 7/2013 |
| JP | 2013-208434 | 10/2013 |
| JP | 5502811 | 5/2014 |
| JP | 2014-193366 | 10/2014 |
| JP | 2014-240022 | 12/2014 |
| RU | 2022539 C1 | 11/1994 |
| RU | 2143250 C1 | 12/1999 |
| WO | WO 89/00869 A1 | 2/1989 |
| WO | WO 91/08784 | 6/1991 |
| WO | WO 91/18568 A1 | 12/1991 |
| WO | WO 92/00112 | 1/1992 |
| WO | WO 92/19294 | 11/1992 |
| WO | WO 94/13234 | 6/1994 |
| WO | WO 95/08310 A1 | 3/1995 |
| WO | WO 1996/020742 | 7/1996 |
| WO | WO 96/36377 | 11/1996 |
| WO | WO 98/23237 A1 | 6/1998 |
| WO | WO 98/30181 A1 | 7/1998 |
| WO | WO 98/35639 A1 | 8/1998 |
| WO | WO 98/37831 | 9/1998 |
| WO | WO 99/26567 A1 | 6/1999 |
| WO | WO 99/30641 A1 | 6/1999 |
| WO | WO 99/38470 A2 | 8/1999 |
| WO | WO 1999/56637 | 11/1999 |
| WO | WO 00/13627 A1 | 3/2000 |
| WO | WO 00/64390 A1 | 11/2000 |
| WO | WO 00/64391 A1 | 11/2000 |
| WO | WO 00/64393 A1 | 11/2000 |
| WO | WO 00/67687 A1 | 11/2000 |
| WO | WO 2000/64389 | 11/2000 |
| WO | WO 00/72788 A1 | 12/2000 |
| WO | WO 01/41685 A2 | 6/2001 |
| WO | WO 01/50943 A2 | 7/2001 |
| WO | WO 01/78631 A2 | 10/2001 |
| WO | WO 01/78656 A2 | 10/2001 |
| WO | WO 2001/080825 | 11/2001 |
| WO | WO 01/97727 | 12/2001 |
| WO | WO 02/36052 | 5/2002 |
| WO | WO 2002/053129 | 7/2002 |
| WO | WO 02/074052 A2 | 9/2002 |
| WO | WO 02/080811 | 10/2002 |
| WO | WO 02/102274 A2 | 12/2002 |
| WO | WO 03/015659 A2 | 2/2003 |
| WO | WO 03/041622 | 5/2003 |
| WO | WO 03/045290 A1 | 6/2003 |
| WO | WO 2003/061625 | 7/2003 |
| WO | WO 03/073968 A2 | 9/2003 |
| WO | WO 2004/043435 | 5/2004 |
| WO | WO 2004/073552 | 9/2004 |
| WO | WO 2004/093761 A1 | 11/2004 |
| WO | WO 05/046782 A2 | 5/2005 |
| WO | WO 05/055873 A2 | 6/2005 |
| WO | WO 05/107664 A2 | 11/2005 |
| WO | WO 2007/087061 | 8/2007 |
| WO | WO 2008/005873 | 1/2008 |
| WO | WO 08/061043 A2 | 5/2008 |
| WO | WO 2008/060359 | 5/2008 |
| WO | WO 2008/083118 | 7/2008 |
| WO | WO 2008/157614 | 12/2008 |
| WO | WO 2009/012406 | 1/2009 |
| WO | WO 2009/035571 | 3/2009 |
| WO | WO 2009/063222 | 5/2009 |
| WO | WO 2009/126569 | 10/2009 |
| WO | WO 2009/151543 | 12/2009 |
| WO | WO 2010/006053 | 1/2010 |
| WO | WO 2010/078063 | 7/2010 |
| WO | WO 10/135369 | 11/2010 |
| WO | WO 11/020633 A1 | 2/2011 |
| WO | WO 2011/127064 | 10/2011 |
| WO | WO 12/071476 | 5/2012 |
| WO | WO 13/148275 | 10/2013 |
| WO | WO 2017/030917 | 2/2017 |
| WO | WO 2019/036025 A2 | 2/2019 |

OTHER PUBLICATIONS

International Preliminary Report on Patentability in PCT/US2016/053570 dated Mar. 27, 2018.

Alexander, L., et al., Disistronic Polioviruses as Expression Vectors for Foreign Genes. 1994. Aids Research and Human Retroviruses. vol. 10, Supplement 2, S57-S60.

Bae, et al., "In vitro experiment of the pressure regulating valve for a glaucoma implant", Journal of Micromechanics and Microengineering 13.5, 13:613-619, No. 5, Sep. 2003.

Bucciarelli, Patrice D., Working Model is Next Step in Team's Long Journey to Commercial Product, Healthfirst, Business First of Louisville, louisville.bizjournals.com, Feb. 27, 2004.

"Changing Perspectives in Glaucoma Management," Innovations in Glaucoma 2010.

Cairns, J.E., "Trabeculectomy: Preliminary report of a new method", Am. J. Ophthalmology, 66:673-79 (1968).

Chen, et al., "Trabeculetomy combined with implantation of silicon rubber slice for intractable glaucoma", Eye Science, 18:95-98, vol. 2, Jun. 2002.

Fine, Ben S., et al., "A Clinicopathologic Study of Four Cases of Primary Open-Angle Glaucoma Compared to Normal Eyes", American Journal of Ophthalmology, vol. 91, No. 1, 1981, pp. 88-105.

Fiore, P.M., et al., Use of neodymium: YAG laser to open an occluded molteno tube, Ophthalmic Surgery, May 1989; 20(5): 373-74.

Gimbel, H.V., et al., "Small incision trabeculotomy combined with phacoemulsificatin and intraocular lens implantation", J Cataract Refract Surg, vol. 19:92-96 (Jan. 1993).

Gothwal, et al., "Migration of seton into the anterior chamber", Eye, 16:85-97, 2002.

Hoskins, H. Dunbar, et al., Diagnosis and Therapy of the Glaucomas, Chapter 4: Aqueous Humor Outflow, 61 edition, pp. 41-66 (1989) (28 pages).

Huang, Morgan C., et al., Intermediate-term Clinical Experience with the Ahmed Glaucoma Valve Implant, 127 Am. J. Ophthalmol. 27 (Jan. 1999).

Jordon, et al., "A Novel Approach to Suprachoroidal Drainage for the Surgical Treatment of Intractable Glaucoma," J Glaucoma 15(3): 200-205 (2006).

Kampik, Anselm Franz Grehn, *Nutzen und Risiken Augenärzticher Therapie, Hauotreferate der XXXIII, Essener Fortbildung für Augenärzte*, Dec. 1998. (English translated version enclosed Benefits and Risks of Opthalmological Therapy).

Kershner, Robert, "Nonpenetrating trabulectomy with placement of a collagen drainage device", J. Cataract Refract. Sug., 21:608-611 (1995).

Klemm, A. Balazs, J. Draeger, R. Wiezorrek, *Experimental use of space-retaining substances with extended duration: functional and morphological results*, Graefe's Arch Clin Exp Ophthalmol (1995) 233:592-597.

Krupin, Theodore, et al., Filtering valve implant surgery for eyes with neovascular glaucoma, 89 Am. J. Ophthalmol. 338 (Mar. 1980).

Mermoud, A., et al., "Comparison of deep sclerectomy with collagen implant and trabeculectomy in open-angle glaucoma", J. Cataracat Refract. Surg., vol. 25, No. 3, Mar. 1999, pp. 323-331 (abstract only).

Miyazaki, Akiko, et al., Postoperative Results Of Combined Trabeculotomy, Phacoemulsification And Intraocular Lens Implan-

(56) References Cited

OTHER PUBLICATIONS tation With Self-Sealing Wound, Japanese Journal of Ophthalmic Surgery, 1997, pp. 537-542, vol. 10, No. 4.

Molteno, A.C.B., et al., Implants for draining neovascular glaucoma, 61 Br. J. Ophthalmol. 120 (1977).

Moses, Robert A., M.D.; Circumferential Flow in Schlemm's Canal; American Journal of Ophthalmology, Sep. 1979, vol. 88, No. 3, Part II, :pp. 585-591.

Nguyen, Quang H., et al., Complications of Baerveldt Glaucoma Drainage Implants, 116 Arch. Ophthalmol. 571 (May 1998).

Refojo, "Current status of biomaterials in ophthalmology", Survey of ophthalmology, 26:257-265, No. 5, 1982.

Rizq, et al., Intraocular Pressure Measurement at the Choroid Surface: A Feasibility Study with Implications for Implantable Microsystems, Br J Ophthalmol 2001; 85:868-871, Jul. 2001.

Saxena, Sandeep. "Clinical Ophthalmology". 2011. pp. 245.

Schocket, Investigations of the Reasons for Success and Failure in the Anterior Shunt-to-the Encircling-Band Procedure in the Treatment of Refractory Glaucoma, Tr. Am. Ophth. Soc., 84:743 (1986).

Scott, et al., "Use of glaucoma drainage devices in the management of glaucoma associated with aniridia", American Journal of Ophthalmology, 135:155-159, No. 2, Feb. 1, 2003.

Shields, M. Bruce, MD, *A Study Guide for Glaucoma: Aqueous Humor Dynamics*, Copyright 1982, pp. 6-43.

Stefansson, J., "An Operation for Glaucoma", American J. Ophthalmology, 8:681-693 (1925).

"Transcend Medical CyPass® System—Instructions for Use," (Release date Apr. 29, 2013).

Tham, et al., "Incisional surgery for angle closure glaucoma", Seminars in Ophthalmology, 17:92-99, No. 2, Jun. 2002.

Topouzis, Fotis, et al., Follow-up of the Original Cohort With the Ahmed Glaucoma Valve Implant, 128 Am. J. Ophthalmol. 198 (Aug. 1999).

Tripathi, et al., Functional Anatomy of the Anterior Chamber Angle, Biomedical Foundation of Ophthalmology, vol. 1, Chapter 10,pp. 1-74; edited by Thomas Dune and Edward Jaeger, Revised Edition, 1983,—Harper & Row, Publishers.

Tun, et al., Assessment of Trabecular Meshwork Width Using Swept Source Optical Coherence Tomography, 251:6 Graefes Arch. Clin. Exp. Ophthalmol. 1587 (2013).

Wagner, Justin A., Edwards, Aurélie, and Schuman, Joel S., Characterization of Uveoscleral Outflow in Enucleated Porcine Eyes Perfused Under Constant Pressure, *Invest Ophthalmol Vis Sci*. Sep. 2004; 45(9): 3203-3206 (9 pages).

Webster's Third New International Dictionary of the English Language (Unabridged), definitions of "deploy" and "deployment", p. 605 (2002) (4 pages).

Wilcox, Michael J. et al. "Hypothesis for Improving Accessory Filtration by Using Geometry", J. Glaucoma, vol. 3, No. 3, pp. 244-247 (1994).

Wilcox, Michael J. et al. "Performance of a New, Low-volume, High-Surface Area Aqueous Shunt in Normal Rabbit Eyes", J. Glaucoma, vol. 9, No. 1, pp. 74-82 (Feb. 2000).

Wilson, Ellen D., "Implants offer choices for glaucoma surgeons", EW Glaucoma, Oct. 11, 1999, website "http://www.eyeorld.org/sep99/999p60.asp".

Wilcox et al., Latest Research: Tear Biomarkers, Jun. 29, 2011, 5 pages.

Yan, et al., "Schlemm's Canal and Trabecular Meshwork in Eyes with Primary Open Angle Glaucoma: A Comparative Study Using High-Frequency", PLOS One, 15 pages, Jan. 4, 2016.

European Exam Report, EPO App. No. 08 102 896.1, dated Nov. 4, 2010.

Communication from European Patent Office for European App. No. 08102896.1 (dated Jul. 2, 2012).

Appeal in European Application No. 08102896.1 dated Aug. 27, 2012.

International Search Report and Written Opinion in PCT/US2016/053570 dated Mar. 9, 2017.

International Preliminary Report on Patentability in PCT/US2016/053570 dated Jan. 23, 2018.

Chen et al., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.

Grant, W.M., MD, "Further Studies on Facility of Flow Through the Trabecular Meshwork", AMA Archives of Ophthalmology, Oct. 1958, vol. 60, pp. 523-533.

https://entokey.com/gonioscopy-2/ Uploaded Oct. 2016.

Hulzen et al., "Effect of Fixation on Juxtacanalicular Tissue and Schlemm's canal", Investigative Ophthalmology & Visual Science, vol. 37, No. 1 (Jan. 1996).

Jain et al., "Development of polyvinyl alcohol-gelatin membranes for antibiotic delivery in the eye", Drug Development and Industrial Pharmacy, 2011, Informa Healthcare USA, Inc., 12 pages.

Johnson, et al. "Mechanisms and Routes of Aqueous Humor Drainage" in D.M. Albert, & F.A. Jakobiec (Eds.), Principles and Practice of Ophthalmology, pp. 2577-2595, WB Saunders, Philadelphia (2000).

Katuri et al., "Intraocular Pressure Monitoring Sensors", IEEE Sensors Journal, vol. 8, No. 1, Jan. 2008, 8 pp.

McLaren et al., "Continuous Measurement of Intraocular Pressure in Rabbits by Telemetry," Investigative Ophthalmology & Visual Science, vol. 37, No. 6, pp. 966-975, May 1996.

Online encyclopedia article "Hyaluronan," section on "Medical Applications" accessed Monday, Sep. 27, 2010. http://en.wikipedia.org/wiki/Hyaluronic_acid.

Sampaolesi, et al., "Scanning Electron Microscopy of the Trabecular Meshwork in Normal-Glaucomatous Eyes", Invest Ophthalmol Vis Sci, pp. 302-314 (1977).

Spiegel, Detlev, "Benefits and Risks of Ophthalmological Treatment" Bucherei des Augenarztes I The Ophthalmologist's Library, vol. 139, Oct. 15, 1998.

Spiegel, "7 chirurgische Glaukomtherapie", pp. 79-88 (English translation enclosed).

Spiegel et al., "Schlemm's Canal Implant: A New Method to Lower Intraocular Pressure in Patients With POAG", Opthalmic Surgery and Lasers, vol. 30(6):492-494 (1999).

Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.

Walter et al., "Development of a Completely Encapsulated Intraocular Pressure Sensor", Ophthalmic Res 2000; 32:278-284. Nov. 1999.

\* cited by examiner

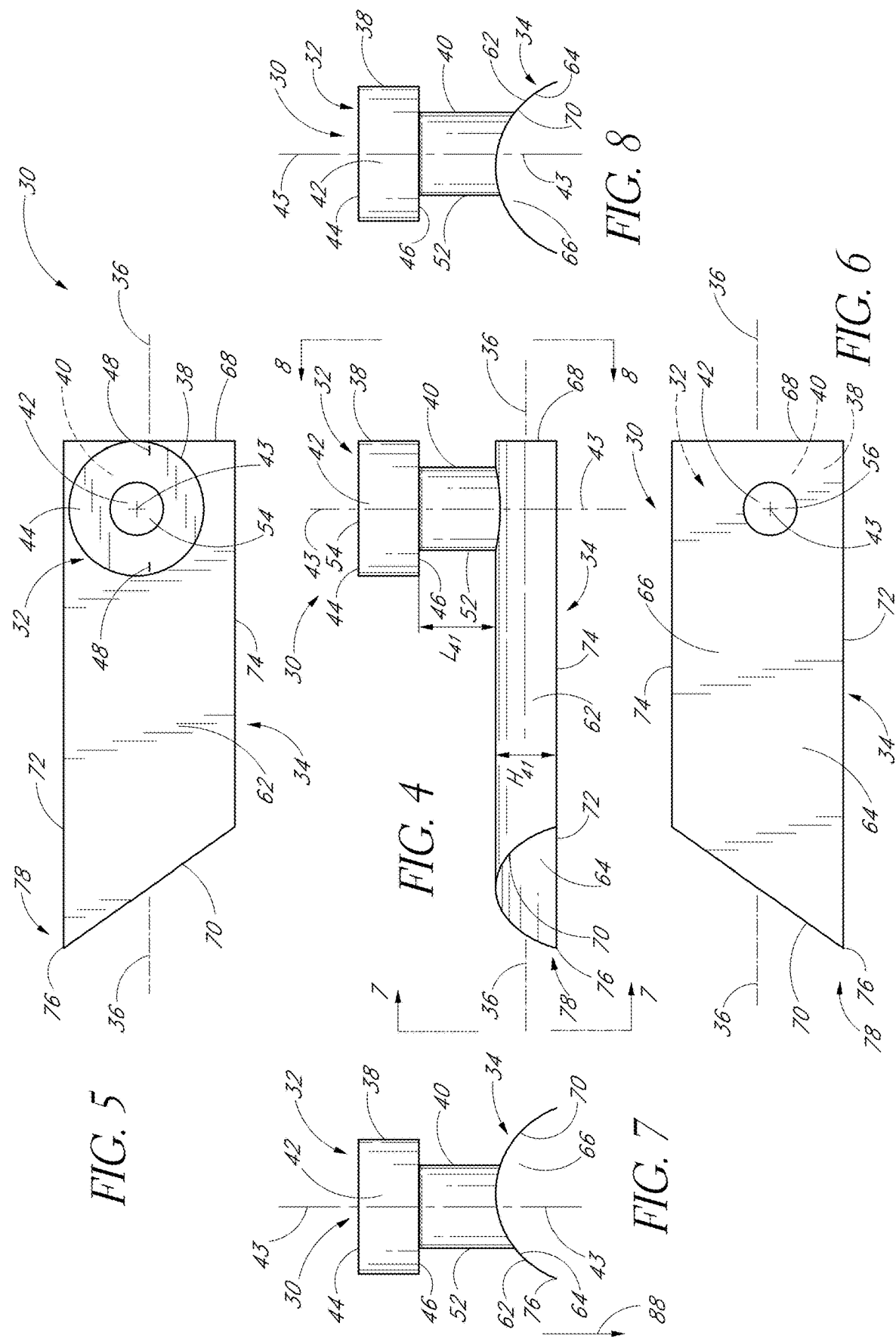

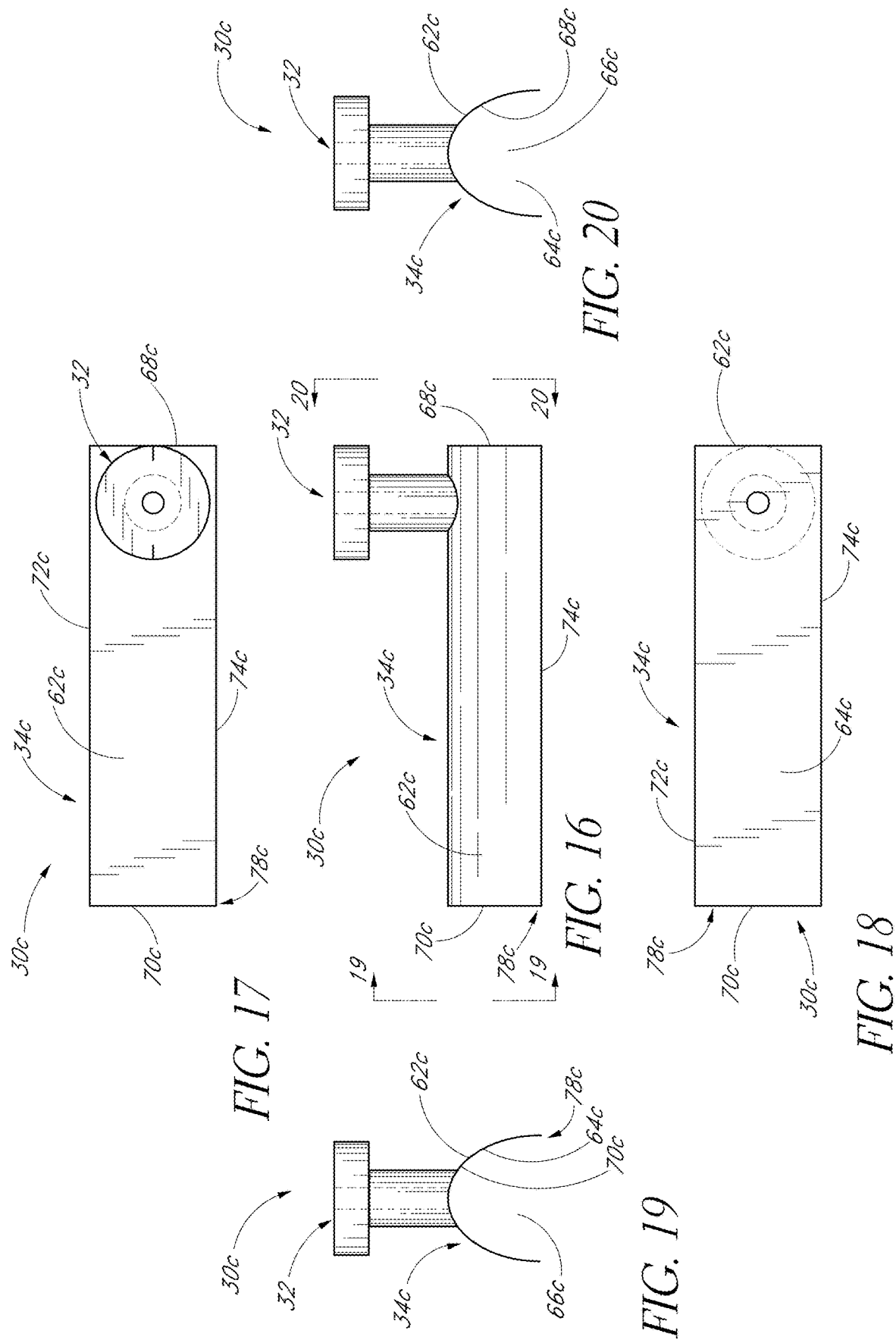

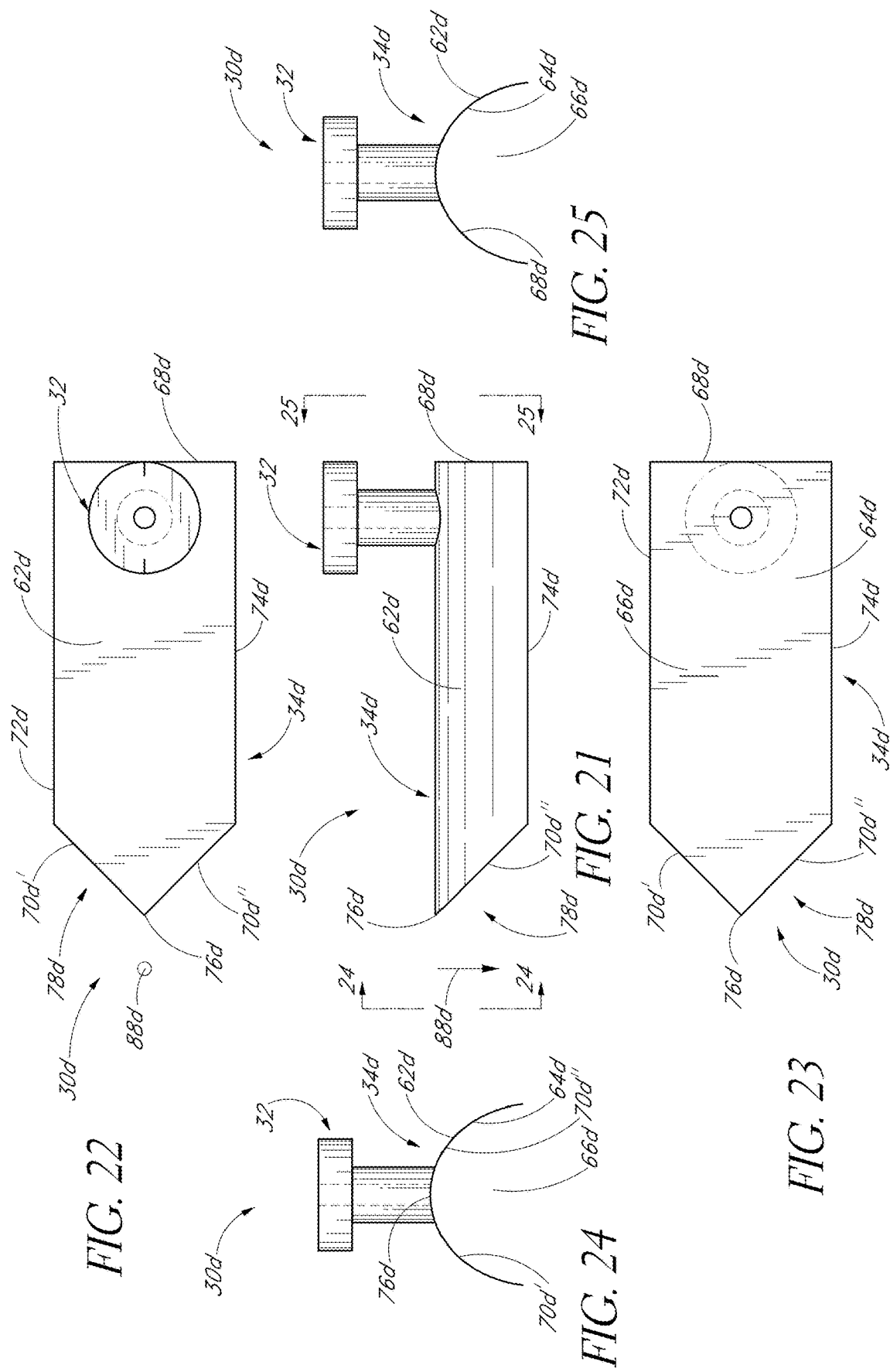

FIG. 36D
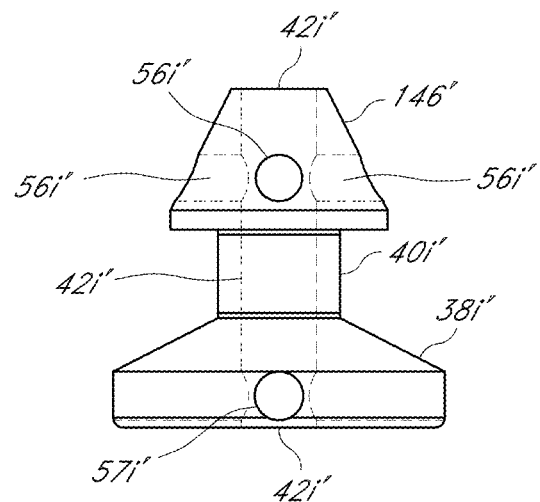
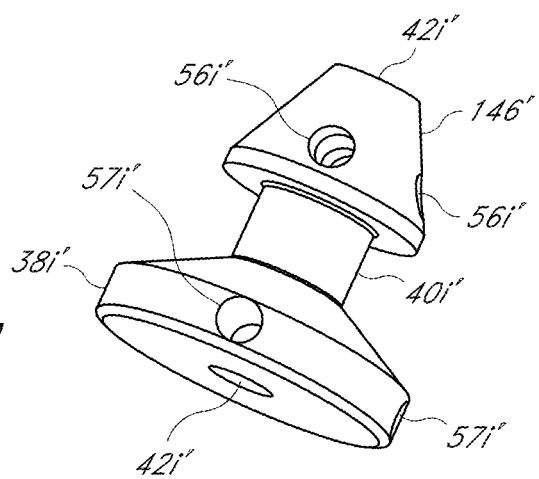
FIG. 36E
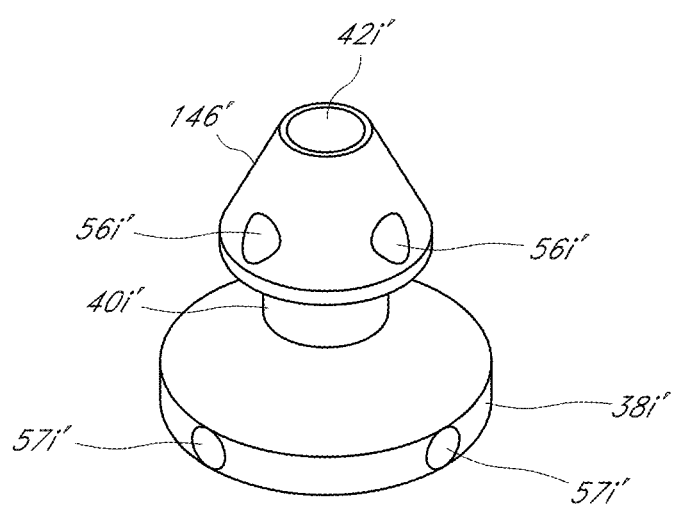
FIG. 36F

FIG. 36G
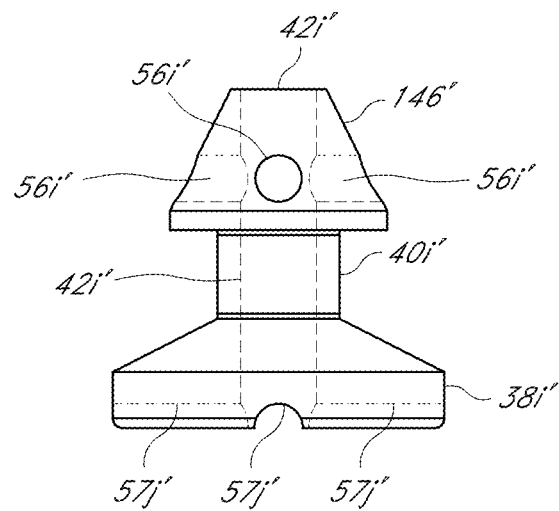
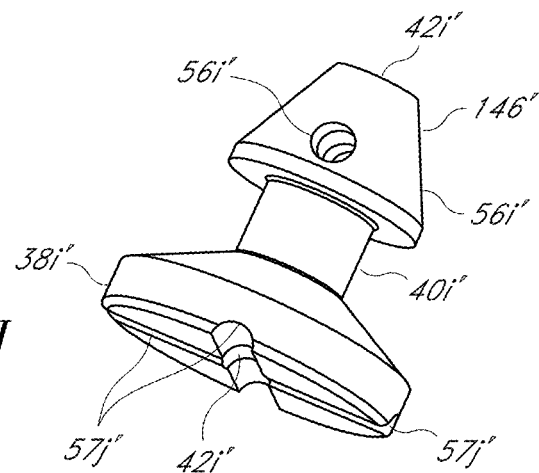
FIG. 36H
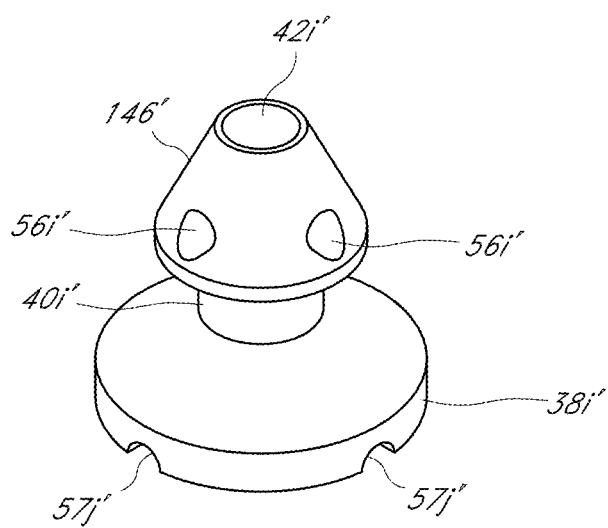
FIG. 36I

FIG. 36J
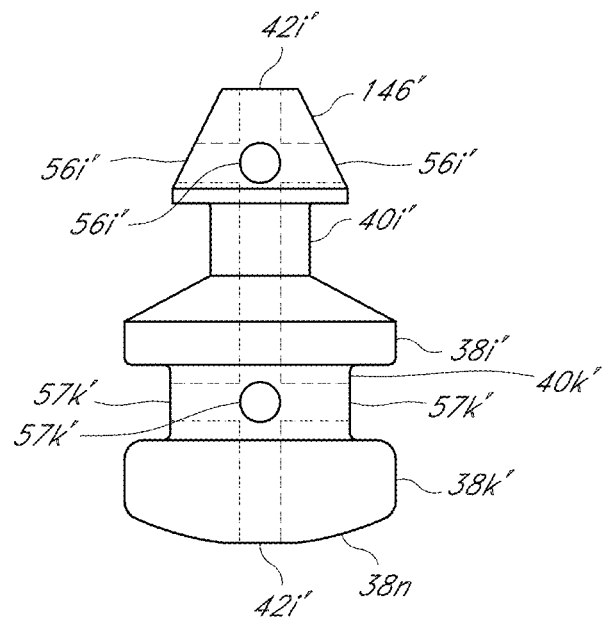
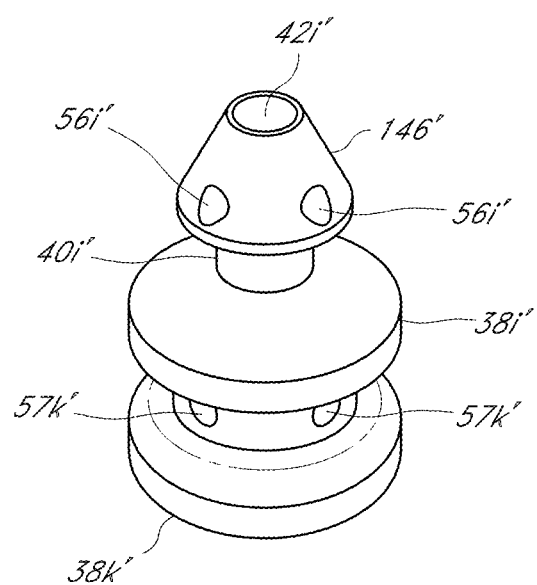
FIG. 36K

GLAUCOMA STENT AND METHODS THEREOF FOR GLAUCOMA TREATMENT

RELATED APPLICATION

This application is a continuation application of U.S. patent application Ser. No. 14/207,240 filed Mar. 12, 2014, now U.S. Pat. No. 10,517,759, titled GLAUCOMA STENT AND METHODS THEREOF FOR GLAUCOMA TREATMENT, which claims priority benefit of U.S. Provisional Application No. 61/794,832 filed Mar. 15, 2013, titled GLAUCOMA STENT AND METHODS THEREOF FOR GLAUCOMA TREATMENT, the entire contents of which is incorporated herein by reference.

BACKGROUND OF THE INVENTION

Field of the Invention

The invention relates generally to medical devices and methods for reducing the intraocular pressure in an animal eye and, more particularly, to shunt type devices for permitting aqueous outflow from the eye's anterior chamber and associated methods thereof for the treatment of glaucoma.

Description of the Related Art

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10-15%); infection (a lifelong risk of 2-5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture: Q-switched Neodynium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846,172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341-346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and U.S. Pat. No. 6,050,970 to Baerveldt.

All of the above surgeries and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Therefore, there is a great clinical need for a method of treating glaucoma that is faster, safer, and less expensive than currently available modalities.

SUMMARY OF THE INVENTION

The trabecular meshwork and juxtacanilicular tissue together provide the majority of resistance to the outflow of aqueous and, as such, are logical targets for surgical approach in the treatment of glaucoma. Various embodiments of glaucoma shunts are disclosed herein for aqueous to exit through the trabecular meshwork (major route) or uveal scleral outflow (minor route) or other route effective to reduce intraocular pressure (IOP).

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2-5% to about 0.05%.

U.S. Pat. No. 6,638,239, filed Apr. 14, 2000, entitled APPARATUS AND METHOD FOR TREATING GLAUCOMA, and U.S. Pat. No. 6,736,791, filed Nov. 1, 2000, entitled GLAUCOMA TREATMENT DEVICE, disclose devices and methods of placing a trabecular shunt ab interno, i.e., from inside the anterior chamber through the trabecular meshwork, into Schlemm's canal. The entire contents of each one of these copending patent applications are hereby incorporated by reference herein. The invention encompasses both ab interno and ab externo glaucoma shunts or stents and methods thereof.

Techniques performed in accordance with aspects herein may be referred to generally as "trabecular bypass surgery." Advantages of this type of surgery include lowering intraocular pressure in a manner which is simple, effective, disease site-specific, and can potentially be performed on an outpatient basis.

Generally, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. Pat. No. 6,638,239, filed Apr. 14, 2000, the entire contents of which are hereby incorporated by reference herein, discloses trabecular bypass surgery.

As described in U.S. Pat. No. 6,638,239, filed Apr. 14, 2000, and U.S. Pat. No. 6,736,791, filed Nov. 1, 2000, the entire contents each one of which are hereby incorporated by reference herein, a trabecular shunt or stent for transporting aqueous humor is provided. The trabecular stent includes a hollow, elongate tubular element, having an inlet section and an outlet section. The outlet section may optionally include two segments or elements, adapted to be positioned and stabilized inside Schlemm's canal. In one embodiment, the device appears as a "T" shaped device.

In one aspect of the invention, a delivery apparatus (or "applicator") is used for placing a trabecular stent through a trabecular meshwork of an eye. Certain embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

Some aspects of the invention relate to devices for reducing intraocular pressure by providing outflow of aqueous from an anterior chamber of an eye. The device generally comprises an elongated tubular member and cutting means. The tubular member is adapted for extending through a trabecular meshwork of the eye. The tubular member generally comprises a lumen having an inlet port and an outlet port for providing a flow pathway. The cutting means is mechanically connected to the tubular member for creating an incision in the trabecular meshwork for receiving at least a portion of the tubular member.

In one aspect, a self-trephining glaucoma stent is provided for reducing and/or balancing intraocular pressure in an eye. The stent generally comprises a snorkel and a curved blade. The snorkel generally comprises an upper seat for stabilizing said stent within the eye, a shank and a lumen. The shank is mechanically connected to the seat and is adapted for extending through a trabecular meshwork of the eye. The lumen extends through the snorkel and has at least one inlet flow port and at least one outlet flow port. The blade is mechanically connected to the snorkel. The blade generally comprises a cutting tip proximate a distal-most point of the blade for making an incision in the trabecular meshwork for receiving the shank.

Some aspects of the invention relate to methods of implanting a trabecular stent device in an eye. In one aspect, the device has a snorkel mechanically connected to a blade. The blade is advanced blade through a trabecular meshwork of the eye to cut the trabecular meshwork and form an incision therein. At least a portion of the snorkel is inserted in the incision to implant the device in the eye.

Some aspects provide a self-trephining glaucoma stent and methods thereof which advantageously allow for a "one-step" procedure in which the incision and placement of the stent are accomplished by a single device and operation. This desirably allows for a faster, safer, and less expensive surgical procedure. In any of the embodiments, fiducial markings, indicia, or the like and/or positioning of the stent device in a preloaded applicator may be used for proper orientation and alignment of the device during implantation.

Among the advantages of trabecular bypass surgery is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 4 is a side elevation view of the stent of FIG. 3;

FIG. 5 is a top plan view of the stent of FIG. 3;

FIG. 6 is a bottom plan view of the stent of FIG. 3;

FIG. 7 is a front end view of the stent of FIG. 3 (along line 7-7 of FIG. 4);

FIG. 8 is a rear end view of the stent of FIG. 3 (along line 8-8 of FIG. 4);

FIG. 16 is a side elevation view of a glaucoma stent having features and advantages in accordance with one embodiment of the invention;

FIG. 17 is a top plan view of the stent of FIG. 16;

FIG. 18 is a bottom plan view of the stent of FIG. 16;

FIG. 19 is a front end view along line 19-19 of FIG. 16;

FIG. 20 is a rear end view along line 20-20 of FIG. 16;

FIG. 21 is a side elevation view of a glaucoma stent having features and advantages in accordance with one embodiment of the invention;

FIG. 22 is a top plan view of the stent of FIG. 21;

FIG. 23 is a bottom plan view of the stent of FIG. 21;

FIG. 24 is a front end view along line 24-24 of FIG. 21;

FIG. 25 is a rear end view along line 25-25 of FIG. 21;

FIG. 36D is a side elevation view of a glaucoma stent having features and advantages in accordance with one embodiment of the invention;

FIG. 36E is a perspective view of the stent of FIG. 36D;

FIG. 36F is a another perspective view of the stent of FIG. 36D;

FIG. 36G is a side elevation view of a glaucoma stent having features and advantages in accordance with one embodiment of the invention;

FIG. 36H is a perspective view of the stent of FIG. 36G;

FIG. 36I is a another perspective view of the stent of FIG. 36G;

FIG. 36J is a side elevation view of a glaucoma stent having features and advantages in accordance with one embodiment of the invention;

FIG. 36K is a perspective view of the stent of FIG. 36J;

DETAILED DESCRIPTION OF THE PREFERRED EMBODIMENTS

The preferred embodiments of the invention described herein relate particularly to surgical and therapeutic treatment of glaucoma through reduction of intraocular pressure. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
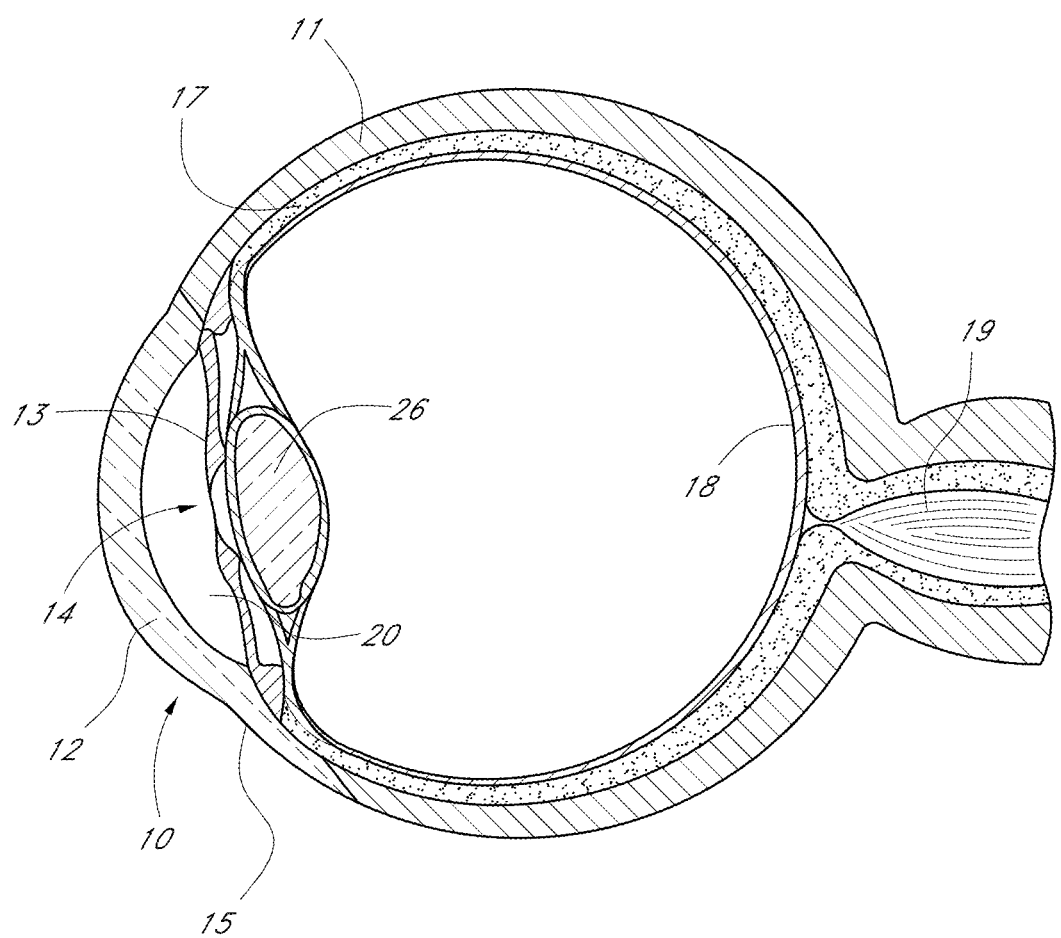
FIG. 1 is a coronal cross-sectional view of an eye.
Figure 2:
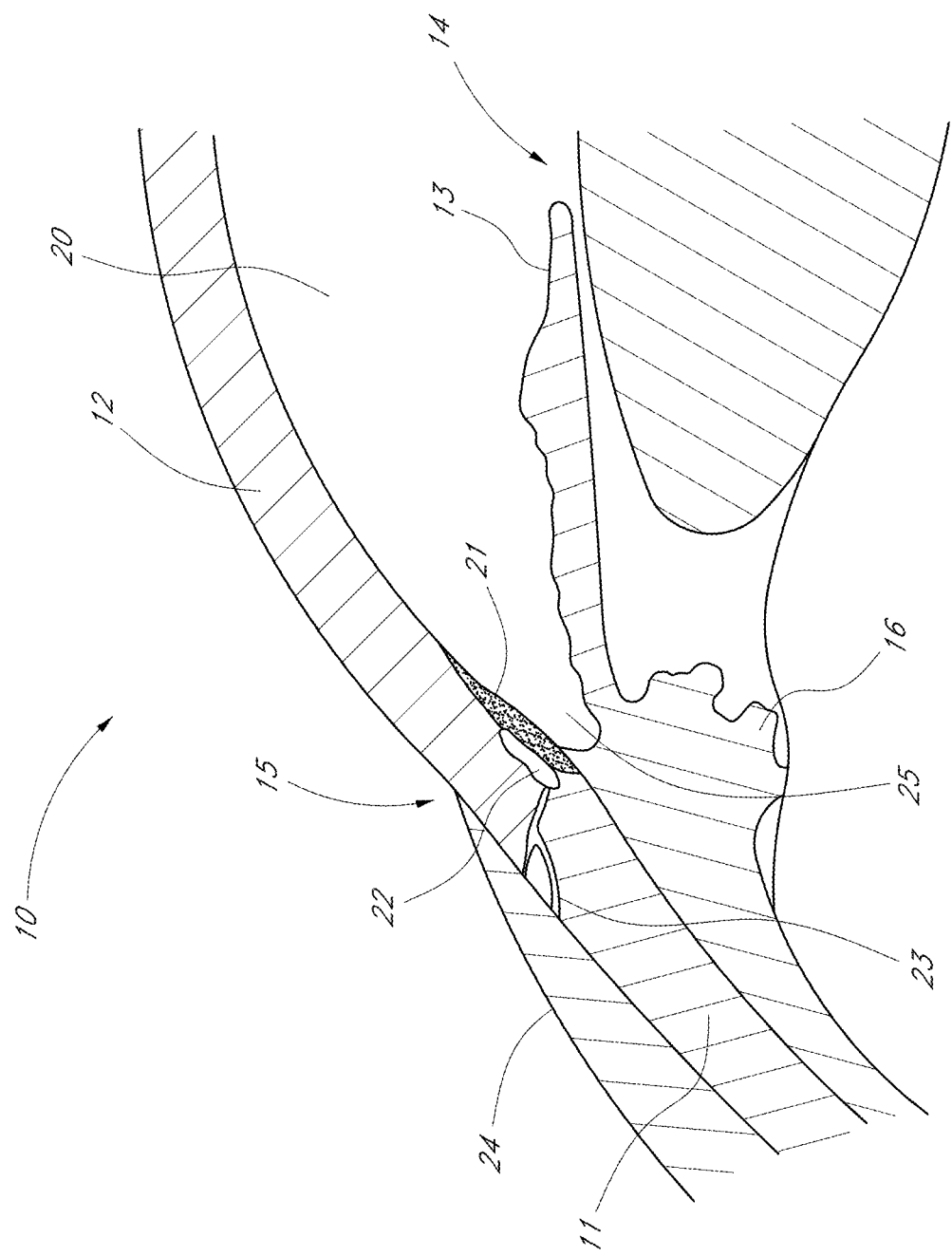
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and a Schlemm's canal 22. A sclera 11 is a thick collagenous tissue which covers the entire eye 10 except a portion which is covered by a cornea 12.

Referring to FIGS. 1 and 2, the cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

Still referring to FIGS. 1 and 2, the anterior chamber 20 of the eye 10, which is bound anteriorly by the cornea 12 and posteriorly by the iris 13 and a lens 26, is filled with aqueous humor (hereinafter referred to as "aqueous"). Aqueous is produced primarily by the ciliary body 16, then moves anteriorly through the pupil 14 and reaches an anterior chamber angle 25, formed between the iris 13 and the cornea 12.

As best illustrated by the drawing of FIG. 2, in a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12.

Self-Trephining Glaucoma Stent

Figure 3:
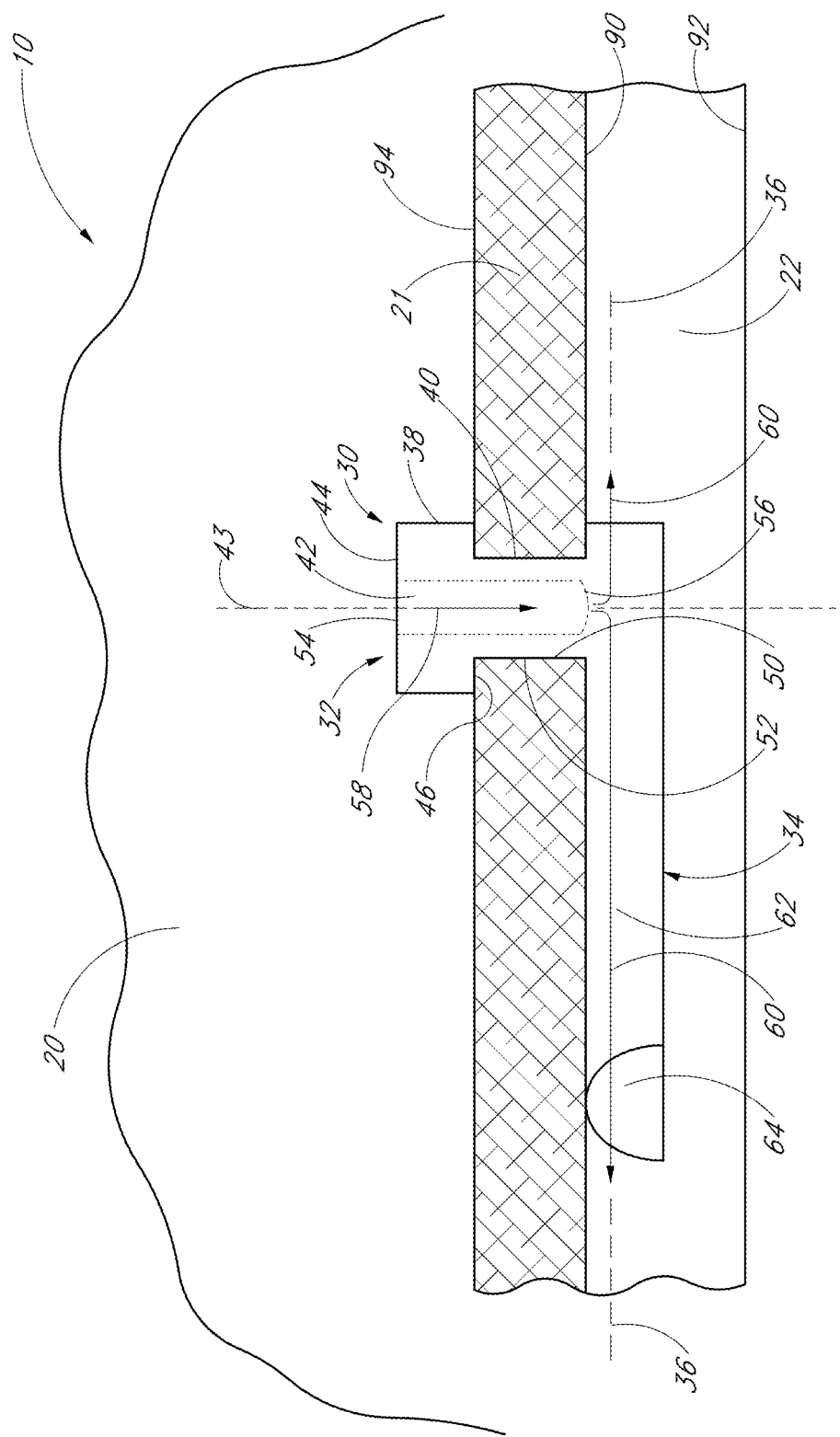
FIG. 3 is a simplified partial view of an eye illustrating the implantation of a glaucoma stent having features and advantages in accordance with one embodiment of the invention.

FIG. 3 generally illustrates the use of one embodiment of a trabecular stenting device 30 for establishing an outflow pathway, passing through the trabecular meshwork 21, which is discussed in greater detail below. FIGS. 4-9 are different views of the stent 30. Advantageously, and as discussed in further detail later herein, the self-trephining-stent allows a one-step procedure to make an incision in the trabecular mesh 21 and place the stent or implant 30 at the desired or predetermined position within the eye 10. Desirably, this facilitates the overall surgical procedure.

In the illustrated embodiment of FIGS. 3-9, the shunt or stent 30 generally comprises a snorkel 32 and a main body portion or blade 34. The snorkel 32 and blade 34 are mechanically connected to or in mechanical communication with one another. The stent 30 and/or the body portion 34 have a generally longitudinal axis 36.

In the illustrated embodiment of FIGS. 3-9, the stent 30 comprises an integral unit. In modified embodiments, the stent 30 may comprise an assembly of individual pieces or components. For example, the stent 30 may comprise an assembly of the snorkel 32 and blade 34.

In the illustrated embodiment of FIGS. 3-9, the snorkel 32 is in the form of a generally elongate tubular member and generally comprises an upper seat, head or cap portion 38, a shank portion 40 and a lumen or passage 42 extending therethrough. The seat 38 is mechanically connected to or in mechanical communication with the shank 40 which is also mechanically connected to or in mechanical communication with the blade 34. The snorkel 32 and/or the lumen 42 have a generally longitudinal axis 43.

In the illustrated embodiment of FIGS. 3-9, the seat 38 is generally circular in shape and has an upper surface 44 and a lower surface 46 which, as shown in FIG. 3, abuts or rests against the trabecular meshwork 21 to stabilize the glaucoma stent 30 within the eye 10. In modified embodiments, the seat 38 may efficaciously be shaped in other suitable manners, as required or desired, giving due consideration to the goals of stabilizing the glaucoma stent 30 within the eye 10 and/or of achieving one or more of the benefits and advantages as taught or suggested herein. For example, the seat 38 may be shaped in other polygonal or non-polygonal shapes and/or comprise one or more ridges which extend radially outwards, among other suitable retention devices.

Figure 10:
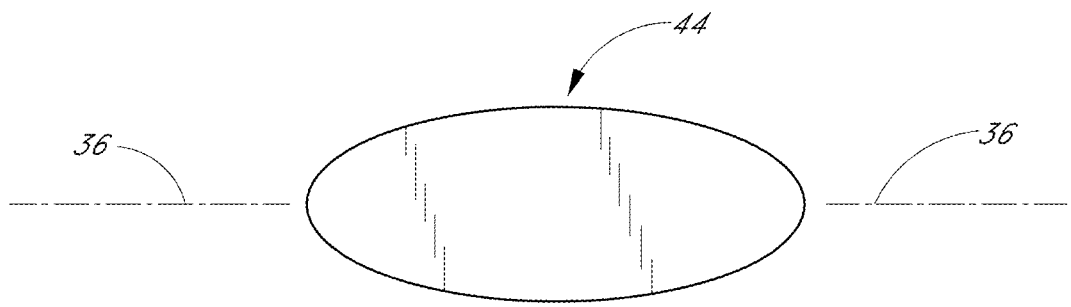
FIG. 10 is a top plan view of one exemplary embodiment of a snorkel top seating surface.
Figure 11:
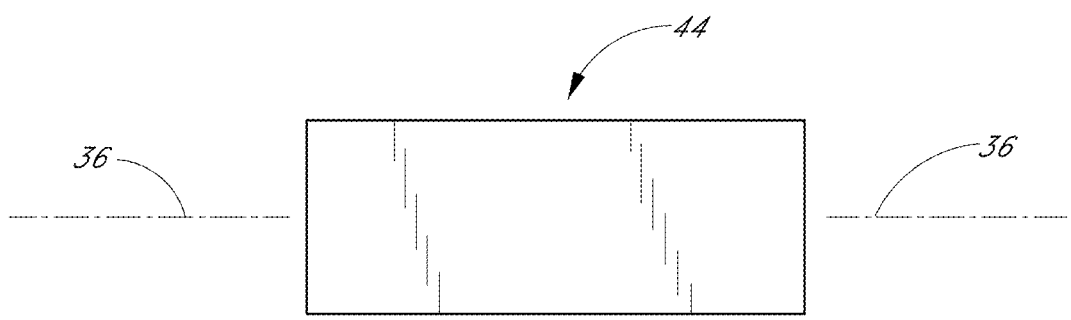
FIG. 11 is a top plan view of another exemplary embodiment of a snorkel top seating surface.
Figure 12:
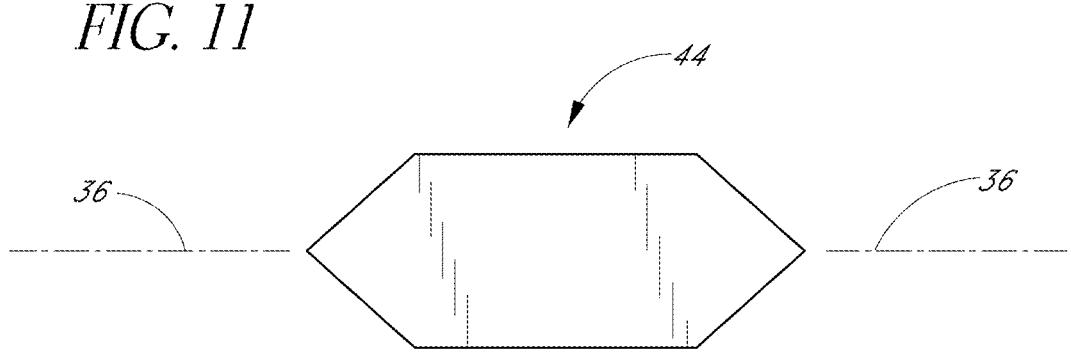
FIG. 12 is a top plan view of yet another exemplary embodiment of a snorkel top seating surface.
Figure 13:
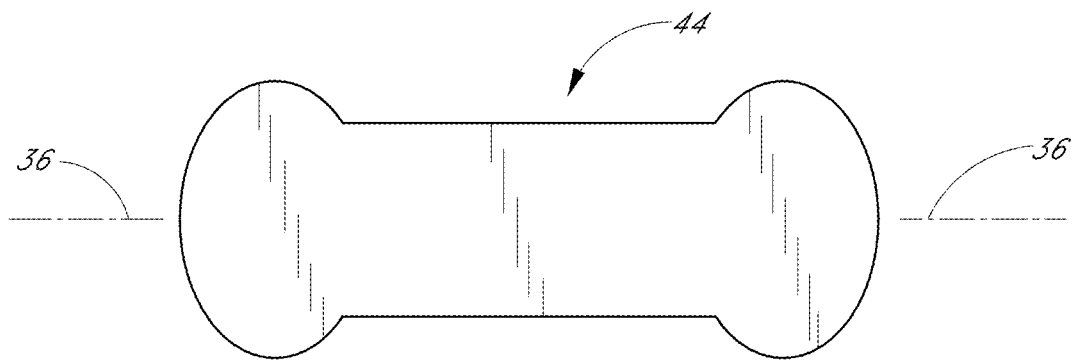
FIG. 13 is a top plan view of still another exemplary embodiment of a snorkel top seating surface.

In the illustrated embodiment of FIGS. 3-9, and as best seen in the top view of FIG. 5, the seat top surface 44 comprises fiducial marks or indicia 48. These marks or indicia 48 facilitate and ensure proper orientation and alignment of the stent 30 when implanted in the eye 10. The marks or indicia 48 may comprise visual differentiation means such as color contrast or be in the form of ribs, grooves, or the like. Alternatively, or in addition, the marks 48 may provide tactile sensory feedback to the surgeon. Also, the seat 38 and/or the seat top surface 44 may be configured in predetermined shapes aligned with the blade 34 and/or longitudinal axis 36 to provide for proper orientation of the stent device 30 within the eye 10. For example, the seat top surface 44 may be oval or ellipsoidal (FIG. 10), rectangular (FIG. 11), hexagonal (FIG. 12), among other suitable shapes (e.g. FIG. 13).

In the illustrated embodiment of FIGS. 3-9, and as indicated above, the seat bottom surface 46 abuts or rests against the trabecular meshwork 21 to stabilize and retain the glaucoma stent 30 within the eye 10. For stabilization purposes, the seat bottom surface 46 may comprise a stubbed surface, a ribbed surface, a surface with pillars, a textured surface, or the like.

In the illustrated embodiment of FIGS. 3-9, the snorkel shank 40 is generally cylindrical in shape. With the stent 30 implanted, as shown in FIG. 3, the shank 40 is generally positioned in an incision or cavity 50 formed in the trabecular meshwork 21 by the self-trephining stent 30. Advantageously, and as discussed further below, this single step of forming the cavity 50 by the stent 30 itself and placing the stent 30 in the desired position facilitates and expedites the overall surgical procedure. In modified embodiments, the snorkel shank 40 may efficaciously be shaped in other suitable manners, as required or desired. For example, the shank 40 may be in the shape of other polygonal or non-polygonal shapes, such as, oval, elliposoidal, and the like.

In the illustrated embodiment of FIGS. 3-9, and as best seen in FIG. 3, the shank 40 has an outer surface 52 in contact with the trabecular meshwork 21 surrounding the cavity 50. For stabilization purposes, the shank outer surface 52 may comprise a stubbed surface, a ribbed surface, a surface with pillars, a textured surface, or the like.

In the illustrated embodiment of FIGS. 3-9, the snorkel lumen 42 has an inlet port, opening or orifice 54 at the seat top surface 44 and an outlet port, opening or orifice 56 at the junction of the shank 40 and blade 34. The lumen 42 is generally cylindrical in shape, that is, it has a generally circular cross-section, and its ports 54, 56 are generally circular in shape. In modified embodiments, the lumen 42 and ports 54, 56 may be efficaciously shaped in other manners, as required or desired, giving due consideration to the goals of providing sufficient aqueous outflow and/or of achieving one or more of the benefits and advantages as taught or suggested herein. For example, the lumen 42 and/or one or both ports 54, 56 may be shaped in the form of ovals, ellipsoids, and the like, or the lumen 42 may have a tapered or stepped configuration.

Referring in particular to FIG. 3, aqueous from the anterior chamber 20 flows into the lumen 42 through the inlet port 54 (as generally indicated by arrow 58) and out of the outlet port 56 and into Schlemm's canal 22 (as generally indicated by arrows 60) to lower and/or balance the intraocular pressure (IOP). In another embodiment, as discussed in further detail below, one or more of the outlet ports may be configured to face in the general direction of the stent longitudinal axis 36. In modified embodiments, the snorkel 32 may comprise more than one lumen, as needed or desired, to facilitate multiple aqueous outflow transportation into Schlemm's canal 22.

In the illustrated embodiment of FIGS. 3-9, the blade longitudinal axis 36 and the snorkel longitudinal axis 43 are generally perpendicular to one another. Stated differently, the projections of the axes 36, 43 on a common plane which is not perpendicular to either of the axes 36, 43 intersect at 90°. The blade longitudinal axis 36 and the snorkel longitudinal axis 43 may intersect one another or may be offset from one another.

In the illustrated embodiment of FIGS. 3-9, the main body portion or blade 34 is a generally curved elongated sheet- or plate-like structure with an upper curved surface 62 and a lower curved surface 64 which defines a trough or open face channel 66. The perimeter of the blade 34 is generally defined by a curved proximal edge 68 proximate to the snorkel 32, a curved distal edge 70 spaced from the proximal edge 68 by a pair of generally straight lateral edges 72, 74 with the first lateral edge 72 extending beyond the second lateral edge 74 and intersecting with the distal edge 70 at a distal-most point 76 of the blade 34 proximate a blade cutting tip 78.

Figure 9:
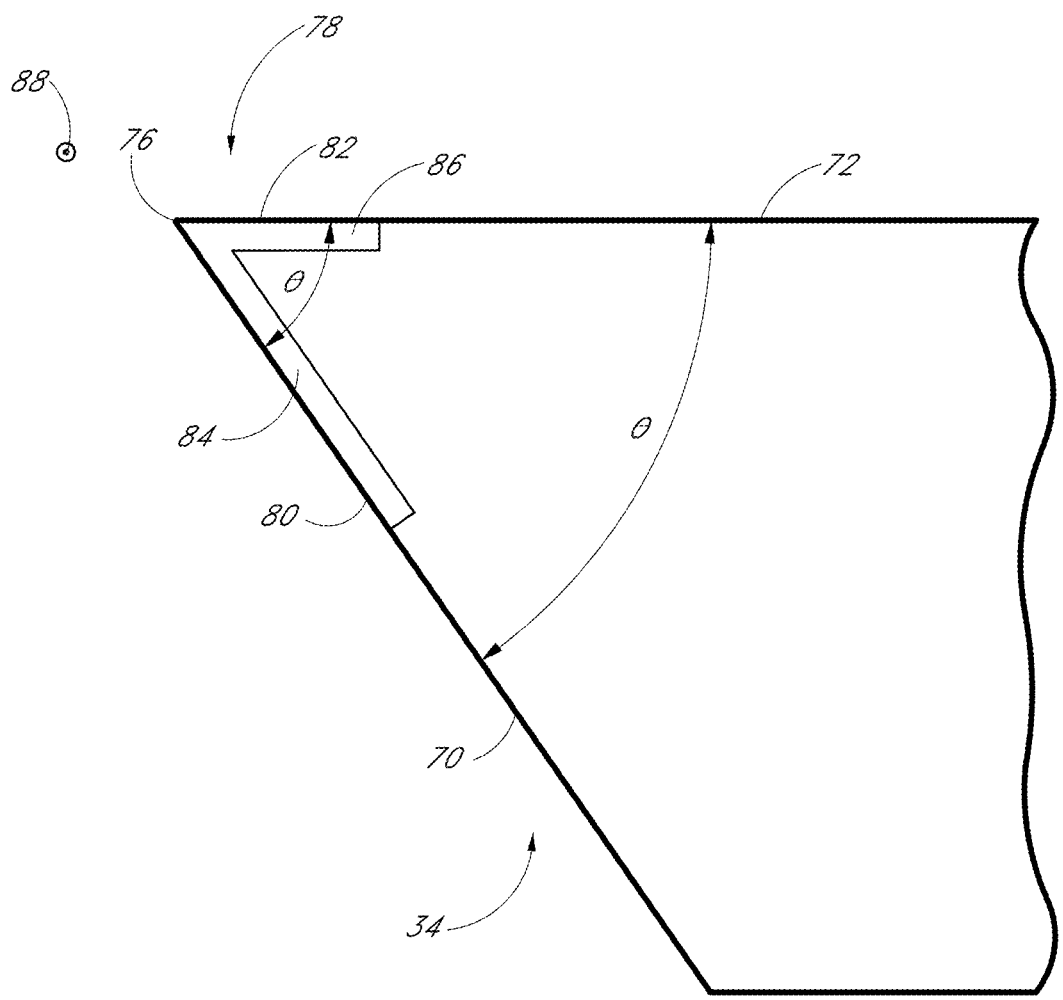
FIG. 9 is an enlarged top plan view of a cutting tip of the stent of FIG. 3.

In the illustrated embodiment of FIGS. 3-9, and as shown in the enlarged view of FIG. 9, the cutting tip 78 comprises a first cutting edge 80 on the distal edge 70 and a second cutting edge 82 on the lateral edge 72. The cutting edges 80, 82 preferably extend from the distal-most point 76 of the blade 34 and comprise at least a respective portion of the distal edge 70 and lateral edge 72. The respective cutting edges 80, 82 are formed at the sharp edges of respective beveled or tapered surfaces 84, 86. In one embodiment, the remainder of the distal edge 70 and lateral edge 72 are dull or rounded. In one embodiment, the tip 78 proximate to the distal-most end 76 is curved slightly inwards, as indicated generally by the arrow 88 in FIG. 5 and arrow 88 (pointed perpendicular and into the plane of the paper) in FIG. 9, relative to the adjacent curvature of the blade 34.

In modified embodiments, suitable cutting edges may be provided on selected portions of one or more selected blade edges 68, 70, 72, 74 with efficacy, as needed or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Referring in particular to FIG. 9, in one embodiment, the ratio between the lengths of the cutting edges 80, 82 is about 2:1. In another embodiment, the ratio between the lengths of the cutting edges 80, 82 is about 1:1. In yet another embodiment, the ratio between the lengths of the cutting edges 80, 82 is about 1:2. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Still referring in particular to FIG. 9, in one embodiment, the ratio between the lengths of the cutting edges 80, 82 is in the range from about 2:1 to about 1:2. In another embodiment, the ratio between the lengths of the cutting edges 80, 82 is in the range from about 5:1 to about 1:5. In yet another embodiment, the ratio between the lengths of the cutting edges 80, 82 is in the range from about 10:1 to about 1:10. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

As shown in the top view of FIG. 9, the cutting edge 80 (and/or the distal end 70) and the cutting edge 82 (and/or the lateral edge 72) intersect at an angle $\theta$. Stated differently, $\theta$ is the angle between the projections of the cutting edge 80 (and/or the distal end 70) and the cutting edge 82 (and/or the lateral edge 72) on a common plane which is not perpendicular to either of these edges.

Referring to in particular to FIG. 9, in one embodiment, the angle $\theta$ is about 50°. In another embodiment, the angle $\theta$ is in the range from about 40° to about 60°. In yet another embodiment, the angle $\theta$ is in the range from about 30° to about 70°. In modified embodiments, the angle $\theta$ may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

The stent 30 of the embodiments disclosed herein can be dimensioned in a wide variety of manners. Referring in particular to FIG. 3, the depth of Schlemm's canal 22 is typically about less than 400 microns (μm). Accordingly, the stunt blade 34 is dimensioned so that the height of the blade 34 (referred to as $H_{41}$ in FIG. 4) is typically less than about 400 μm. The snorkel shank 40 is dimensioned so that it has a length (referred to as $L_{41}$ in FIG. 4) typically in the range from about 100 μm to about 300 μm which is roughly the typical range of the thickness of the trabecular meshwork 21.

Of course, as the skilled artisan will appreciate, that with the stent 30 implanted, the blade 34 may rest at any suitable position within Schlemm's canal 22. For example, the blade 34 may be adjacent to a front wall 90 of Schlemm's canal 22 (as shown in FIG. 3), or adjacent to a back wall 92 of Schlemm's canal 22, or at some intermediate location therebetween, as needed or desired. Also, the snorkel shank 40 may extend into Schlemm's canal 22. The length of the snorkel shank 40 and/or the dimensions of the blade 34 may be efficaciously adjusted to achieve the desired implant positioning.

The trabecular stenting device 30 (FIGS. 3-9) of the exemplary embodiment may be manufactured or fabricated by a wide variety of techniques. These include, without limitation, by molding, thermo-forming, or other micro-machining techniques, among other suitable techniques.

The trabecular stenting device 30 preferably comprises a biocompatible material such that inflammation arising due to irritation between the outer surface of the device 30 and the surrounding tissue is minimized. Biocompatible materials which may be used for the device 30 preferably include, but are not limited to, titanium, titanium alloys, medical grade silicone, e.g., Silastic™, available from Dow Corning Corporation of Midland, Mich.; and polyurethane, e.g., Pellethane™, also available from Dow Corning Corporation.

In other embodiments, the stent device 30 may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

In an exemplary embodiment of the trabecular meshwork surgery, the patient is placed in the supine position, prepped, draped and anesthetized as necessary. In one embodiment, a small (less than about 1 mm) incision, which may be self-sealing is made through the cornea 12. The corneal incision can be made in a number of ways, for example, by using a micro-knife, among other tools.

An applicator or delivery apparatus is used to advance the glaucoma stent 30 through the corneal incision and to the trabecular meshwork 21. Some embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein. Some embodiments of a delivery apparatus are also discussed in further detail later herein. Gonioscopic, microscopic, or endoscopic guidance may be used during the trabecular meshwork surgery.

With the device 30 held by the delivery apparatus, the blade 34 of the self-trephining glaucoma stent device 30 is used to cut and/or displace the material of the trabecular meshwork 21. The snorkel shank 40 may also facilitate in removal of this material during implantation. The delivery apparatus is withdrawn once the device 30 has been implanted in the eye 10. As shown in FIG. 3, once proper implantation has been accomplished the snorkel seat 38 rests on a top surface 94 of the trabecular meshwork 21, the snorkel shank 40 extends through the cavity 50 (created by the device 30) in the trabecular meshwork 21, and the blade extends inside Schlemm's canal 22.

Advantageously, the embodiments of the self-trephining stent device of the invention allow for a "one-step" procedure to make an incision in the trabecular meshwork and to subsequently implant the stent in the proper orientation and alignment within the eye to allow outflow of aqueous from the anterior chamber through the stent and into Schlemm's canal to lower and/or balance the intraocular pressure (IOP). Desirably, this provides for a faster, safer, and less expensive surgical procedure.

Many complications can arise in trabecular meshwork surgeries, wherein a knife is first used to create an incision in the trabecular meshwork, followed by removal of the knife and subsequent installation of the stent. For instance, the knife may cause some bleeding which clouds up the surgical site. This may require more effort and time to clean the surgical site prior to placement of the stent. Moreover, this may cause the intraocular pressure (IOP) to rise. Thus, undesirably, such a multiple step procedure may demand crisis management which slows down the surgery, makes it less safe, and more expensive.

Figure 14:
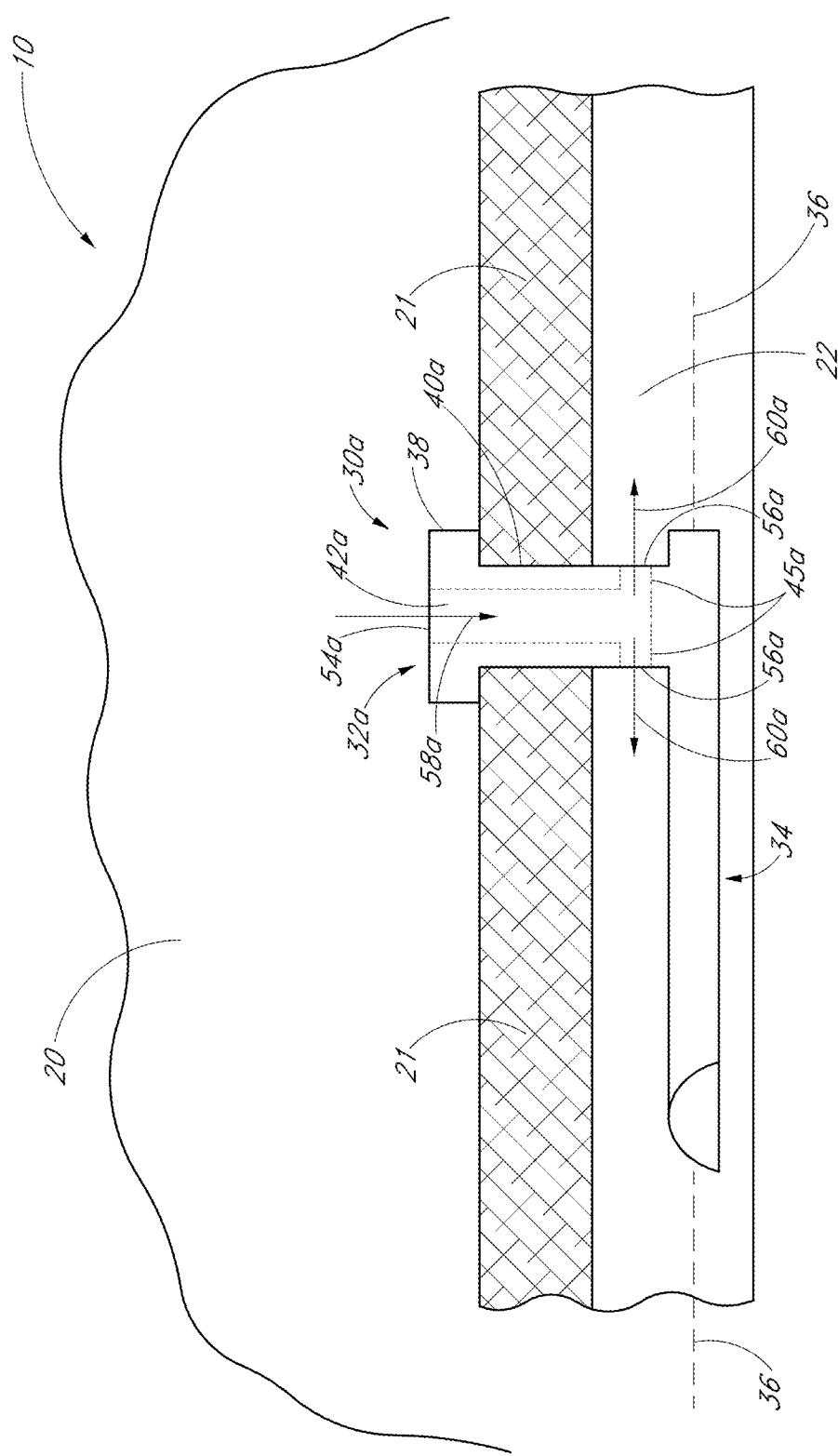
FIG. 14 is a simplified partial view of an eye illustrating the implantation of a glaucoma stent having features and advantages in accordance with another embodiment of the invention.

FIG. 14 is a simplified partial view of an eye 10 illustrating the implantation of a self-trephining glaucoma stent device 30a having features and advantages in accordance with one embodiment. The stent 30a is generally similar to the stent 30 of FIGS. 3-9 except that its snorkel 32a comprises a longer shank 40a which extends into Schlemm's canal 22 and a lumen 42a which bifurcates into two output channels 45a.

In the illustrated embodiment of FIG. 14, the shank 40a terminates at the blade 34. Aqueous flows from the anterior chamber 20 into the lumen 42a through an inlet port 54a (as generally indicated by arrow 58a). Aqueous then flows through the output channels 45a and out of respective outlet ports 56a and into Schlemm's canal 22 (as generally indicated by arrows 60a). The outlet channels 45a extend radially outwards in generally opposed directions and the outlet ports 56a are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45a and respective ports 56a within Schlemm's canal.

In the illustrated embodiment of FIG. 14, two outflow channels 45a are provided. In another embodiment, only one outflow channel 45a is provided. In yet another embodiment, more than two outflow channels 45a are provided. In modified embodiments, the lumen 42a may extend all the way through to the blade 34 and provide an outlet port as discussed above with reference to the embodiment of FIGS. 3-9.

Figure 15:
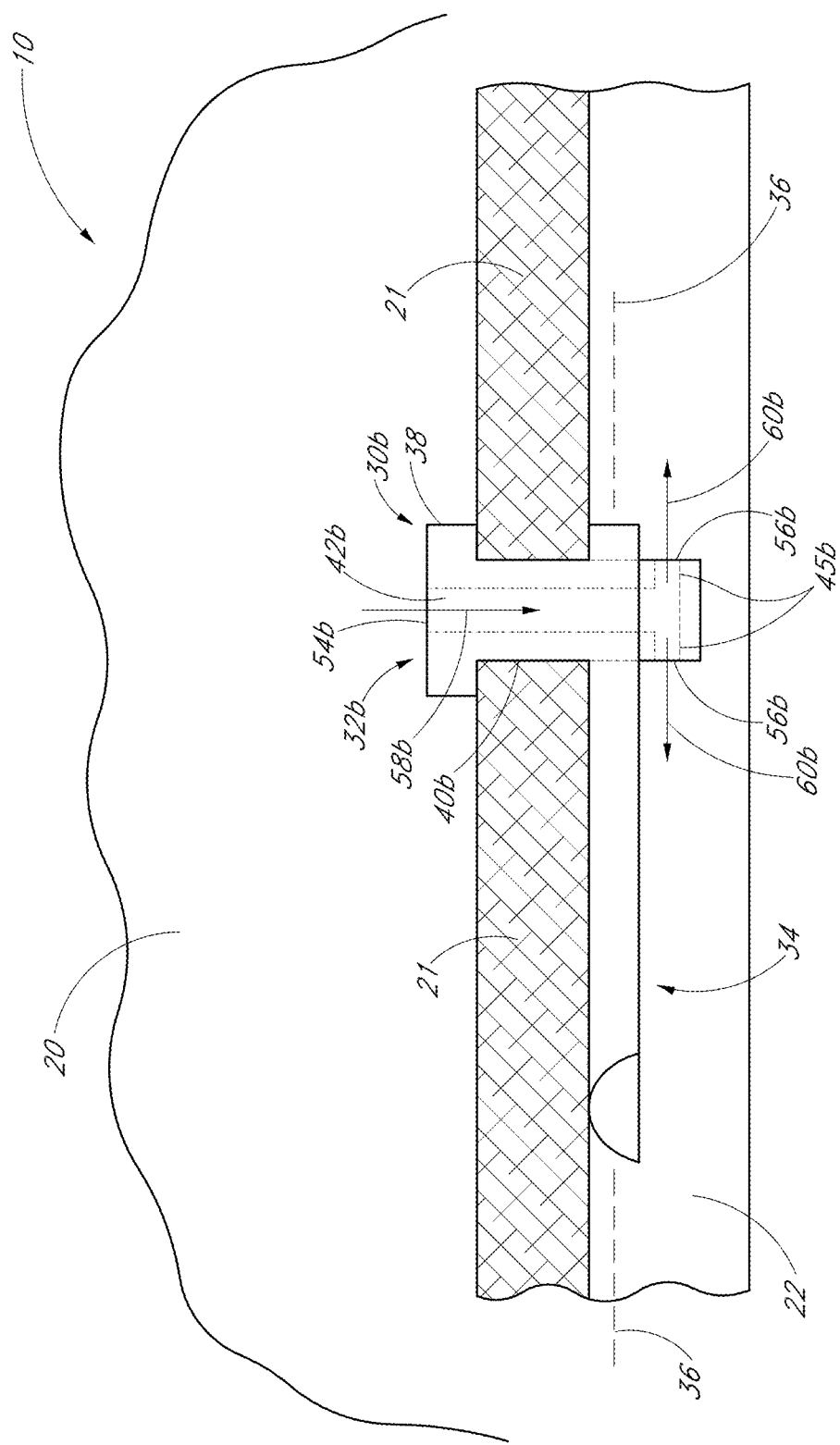
FIG. 15 is a simplified partial view of an eye illustrating the implantation of a glaucoma stent having features and advantages in accordance with a further embodiment of the invention.

FIG. 15 is a simplified partial view of an eye 10 illustrating the implantation of a self-trephining glaucoma stent device 30b having features and advantages in accordance with one embodiment. The stent 30b is generally similar to the stent 30 of FIGS. 3-9 except that its snorkel 32b comprises a longer shank 40b which extends into Schlemm's canal 22 and a lumen 42b which bifurcates into two output channels 45b.

In the illustrated embodiment of FIG. 15, the shank 40b extends through the blade 34. Aqueous flows from the anterior chamber 20 into the lumen 42b through an inlet port 54b (as generally indicated by arrow 58b). Aqueous then flows through the output channels 45b and out of respective outlet ports 56b and into Schlemm's canal 22 (as generally indicated by arrows 60b). The outlet channels 45b extend radially outwards in generally opposed directions and the outlet ports 56b are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45b and respective ports 56b within Schlemm's canal.

In the illustrated embodiment of FIG. 15, two outflow channels 45b are provided. In another embodiment, only one outflow channel 45b is provided. In yet another embodiment, more than two outflow channels 45b are provided. In modified embodiments, the lumen 42b may extend all the way through to the blade 34 and provide an outlet port as discussed above with reference to the embodiment of FIGS. 3-9.

FIGS. 16-20 show different views of a self-trephining glaucoma stent device 30c having features and advantages in accordance with one embodiment. The stent 30c is generally similar to the stent 30 of FIGS. 3-9 except that it has a modified blade configuration. The stent 30c comprises a blade 34c which is a generally curved elongated sheet- or plate-like structure with an upper curved surface 62c and a lower curved surface 64c which defines a trough or open face channel 66c. The perimeter of the blade 34c is generally defined by a curved proximal edge 68c proximate to the snorkel 32, a curved distal edge 70c spaced from the proximal edge 68c by a pair of generally straight lateral edges 72c, 74c which are generally parallel to one another and have about the same length.

In the illustrated embodiment of FIGS. 16-20, the blade 34c comprises a cutting tip 78c. The cutting tip 78c preferably includes cutting edges formed on selected portions of the distal edge 70c and adjacent portions of the lateral edges 72c, 74c for cutting through the trabecular meshwork for placement of the snorkel 32. The cutting edges are sharp edges of beveled or tapered surfaces as discussed above in reference to FIG. 9. The embodiment of FIGS. 16-20 may be efficaciously modified to incorporate the snorkel configuration of the embodiments of FIGS. 14 and 15.

FIGS. 21-25 show different views of a self-trephining glaucoma stent device 30d having features and advantages in accordance with one embodiment. The stent 30d is generally similar to the stent 30 of FIGS. 3-9 except that it has a modified blade configuration. The stent 30d comprises a blade 34d which is a generally curved elongated sheet- or plate-like structure with an upper curved surface 62d and a lower curved surface 64d which defines a trough or open face channel 66d. The perimeter of the blade 34d is generally defined by a curved proximal edge 68d proximate to the snorkel 32, a pair of inwardly converging curved distal edges 70d', 70d'' spaced from the proximal edge 68d by a pair of generally straight respective lateral edges 72d, 74d which are generally parallel to one another and have about the same length. The distal edges 70d', 70d'' intersect at a distal-most point 76d of the blade 34d proximate a blade cutting tip 78d.

In the illustrated embodiment of FIGS. 21-25, the cutting tip 78d preferably includes cutting edges formed on the distal edges 70d', 70d'' and extending from the distal-most point 76d of the blade 34d. In one embodiment, the cutting edges extend along only a portion of respective distal edges 70d', 70d''. In another embodiment, the cutting edges extend along substantially the entire length of respective distal edges 70d', 70d''. In yet another embodiment, at least portions of the lateral edges 72d, 74d proximate to respective distal edges 70d', 70d'' have cutting edges. In a further embodiment, the tip 78d proximate to the distal-most end 76d is curved slightly inwards, as indicated generally by the arrow 88d in FIG. 21 and arrow 88d (pointed perpendicular and into the plane of the paper) in FIG. 22, relative to the adjacent curvature of the blade 34d.

In the embodiment of FIGS. 21-25, the cutting edges are sharp edges of beveled or tapered surfaces as discussed above in reference to FIG. 9. The embodiment of FIGS. 21-25 may be efficaciously modified to incorporate the snorkel configuration of the embodiments of FIGS. 14 and 15.

Figure 28:
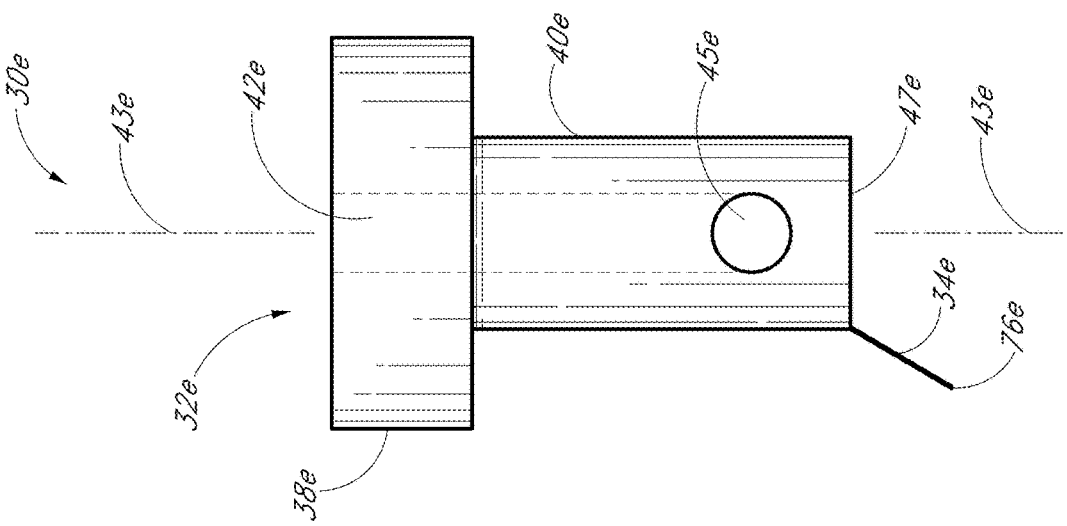
FIG. 28 is a rear end view along line 28-28 of FIG. 26.
Figure 26:
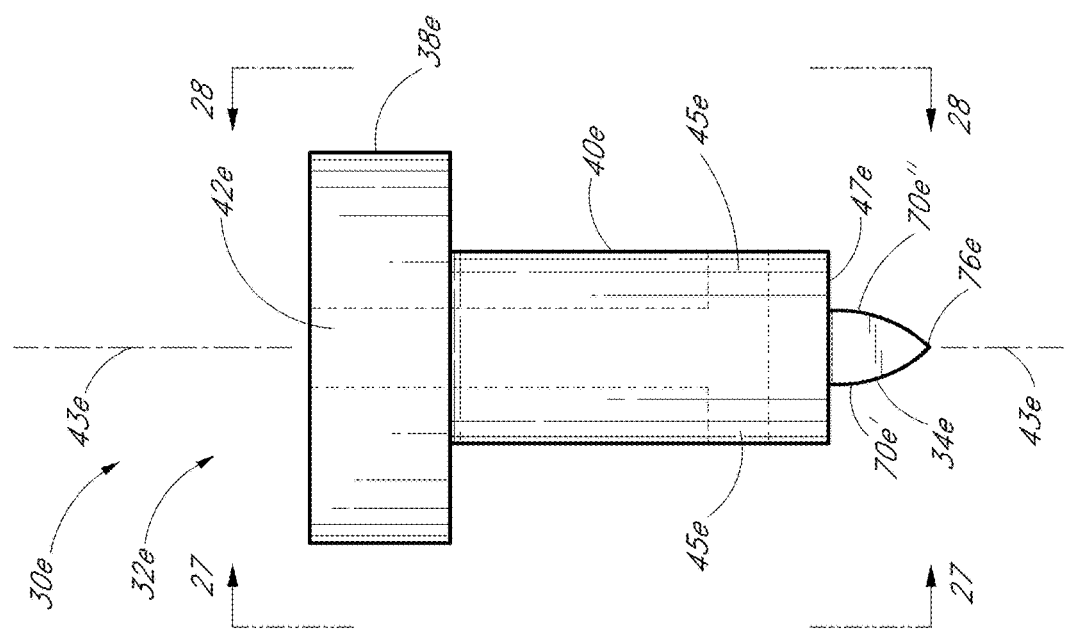
FIG. 26 is a front elevation view of a glaucoma stent having features and advantages in accordance with one embodiment of the invention.
Figure 27:
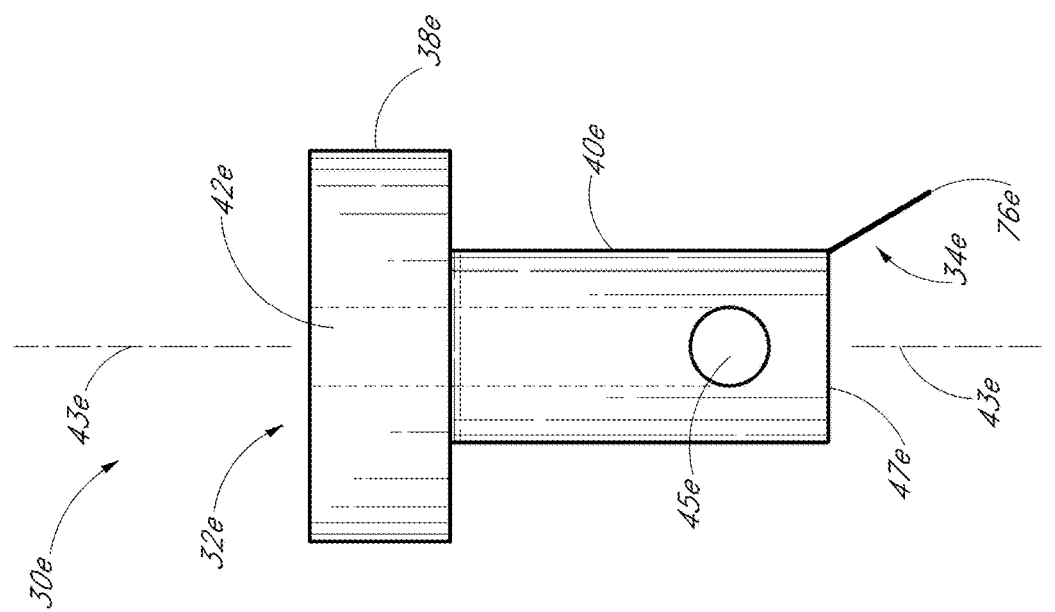
FIG. 27 is a side elevation view along line 27-27 of FIG. 26.

FIGS. 26-28 show different views of a self-trephining glaucoma stent device 30e having features and advantages in accordance with one embodiment. The stent device 30e generally comprises a snorkel 32e mechanically connected to or in mechanical communication with a blade or cutting tip 34e. The snorkel 32e has a seat, head or cap portion 38e mechanically connected to or in mechanical communication with a shank 40e, as discussed above. The shank 40e has a distal end or base 47e. The snorkel 32e further has a lumen 42e which bifurcates into a pair of outlet channels 45e, as discussed above in connection with FIGS. 14 and 15. Other lumen and inlet and outlet port configurations as taught or suggested herein may also be efficaciously used, as needed or desired.

In the illustrated embodiment of FIGS. 26-28, the blade 34e extends downwardly and outwardly from the shank distal end 47e. The blade 34e is angled relative to a generally longitudinal axis 43e of the snorkel 32e, as best seen in FIGS. 27 and 28. The blade 34e has a distal-most point 76e. The blade or cutting tip 34e has a pair of side edges 70e', 70e'', including cutting edges, terminating at the distal-most point 76e, as best seen in FIG. 26. In one embodiment, the cutting edges are sharp edges of beveled or tapered surfaces as discussed above in reference to FIG. 9.

Referring to FIGS. 26-28, in one embodiment, the blade 34e includes cutting edges formed on the edges 70e', 70e'' and extending from the distal-most point 76e of the blade 34d. In one embodiment, the cutting edges extend along only a portion of respective distal edges 70e', 70e''. In another embodiment, the cutting edges extend along substantially the entire length of respective distal edges 70e', 70e''. In yet another embodiment, the blade or cutting tip 34e comprises a bent tip of needle, for example, a 30 gauge needle.

In general, any of the blade configurations disclosed herein may be used in conjunction with any of the snorkel configurations disclosed herein or incorporated by reference herein to provide a self-trephining glaucoma stent device for making an incision in the trabecular meshwork for receiving the corresponding snorkel to provide a pathway for aqueous outflow from the eye anterior chamber to Schlemm's canal, thereby effectively lowering and/or balancing the intraocular pressure (IOP). The self-trephining ability of the device, advantageously, allows for a "one-step" procedure in which the incision and placement of the snorkel are accomplished by a single device and operation. In any of the embodiments, fiducial markings or indicia, and/or preselected configuration of the snorkel seat, and/or positioning of the stent device in a preloaded applicator may be used for proper orientation and alignment of the device during implantation.

Delivery Apparatus

Figure 29:
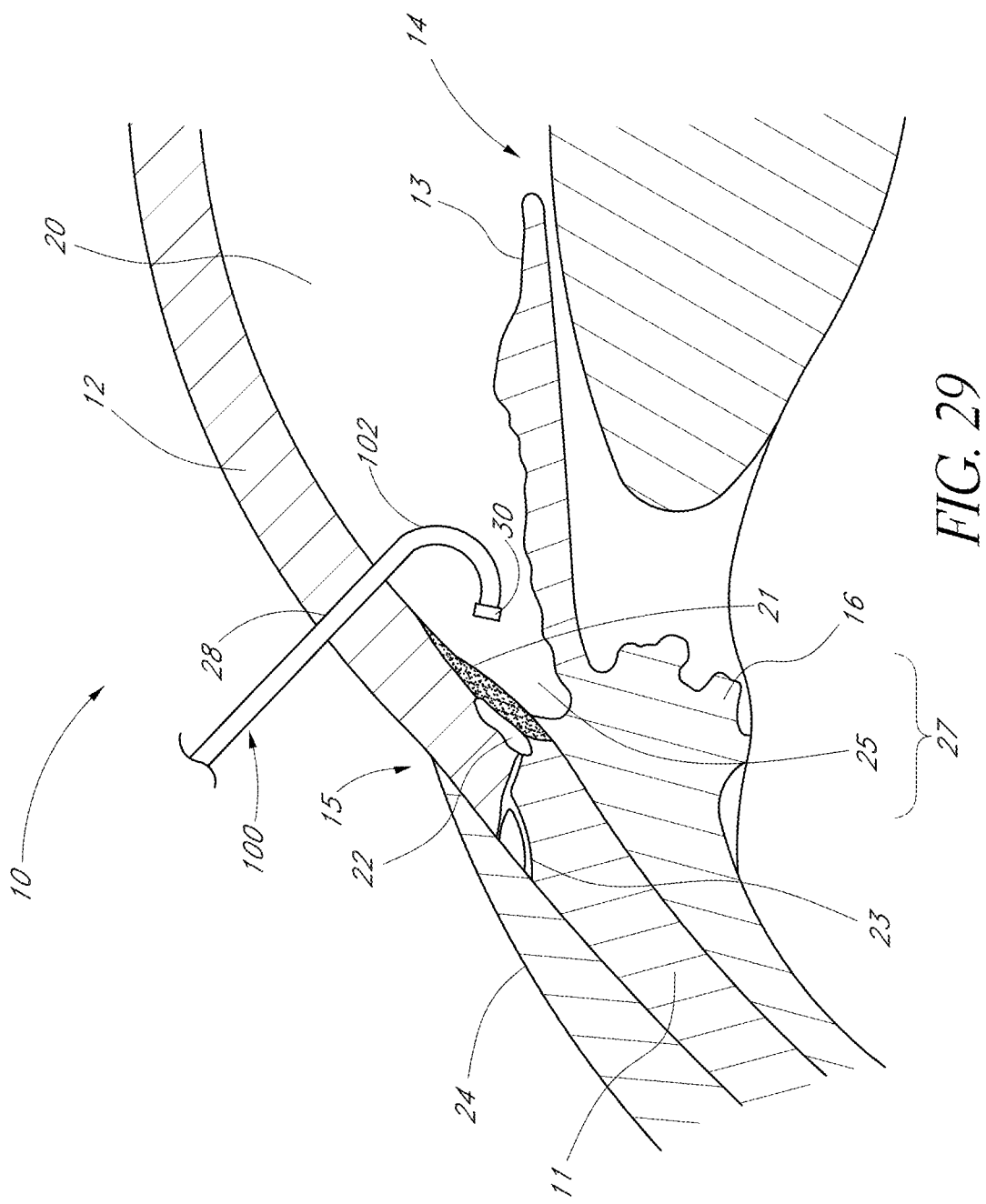
FIG. 29 is a simplified partial view of an eye illustrating the temporal implantation of a glaucoma stent using a delivery apparatus having features and advantages in accordance with one embodiment of the invention.

In many cases, a surgeon works from a temporal incision when performing cataract or goniometry surgery. FIG. 29 illustrates a temporal implant procedure, wherein a delivery apparatus or "applicator" 100 having a curved tip 102 is used to deliver a stent 30 to a temporal side 27 of the eye 10. An incision 28 is made in the cornea 10, as discussed above. The apparatus 100 is then used to introduce the stent 30 through the incision 28 and implant it within the eye 10.

Still referring in particular to FIG. 29, in one embodiment, a similarly curved instrument would be used to make the incision through the trabecular meshwork 21. In other embodiments, a self-trephining stent device 30 may be used to make this incision through the trabecular meshwork 21, as discussed above. The temporal implantation procedure illustrated in FIG. 29 may be employed with the any of the various stent embodiments taught or suggested herein.

Figure 30:
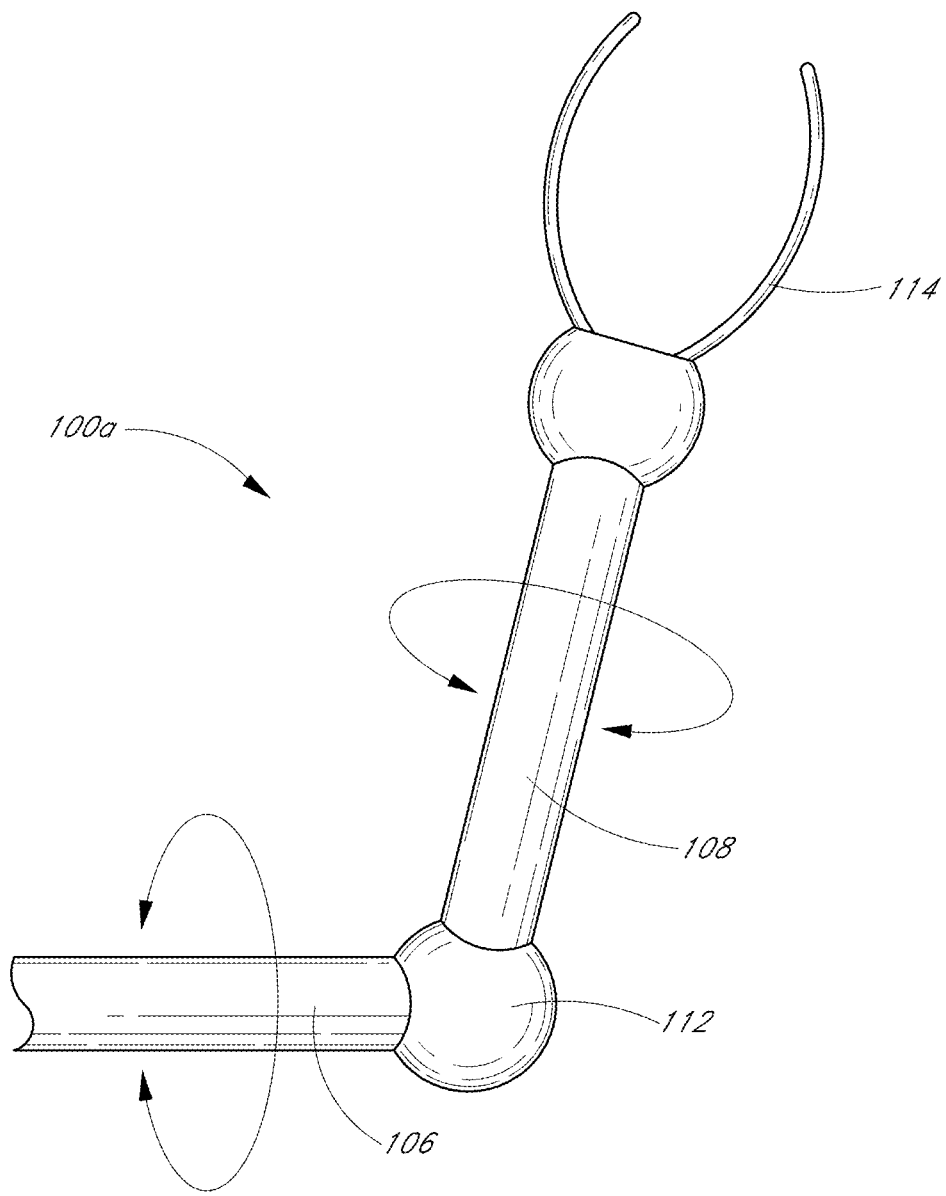
FIG. 30 is an oblique elevational view of an articulating arm stent delivery/retrieval apparatus having features and advantages in accordance with one embodiment of the invention.

FIG. 30 illustrates one embodiment of an apparatus comprising an articulating stent applicator or retrieval device 100a. In this embodiment, a proximal arm 106 is attached to a distal arm 108 at a joint 112. This joint 112 is movable such that an angle formed between the proximal arm 106 and the distal arm 108 can change. One or more claws 114 can extend from the distal arm 108, in the case of a stent retrieval device. Similarly, this articulation mechanism may be used for the trabecular stent applicator, and thus the articulating applicator or retrieval device 100a may be either an applicator for the trabecular stent, a retrieval device, or both, in various embodiments. The embodiment of FIG. 30 may be employed with the any of the various stent embodiments taught or suggested herein.

Figure 31:
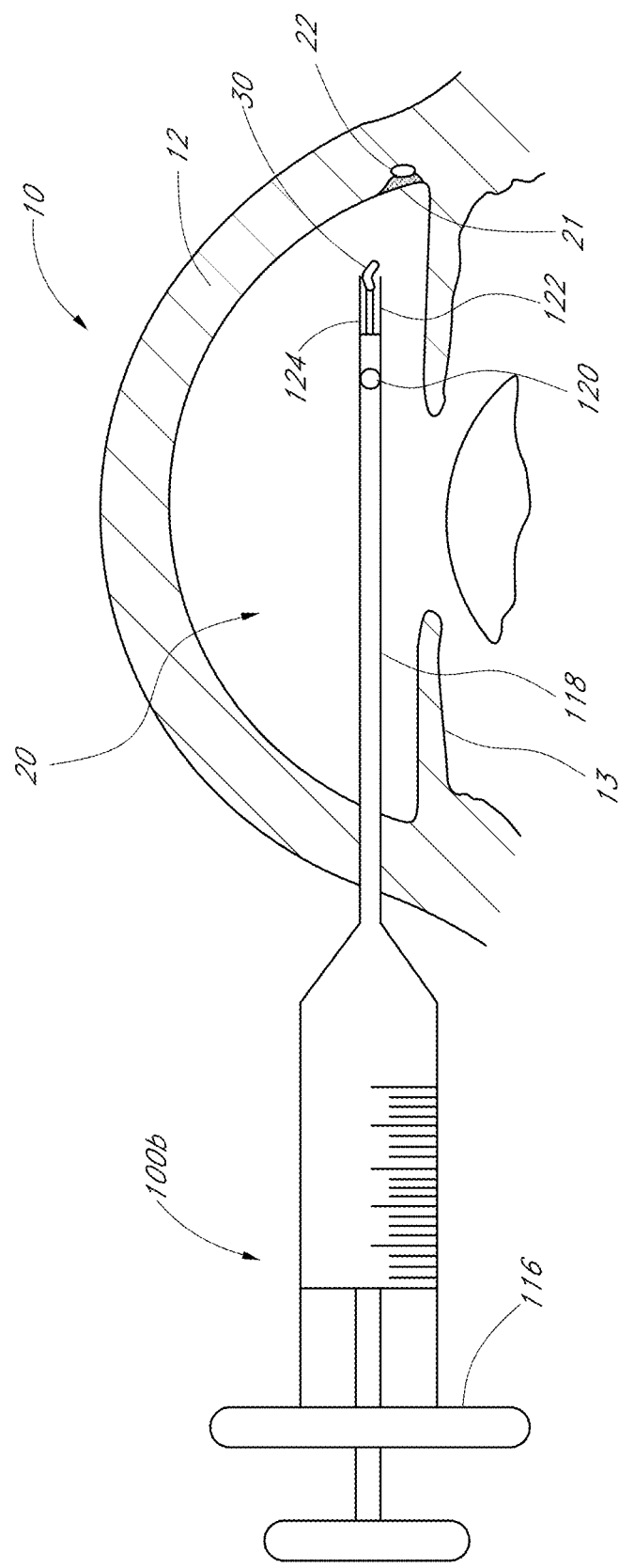
FIG. 31 is a simplified partial view of an eye illustrating the implantation of a glaucoma stent using a delivery apparatus crossing through the eye anterior chamber.

FIG. 31 shows another illustrative method for placing any of the various stent embodiments taught or suggested herein at the implant site within the eye 10. A delivery apparatus 100b generally comprises a syringe portion 116 and a cannula portion 118. The distal section of the cannula 118 has at least one irrigating hole 120 and a distal space 122 for holding the stent device 30. The proximal end 124 of the lumen of the distal space 122 is sealed from the remaining lumen of the cannula portion 118. The delivery apparatus of FIG. 30 may be employed with the any of the various stent embodiments taught or suggested herein.

In one aspect of the invention, a delivery apparatus (or "applicator") is used for placing a trabecular stent through a trabecular meshwork of an eye. Certain embodiments of such a delivery apparatus are disclosed in U.S. application Ser. No. 10/101,548, filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the stent is being held by the holder, the spring being at least partially unloaded upon actuating the actuator, allowing for release of the stent from the holder.

In various embodiments, the clamp comprises a plurality of claws configured to exert a clamping force onto the inlet section of the stent. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece.

The delivery apparatus can further comprise an irrigation port in the elongate tip.

Some aspects include a method of placing a trabecular stent through a trabecular meshwork of an eye, the stent having an inlet section and an outlet section, including advancing a delivery apparatus holding the trabecular stent through an anterior chamber of the eye and into the trabecular meshwork, placing part of the stent through the trabecular meshwork and into a Schlemm's canal of the eye; and releasing the stent from the delivery apparatus.

In various embodiments, the method includes using a delivery apparatus that comprises a handpiece having a distal end and a proximal end; an elongate tip connected to the distal end of the handpiece, the elongate tip having a distal portion and being configured to be placed through a corneal incision and into an anterior chamber of the eye; a holder attached to the distal portion of the elongate tip, the holder configured to hold and release the inlet section of the trabecular stent; and an actuator on the handpiece that actuates the holder to release the inlet section of the trabecular stent from the holder.

In one aspect, the trabecular stent is removably attached to a delivery apparatus (also known as "applicator"). When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger. In some embodiments, the delivery applicator may be a guidewire, an expandable basket, an inflatable balloon, or the like.

Other Embodiments

Figure 32:
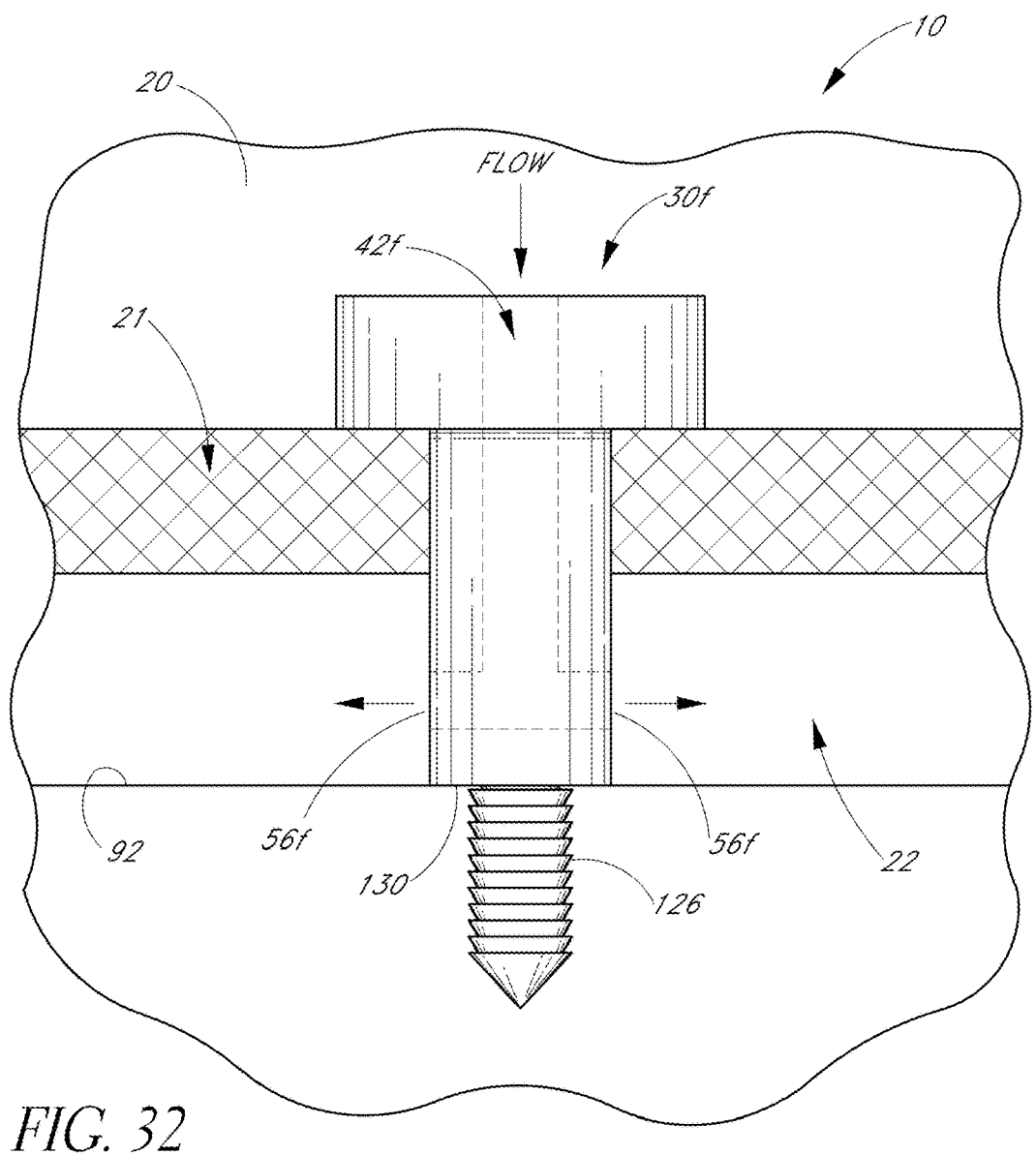
FIG. 32 is a simplified partial view of an eye illustrating the implantation of a glaucoma stent having features and advantages in accordance with one embodiment of the invention.
Figure 33:
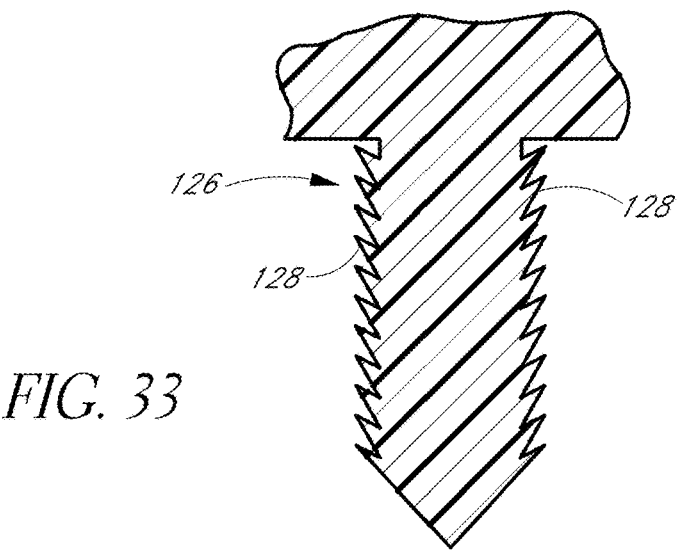
FIG. 33 is a detailed enlarged view of the barbed pin of FIG. 32.

Screw/Barb Anchored Stent:

FIGS. 32 and 33 illustrate a glaucoma stent device 30f having features and advantages in accordance with one embodiment. This embodiment of the trabecular stent 30f includes a barbed or threaded screw-like extension or pin 126 with barbs 128 for anchoring. The barbed pin 126 extends from a distal or base portion 130 of the stent 30f.

In use, the stent 30f (FIG. 32) is advanced through the trabecular meshwork 21 and across Schlemm's canal 22. The barbed (or threaded) extension 126 penetrates into the back wall 92 of Schlemm's canal 22 up to the shoulder or base 130 that then rests on the back wall 92 of the canal 22. The combination of a shoulder 130 and a barbed pin 126 of a particular length limits the penetration depth of the barbed pin 126 to a predetermined or preselected distance. In one embodiment, the length of the pin 126 is about 0.5 mm or less. Advantageously, this barbed configuration provides a secure anchoring of the stent 30f. As discussed above, correct orientation of the stent 30f is ensured by appropriate fiducial marks, indicia or the like and by positioning of the stent in a preloaded applicator.

Referring to FIG. 32, the aqueous flows from the anterior chamber 20, through the lumen 42f, then out through two side-ports 56f to be directed in both directions along Schlemm's canal 22. Alternatively, flow could be directed in only one direction through a single side-port 56f. In other embodiments, more than two outlet ports 56f, for example, six to eight ports (like a pin wheel configuration), may be efficaciously used, as needed or desired.

Still referring to FIG. 32, in one embodiment, the stent 30f is inserted through a previously made incision in the trabecular meshwork 21. In other embodiments, the stent 30f may be combined with any of the blade configurations taught or suggested herein to provide self-trephining capability. In these cases, the incision through the trabecular meshwork 21 is made by the self-trephining stent device which has a blade at its base or proximate to the base.

Figure 34:
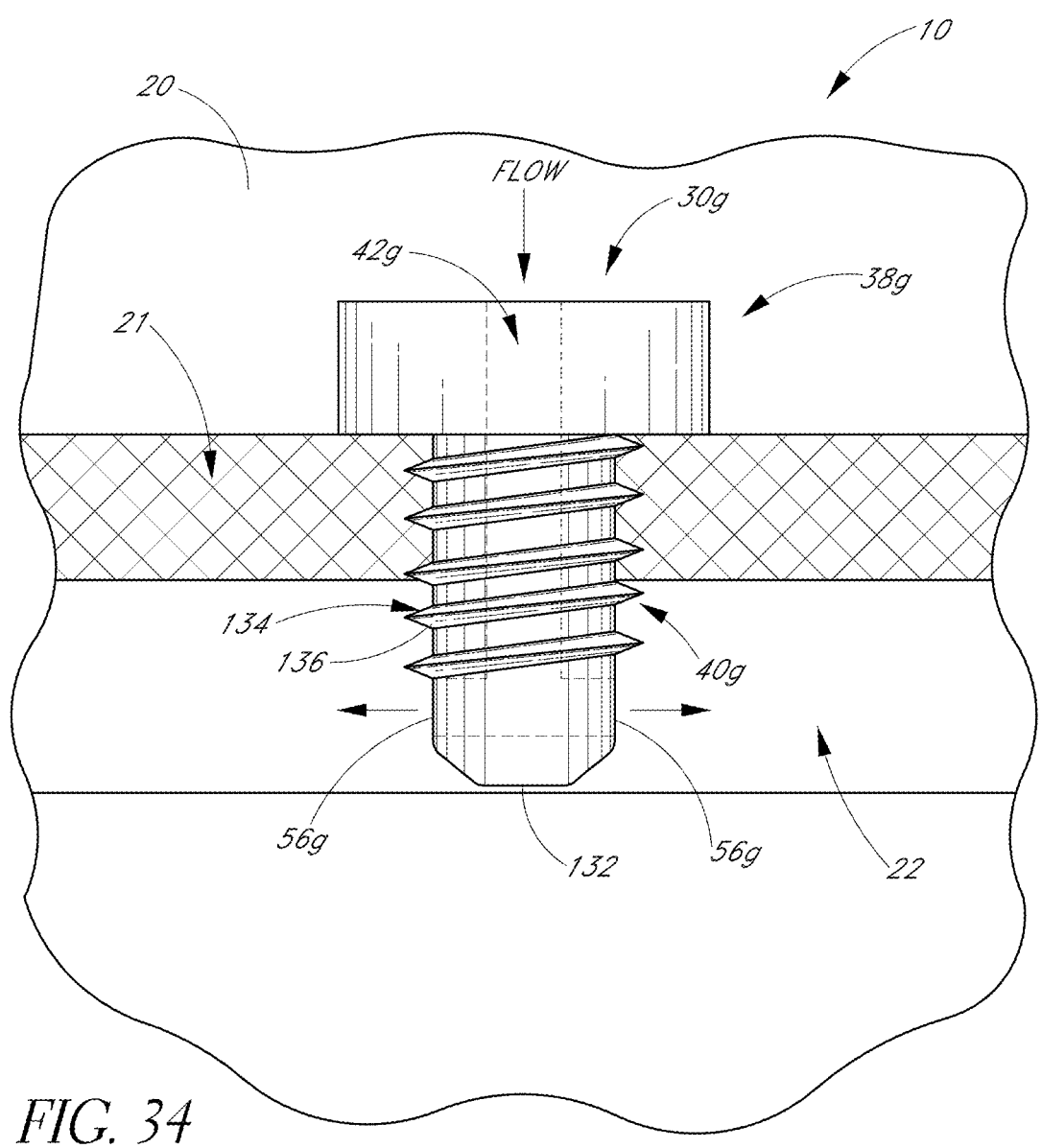
FIG. 34 is a simplified partial view of an eye illustrating the implantation of a glaucoma stent having features and advantages in accordance with one embodiment of the invention.

Deeply Threaded Stent:

FIG. 34 illustrates a glaucoma stent device 30g having features and advantages in accordance with one embodiment. The stent 30g has a head or seat 38g and a shank or main body portion 40g with a base or distal end 132. This embodiment of the trabecular stent 30g includes a deep thread 134 (with threads 136) on the main body 40g of the stent 30g below the head 38g. The threads may or may not extend all the way to the base 132.

In use, the stent 30g (FIG. 34) is advanced through the meshwork 21 through a rotating motion, as with a conventional screw. Advantageously, the deep threads 136 provide retention and stabilization of the stent 30g in the trabecular meshwork 21.

Referring to FIG. 34, the aqueous flows from the anterior chamber 20, through the lumen 42g, then out through two side-ports 56g to be directed in both directions along Schlemm's canal 22. Alternatively, flow could be directed in only one direction through a single side-port 56g. In other embodiments, more than two outlet ports 56g may be efficaciously used, as needed or desired.

One suitable applicator or delivery apparatus for this stent 30g (FIG. 34) includes a preset rotation, for example, via a wound torsion spring or the like. The rotation is initiated by a release trigger on the applicator. A final twist of the applicator by the surgeon and observation of suitable fiducial marks, indicia or the like ensure proper alignment of the side ports 56g with Schlemm's canal 22.

Referring to FIG. 34, in one embodiment, the stent 30g is inserted through a previously made incision in the trabecular meshwork 21. In other embodiments, the stent 30g may be combined with any of the blade configurations taught or suggested herein to provide self-trephining capability. In these cases, the incision through the trabecular meshwork 21 is made by the self-trephining stent device which has a blade at its base or proximate to the base.

Figure 35:
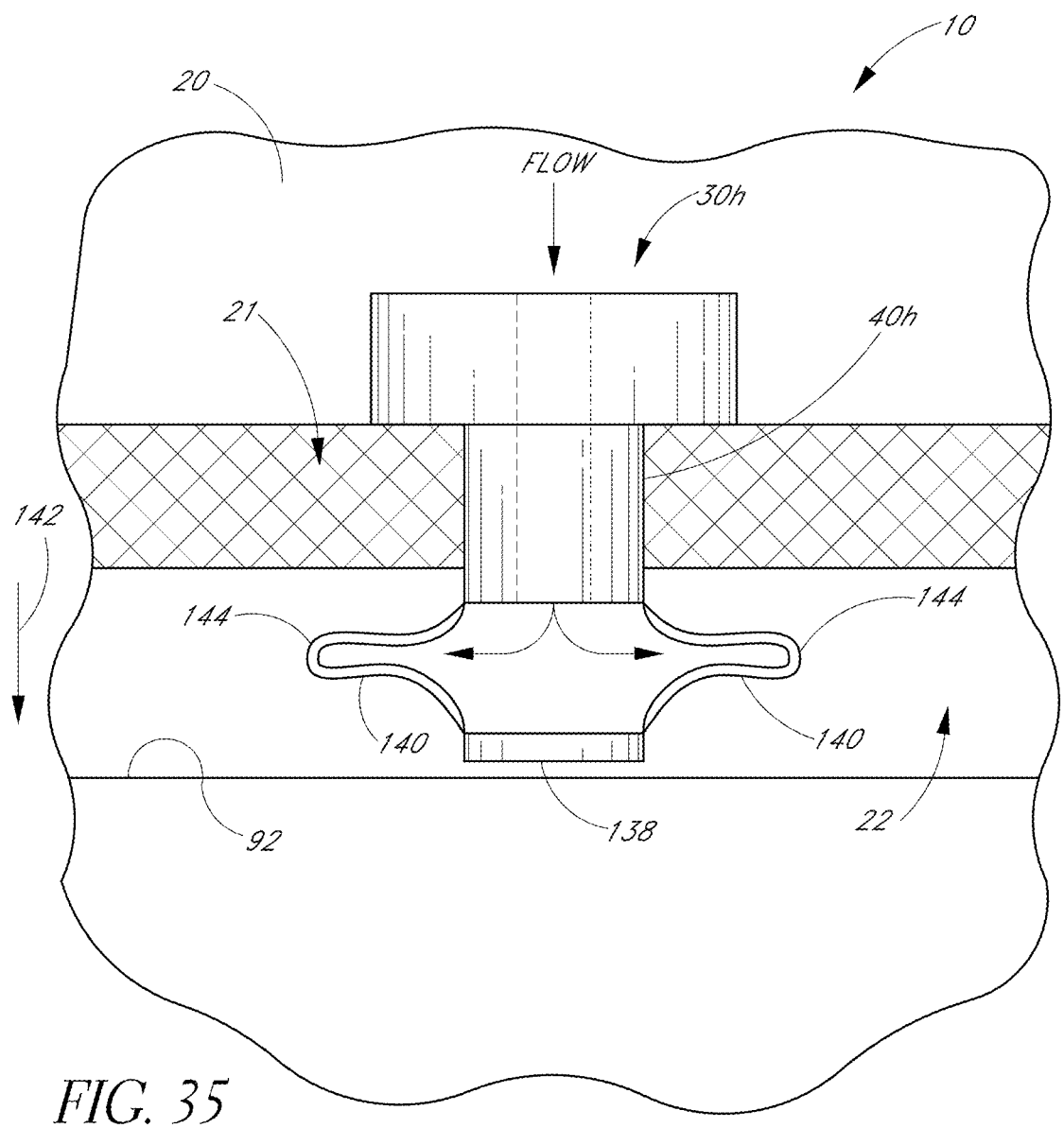
FIG. 35 is a simplified partial view of an eye illustrating the implantation of a glaucoma stent having features and advantages in accordance with one embodiment of the invention.

Rivet Style Stent:

FIG. 35 illustrates a glaucoma stent device 30h having features and advantages in accordance with one embodiment. The stent has a base or distal end 138. This embodiment of the trabecular stent 30h has a pair of flexible ribs 140. In the unused state, the ribs are initially generally straight (that is, extend in the general direction of arrow 142).

Referring to FIG. 35, upon insertion of the stent 30h through the trabecular meshwork 21, the ends 144 of respective ribs 140 of the stent 30h come to rest on the back wall 92 of Schlemm's canal 22. Further advancement of the stent 30h causes the ribs 140 to deform to the bent shape as shown in the drawing of FIG. 35. The ribs 140 are designed to first buckle near the base 138 of the stent 30h. Then the buckling point moves up the ribs 140 as the shank part 40h of the stent 30h is further advanced through the trabecular meshwork 21.

The lumen 42h (FIG. 35) in the stent 30h is a simple straight hole. The aqueous flows from the anterior chamber 20, through the lumen 42h, then out around the ribs 140 to the collector channels further along Schlemm's canal 22 in either direction.

Referring to FIG. 35, in one embodiment, the stent 30h is inserted through a previously made incision in the trabecular meshwork 21. In other embodiments, the stent 30h may be combined with any of the blade configurations taught or suggested herein to provide self-trephining capability. In these cases, the incision through the trabecular meshwork 21 is made by the self-trephining stent device which has a blade at its base or proximate to the base.

Figure 36A:
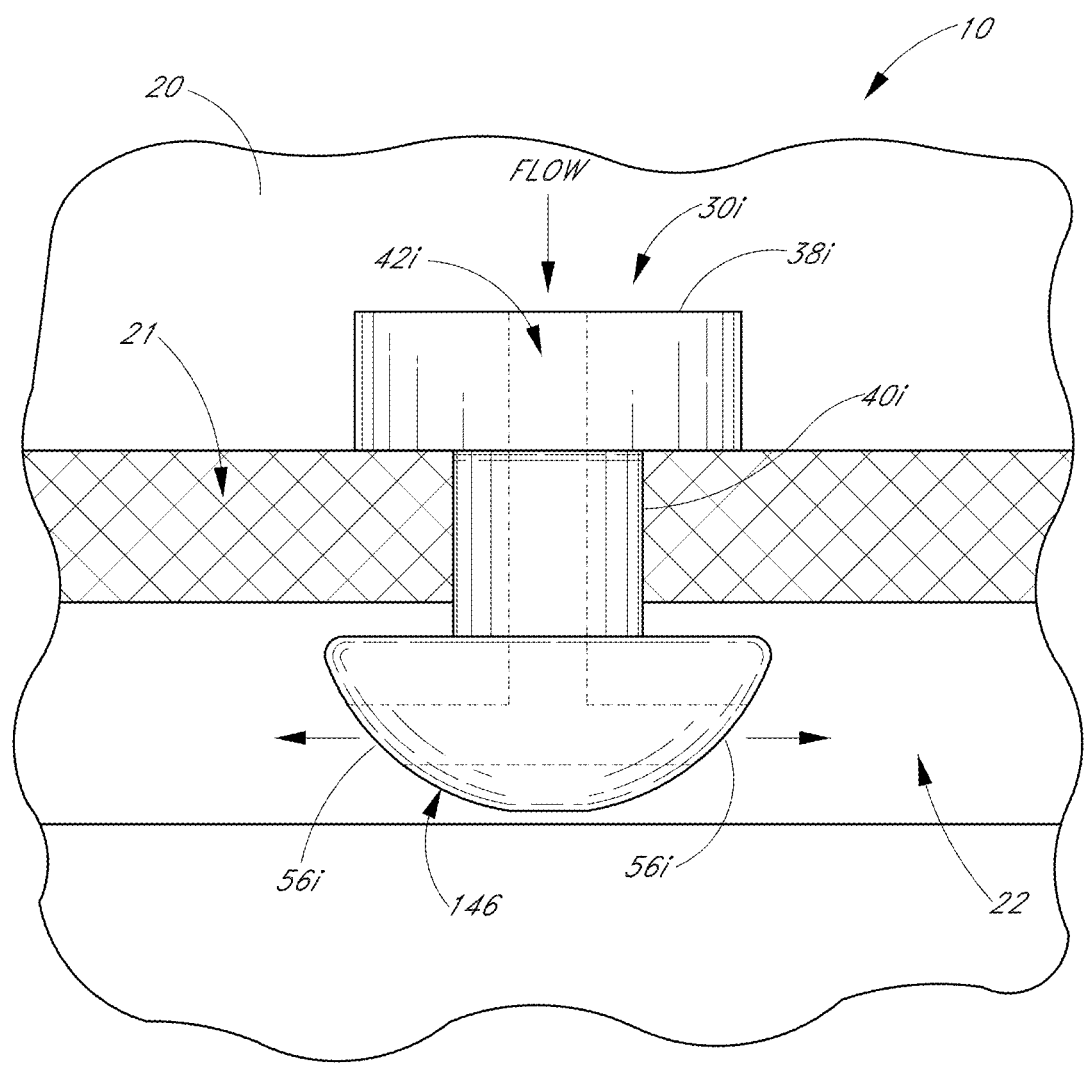
FIG. 36A is a simplified partial view of an eye illustrating the implantation of a glaucoma stent having features and advantages in accordance with one embodiment of the invention.

Grommet Style Stent:

FIG. 36A illustrates a glaucoma stent device 30i having features and advantages in accordance with one embodiment. This embodiment of the trabecular stent 30i includes a head or seat 38i, a tapered base portion 146 and an intermediate narrower waist portion or shank 40i.

In use, the stent 30i (FIG. 36A) is advanced through the trabecular meshwork 21 and the base 146 is pushed into Schlemm's canal 22. The stent 30i is pushed slightly further, if necessary, until the meshwork 21 stretched by the tapered base 146 relaxes back and then contracts to engage the smaller diameter portion waist 40i of the stent 30i. Advantageously, the combination of the larger diameter head or seat 38i and base 146 of the stent 30i constrains undesirable stent movement. As discussed above, correct orientation of the stent 30i is ensured by appropriate fiducial marks, indicia or the like and by positioning of the stent in a preloaded applicator.

Referring to FIG. 36A, the aqueous flows from the anterior chamber 20, through the lumen 42i, then out through two side-ports 56i to be directed in both directions along Schlemm's canal 22. Alternatively, flow could be directed in only one direction through a single side-port 56i. In other embodiments, more than two outlet ports 56i may be efficaciously used, as needed or desired.

Still referring to FIG. 36A, in one embodiment, the stent 30i is inserted through a previously made incision in the trabecular meshwork 21. In other embodiments, the stent 30i may be combined with any of the blade configurations taught or suggested herein to provide self-trephining capability. In these cases, the incision through the trabecular meshwork 21 is made by the self-trephining stent device which has a blade at its base or proximate to the base.

Figure 36B:
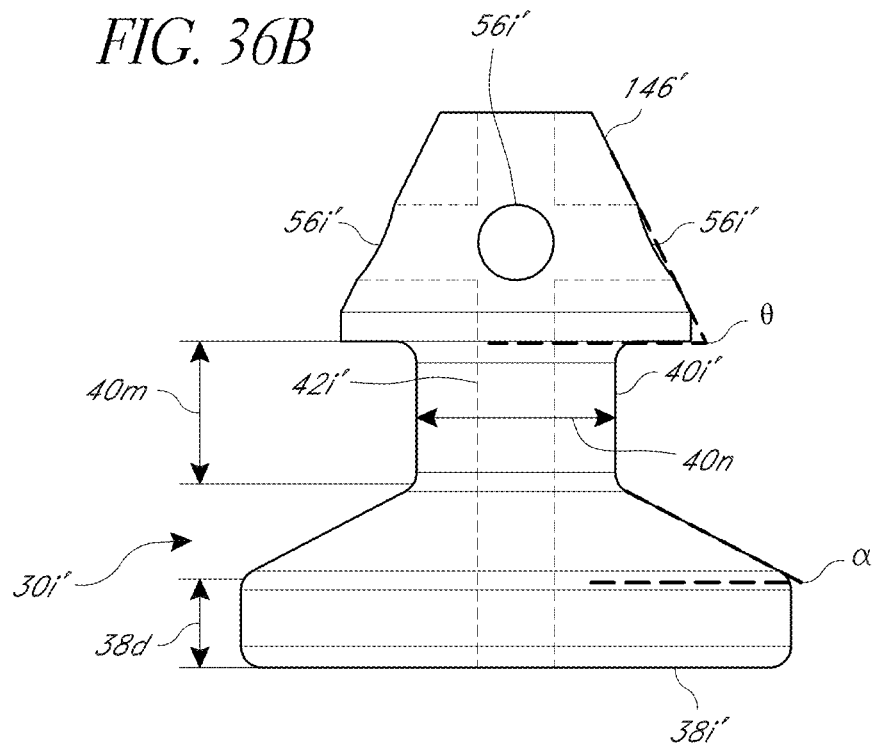
FIG. 36B is a side elevation view of a glaucoma stent having features and advantages in accordance with one embodiment of the invention.
Figure 36C:
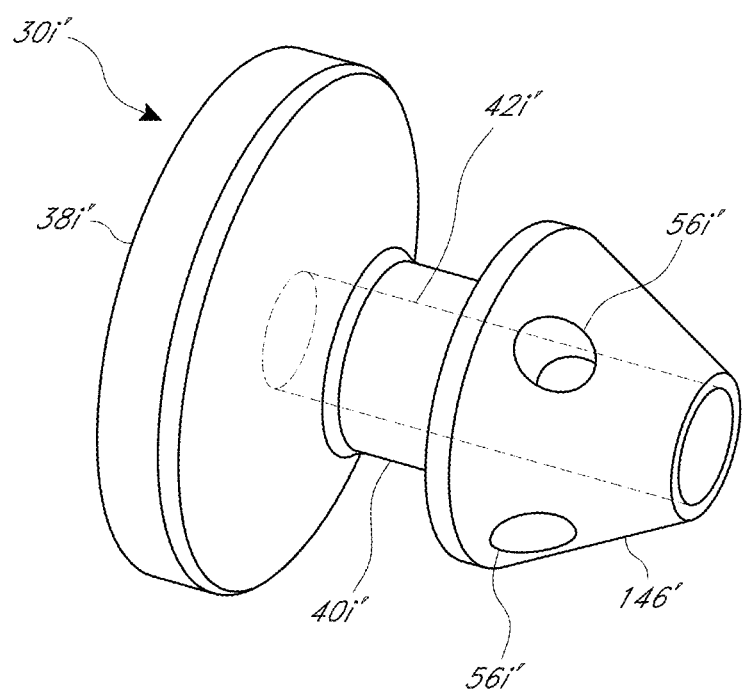
FIG. 36C is a perspective view of the stent of FIG. 36B.

FIG. 36B and FIG. 36C illustrate another embodiment of a trabecular stent 30i'. FIG. 36B shows the glaucoma stent device 30i' from the side while FIG. 36C shows the glaucoma stent device 30i' from a base-biased three-quarters view. The glaucoma stent device 30i' includes a head or seat 38i' with a head or seat depth 38d, a waist portion or shank 40i' with a waist portion or shank external diameter 40n and a waist portion or shank depth 40m, a lumen 42i', a side-port 56i', a tapered base 146', an angle α, and an angle θ.

In operation, the glaucoma stent device 30i' of FIG. 36B and 36C is advanced through the trabecular meshwork 21 of FIG. 2 and the tapered base 146' is pushed into Schlemm's canal 22 of FIG. 2. The glaucoma stent device 30i' is pushed slightly further, if necessary, until the meshwork 21 of FIG. 2 stretched by the tapered base 146' relaxes back and then contracts to engage the smaller diameter portion waist portion or shank 40i' of the glaucoma stent device 30i'. Advantageously, the combination of the larger diameter head or seat 38i' and tapered base 146' of the glaucoma stent device 30i' increases the implantation success and constrains undesirable stent movement. In some embodiments, a hole is made in the trabecular meshwork 21 of FIG. 2 with a device (such as, but not limited to a knife, trephine, punch, drill, scalpel, trocar, or blade) before the glaucoma stent device 30i' is introduced into the anterior chamber of the eye. In other embodiments, a hole is made in the trabecular meshwork 21 of FIG. 2 using the delivery device used to deliver the glaucoma stent device 30i' to the trabecular meshwork 21 of FIG. 21.

Generally, the tapered base 146' is attached to the waist portion or shank 40i' which is attached to the head or seat 38i' to form the glaucoma stent device 30i' illustrated in FIGS. 36B and 36C. A lumen 42i' runs from the top of the head or seat 38i' to the bottom of the tapered base 146' to provide a fluid channel from the anterior chamber to the internal lumen of Schlemm's canal.

In some embodiments, there are four side-ports 56i' intersecting the lumen 42i' in the region of the tapered base 146'. In some embodiments, the at least one side-port 56i' intersects perpendicular to the lumen 42i' (as shown in FIGS. 36B and 36C). In some embodiments, the side-ports 56i' intersect each other in a perpendicular fashion (as shown in FIGS. 36B and 36C). In some embodiments, there is only one side-port 56i'. In some embodiments, there are two side-ports 56i', three side-ports 56i', four side-ports 56i', five side-ports 56i', or six side-ports 56i'. The side-ports 56i' can be generally parallel to the axis of Schlemm's canal or simply positioned to be aligned in or near Schlemm's canal. The side-ports 56i' and provide for additional flow of aqueous from the anterior chamber to the lumen of Schlemm's canal. Side-ports 56i' can be particularly useful if the terminal end of the lumen 42i' residing in Schlemm's canal either becomes plugged or abuts the wall of Schlemm's canal and has concomitantly lower or decreased or even arrested fluid flow.

In some embodiments, the head or seat 38i'of the glaucoma stent device 30i' has a diameter in the range of about 100-3000 µm, about 150-3750 µm, about 200-3500 µm, about 200-3250 µm, about 250-3000 µm, about 300-2750 µm, about 350-2500 µm, about 375-2250 µm, about 400-2000 µm, about 450-1750 µm, about 500-1500 µm, about 550-1250 µm, about 600-1000 µm, and about 650-800 µm or any other diameter which fits within the eye and serves to anchor the glaucoma stent device 30i' appropriately.

In some embodiments, the head or seat depth 38d of the glaucoma stent device 30i' is in the range of about 50-1000 µm, about 60-900 µm, about 70-800 µm, about 80-700 µm, about 90-600 µm, about 100-500 µm, about 110-400 µm, and about 120-300 including about 130-200 µm or any other depth which allows the glaucoma stent device 30i' to seat in the eye and maintain structural integrity and/or alignment of side-ports 56i' to Schlemm's canal.

In some embodiments, the waist portion or shank depth 40m of the glaucoma stent device 30i' is approximately equal to the thickness of the trabecular meshwork 21 of FIG. 2, including the range of about 100-500 µm, about 110-450 µm, about 120-400 µm, about 130-350 µm, about 140-300 µm, about 150-250 µm, and about 160-200 µm.

In some embodiments, the waist portion or shank external diameter 40n of the glaucoma stent device 30i' is in the range of about 100-1500 µm, about 150-1400 µm, about 160-1300 µm, about 170-1200 µm, about 180-1100 µm, about 190-1000 µm, about 200-900 µm, about 210-800 µm, about 220-700 µm, about 230-600 µm, about 240-500 µm, about 250-400, and about 260-300 µm.

In some embodiments, angle α formed by the attachment of the head or seat 38i' to the waist portion or shank 40i' is in the range of about 5-45°, about 7.5-40°, about 10-35°, about 12.5-30°, about 15-25°, and about 17.5-20°. Generally, the lower the angle α, the more of the head or seat 38i'portion of the glaucoma stent device 30i' can be in contact with the trabecular meshwork 21 of FIG. 2.

In some embodiments, the angle θ of the tapered base 146' is in the range of about 45-80°, about 47.5-77.5°, about 50-75°, about 52.5-72.5°, about 55-70°, about 57.5-67.5°, and about 60-65° or any other angle appropriate for fitting inside Schlemm's canal and helping in anchoring the glaucoma stent device 30i' in the eye.

In some embodiments, the tapered base 146' is approximately as deep as is Schlemm's canal. In some embodiments, the periphery of the tapered base 146' is approximately equal to the periphery of the cross section of Schlemm's canal. In some embodiments, the tapered base 146' is flattened (as shown in FIG. 36B. In some embodiments, the tapered base 146' is not flattened and can extend into the tissue of the wall of Schlemm's canal to anchor the glaucoma stent device 30i'.

FIGS. 36D, 36E, and 36F illustrate another embodiment of a glaucoma stent device 30i'. The glaucoma stent device 30i' illustrated in FIGS. 36D-36F can have approximately the same structures as the glaucoma stent device 30i' illustrated in FIG. 36B and 36C described immediately above, including but not limited to a tapered base 146', a waist portion or shank 40i', a head or seat 38i', a lumen 42i', and at least one side-port 56i'. In addition to the aforementioned features, in some embodiments, the glaucoma stent device 30i' of FIGS. 36D-36F can include at least one head or seat side-port 57i'.

In some embodiments, the head or seat side-port 57i' can extend through the head or seat 38i' (e.g., parallel to the planar surface of the head or seat 38i'). In some embodiments, the head or seat side-port 57i' can be disposed parallel to the at least one side-port 56i' in the tapered base 146'.

In some embodiments, there are four head or seat side-ports 57i' intersecting the lumen 42i' in the region of the head or seat 38i'. In some embodiments, the at least one head or seat side-port 57i' intersects perpendicular to the lumen 42i' (as shown in FIG. 36D). In some embodiments, the head or seat side-ports 57i' intersect each other in a perpendicular fashion (as shown in FIG. 36E). In some embodiments, there is only one head or seat side-port 57i'. In some embodiments, there are two head or seat side-ports 57i', three head or seat side-ports 57i', four head or seat side-ports 57i', five head or seat side-ports 57i', or six head or seat side-ports 57i'. The head or seat side-ports 57i' can be generally parallel to the axis of Schlemm's canal. In some embodiments, when in an implanted location, the head or seat side-ports 57i' can be located in the anterior chamber of the eye. The head or seat side-ports 57i' can provide for additional flow of aqueous from the anterior chamber to the lumen of Schlemm's canal.

The glaucoma stent device 30i' illustrated in FIGS. 36D, 36E, and 36F can be particularly useful in closed angle patients. Additionally, this glaucoma stent device 30i' can be inserted into the eye in combination with an iridotomy to create an improved outflow pathway in the aforementioned closed angle cases.

FIGS. 36G, 36H, and 36I illustrate another embodiment of a glaucoma stent device 30$i'$. The glaucoma stent device 30$i'$ illustrated in FIGS. 36G-36I can have approximately the same structures as the glaucoma stent device 30$i'$ illustrated in FIGS. 36D, 36E, and 36F described immediately above, including but not limited to a tapered base 146', a waist portion or shank 40$i'$, a head or seat 38$i'$, a lumen 42$i'$, and at least one side-port 56$i'$. In addition to the aforementioned features, in some embodiments, the glaucoma stent device 30$i'$ of FIGS. 36G-36I can includes at least one head or seat half-cylinder side-port 57$j'$.

In some embodiments, the head or seat half-cylinder side-port 57$j'$ can extend through the head or seat 38$i'$ (e.g., parallel to the planar surface of the head or seat 38$i'$). In some embodiments, the head or seat half-cylinder side-port 57$j'$ can be disposed parallel to the at least one side-port 56$i'$ in the tapered base 146'.

In some embodiments, there are four head or seat half-cylinder side-ports 57$j'$ intersecting the lumen 42$i'$ in the region of the head or seat 38$i'$. In some embodiments, the at least one head or seat half-cylinder side-port 57$j'$ intersects perpendicular to the lumen 42$i'$ (as shown in FIG. 36G). In some embodiments, the head or seat half-cylinder side-ports 57$j'$ intersect each other in a perpendicular fashion (as shown in FIG. 36H). In some embodiments, there is only one head or seat half-cylinder side-port 57$j'$. In some embodiments, there are two head or seat half-cylinder side-ports 57$j'$, three head or seat half-cylinder side-ports 57$j'$, four head or seat half-cylinder side-ports 57$j'$, five head or seat half-cylinder side-ports 57$j'$, or six head or seat half-cylinder side-ports 57$j'$. The head or seat half-cylinder side-ports 57$j'$ can be generally parallel to the axis of Schlemm's canal. In some embodiments, when in an implanted location, the head or seat half-cylinder side-ports 57$j'$ can be located in the anterior chamber of the eye. The head or seat half-cylinder side-ports 57$j'$ can provide for additional flow of aqueous from the anterior chamber to the lumen of Schlemm's canal. The glaucoma stent device 30$i'$ illustrated in FIGS. 36G, 36H, and 36I can be particularly useful in closed angle patients. Additionally, this glaucoma stent device 30$i'$ can be inserted into the eye in combination with an iridotomy to create an improved outflow pathway in the aforementioned closed angle cases.

FIGS. 36J and 36K illustrate another embodiment of a glaucoma stent device 30$i'$. The glaucoma stent device 30$i'$ illustrated in FIGS. 36J and 36K can have approximately the same structures as the glaucoma stent device 30$i'$ illustrated in FIGS. 36D, 36E, and 36F described above, including but not limited to a tapered base 146', a waist portion or shank 40$i'$, a head or seat 38$i'$, a lumen 42$i'$, and at least one side-port 56$i'$. In addition to the aforementioned features, in some embodiments, the glaucoma stent device 30$i'$ of FIGS. 36J and 36K can include a head or seat shank 40$k'$, a head or seat button 38$k'$, a head or seat button dome 38$n$, and at least one head or seat shank side-port 57$k'$.

In some embodiments, the head or seat shank 40$k'$ can extend from the back of the head or seat 38$i'$. In some embodiments, the head or seat shank 40$k'$ can have a diameter less than the diameter of the head or seat 38$i'$. In some embodiments, the diameter of the head or seat shank 40$k'$ can be in the range of about 20-100% of the diameter of the head or seat 38$i'$, about 30-90% of the diameter of the head or seat 38$i'$, about 40-80% of the diameter of the head or seat 38$i'$ about 50-70% of the diameter of the head or seat 38$i'$, and about 60% of the diameter of the head or seat 38$i'$.

In some embodiments, the head or seat shank 40$k'$ has a thickness in the range of about 100-500 µm, about 110-450 µm, about 120-400 µm, about 130-350 µm, about 140-300 µm, about 150-250 µm, and about 160-200 µm.

In some embodiments, the head or seat button 38$k'$ can extend from the back of the head or seat shank 40$k'$. In some embodiments, the head or seat button 38$k'$ can have a head or seat button dome 38$n$. In other embodiments, the head or seat button 38$k'$ is flat. In some embodiments, the head or seat button 38$k'$ can have a diameter the same as the diameter of the head or seat 38$i'$. In some embodiments, the head or seat button 38$k'$ can have a diameter that is greater than the diameter of the head or seat 38$i'$. In some embodiments, the head or seat button 38$k'$ can have a diameter that is less than the diameter of the head or seat 38$i'$. In some embodiments, the diameter of the head or seat button 38$k'$ can be in the range of about 50-150% of the diameter of the head or seat 38$i'$, about 60-140% of the diameter of the head or seat 38$i'$, about 70-130% of the diameter of the head or seat 38$i'$, about 80-120% of the diameter of the head or seat 38$i'$, about 90-110% of the diameter of the head or seat 38$i'$, and about 100% of the diameter of the head or seat 38$i'$.

In some embodiments, the head or seat button 38$k'$ *has a thickness in the range of about* 100-500 µm, about 110-450 µm, about 120-400 µm, about 130-350 µm, about 140-300 µm, about 150-250 µm, and about 160-200 µm.

In some embodiments, the head or seat shank side-port 57$k'$ can extend through the head or seat shank 40$k'$ (e.g., parallel to the planar surface of the head or seat 38$i'$). In some embodiments, the head or seat shank side-port 57$k'$ can be disposed parallel to the at least one side-port 56$i'$ in the tapered base 146'.

In some embodiments, there are four head or seat shank side-ports 57$k'$ intersecting the lumen 42$i'$ in the region of the head or seat shank 40$k'$. In some embodiments, the at least one head or seat shank side-port 57$k'$ intersects perpendicular to the lumen 42$i'$ (as shown in FIG. 36J). In some embodiments, the head or seat shank side-ports 57$k'$ intersect each other in a perpendicular fashion (as shown in FIGS. 36J and 36K). In some embodiments, there is only one head or seat shank side-port 57$k'$. In some embodiments, there are two head or seat shank side-ports 57$k'$, three head or seat shank side-ports 57$k'$, four head or seat shank side-ports 57$k'$, five head or seat shank side-ports 57$k'$, or six head or seat shank side-ports 57$k'$. The head or seat shank side-ports 57$k'$ can be generally parallel to the axis of Schlemm's canal. In some embodiments, when in an implanted location, the head or seat shank side-port 57$k'$ can be located in the anterior chamber of the eye. The head or seat shank side-ports 57$k'$ can provide for additional flow of aqueous from the anterior chamber to the lumen of Schlemm's canal. The glaucoma stent device 30$i'$ illustrated in FIGS. 36J and 36K can be particularly useful in closed angle patients. Additionally, this glaucoma stent device 30$i'$ can be inserted into the eye in combination with an iridotomy to create an improved outflow pathway in the aforementioned closed angle cases.

In some embodiments, one or more of the glaucoma stent devices discussed above may be delivered into the eye with a delivery device such as disclosed in the attached Appendix A which is a part of the present specification. One or more glaucoma stents may be preloaded onto the delivery device to form a glaucoma stent/delivery device system.

Figure 37:
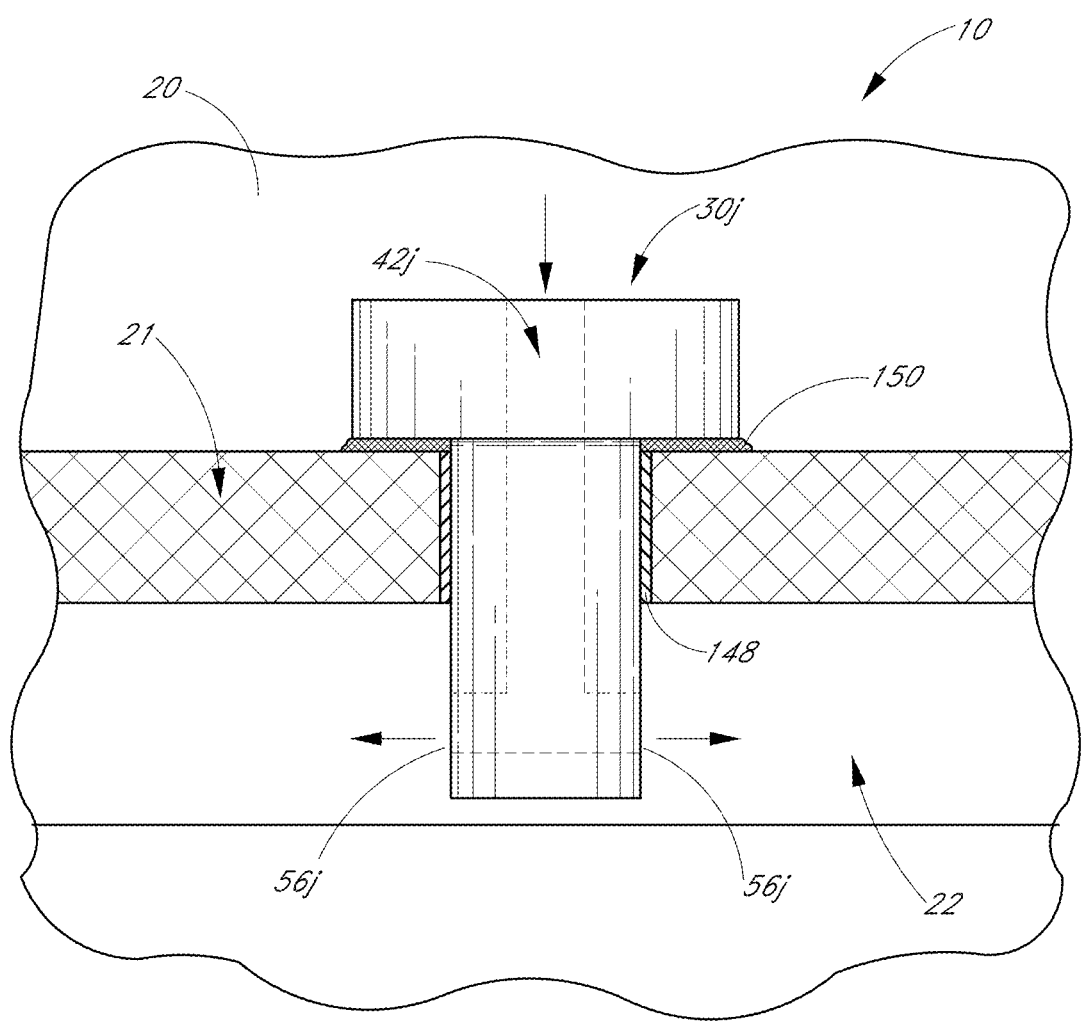
FIG. 37 is a simplified partial view of an eye illustrating the implantation of a glaucoma stent having features and advantages in accordance with one embodiment of the invention.

Biointeractive Stent:

FIG. 37 illustrates a glaucoma stent device 30j having features and advantages in accordance with one embodiment. This embodiment of the trabecular stent 30j utilizes a region of biointeractive material 148 that provides a site for the trabecular meshwork 21 to firmly grip the stent 30j by ingrowth of the tissue into the biointeractive material 148. As shown in FIG. 37, preferably the biointeractive layer 148 is applied to those surfaces of the stent 30j which would abut against or come in contact with the trabecular meshwork 21.

In one embodiment, the biointeractive layer 148 (FIG. 37) may be a region of enhanced porosity with a growth promoting chemical. In one embodiment, a type of bio-glue 150 that dissolves over time is used to hold the stent secure during the time between insertion and sufficient ingrowth for stabilization. As discussed above, correct orientation of the stent 30j is ensured by appropriate fiducial marks, indicia or the like and by positioning of the stent in a preloaded applicator.

Referring to FIG. 37, the aqueous flows from the anterior chamber 20, through the lumen 42j, then out through two side-ports 56j to be directed in both directions along Schlemm's canal 22. Alternatively, flow could be directed in only one direction through a single side-port 56j. In other embodiments, more than two outlet ports 56j may be efficaciously used, as needed or desired.

Still referring to FIG. 37, in one embodiment, the stent 30j is inserted through a previously made incision in the trabecular meshwork 21. In other embodiments, the stent 30j may be combined with any of the blade configurations taught or suggested herein to provide self-trephining capability. In these cases, the incision through the trabecular meshwork 21 is made by the self-trephining stent device which has a blade at its base or proximate to the base.

Figure 38:
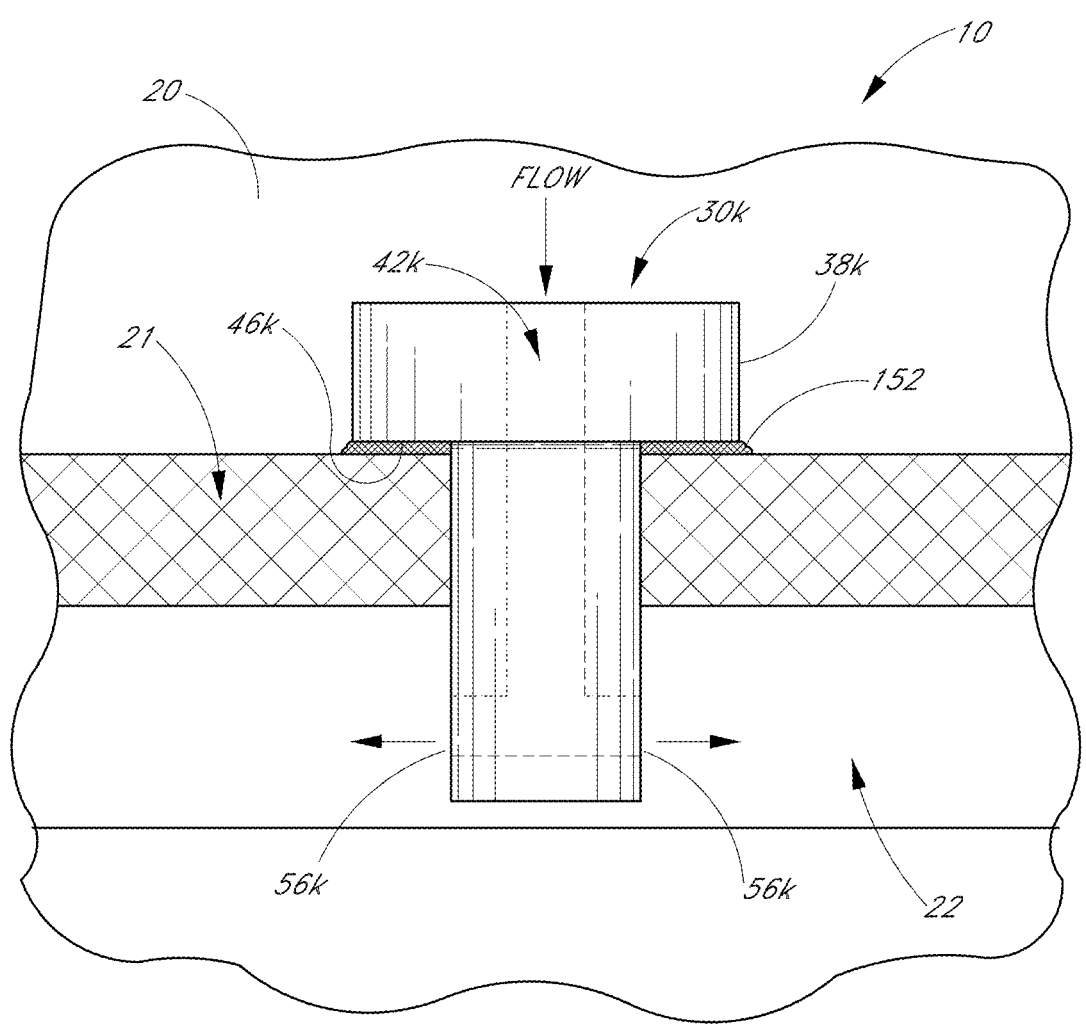
FIG. 38 is a simplified partial view of an eye illustrating the implantation of a glaucoma stent having features and advantages in accordance with one embodiment of the invention.

Glued or Welded Stent:

FIG. 38 illustrates a glaucoma stent device 30k having features and advantages in accordance with one embodiment. This embodiment of the trabecular stent 30k is secured in place by using a permanent (non-dissolving) bio-glue 152 or a "welding" process (e.g. heat) to form a weld 152. The stent 30k has a head or seat 38k and a lower surface 46k.

The stent 30k is advanced through the trabecular meshwork 21 until the head or seat 38k comes to rest on the trabecular meshwork 21, that is, the head lower surface 46k abuts against the trabecular meshwork 21, and the glue or weld 152 is applied or formed therebetween, as shown in FIG. 38. As discussed above, correct orientation of the stent 30k is ensured by appropriate fiducial marks, indicia or the like and by positioning of the stent in a preloaded applicator.

Referring to FIG. 38, the aqueous flows from the anterior chamber 20, through the lumen 42k, then out through two side-ports 56k to be directed in both directions along Schlemm's canal 22. Alternatively, flow could be directed in only one direction through a single side-port 56k. In other embodiments, more than two outlet ports 56k may be efficaciously used, as needed or desired.

Still referring to FIG. 38, in one embodiment, the stent 30k is inserted through a previously made incision in the trabecular meshwork 21. In other embodiments, the stent 30k may be combined with any of the blade configurations taught or suggested herein to provide self-trephining capability. In these cases, the incision through the trabecular meshwork 21 is made by the self-trephining stent device which has a blade at its base or proximate to the base.

Figure 39:
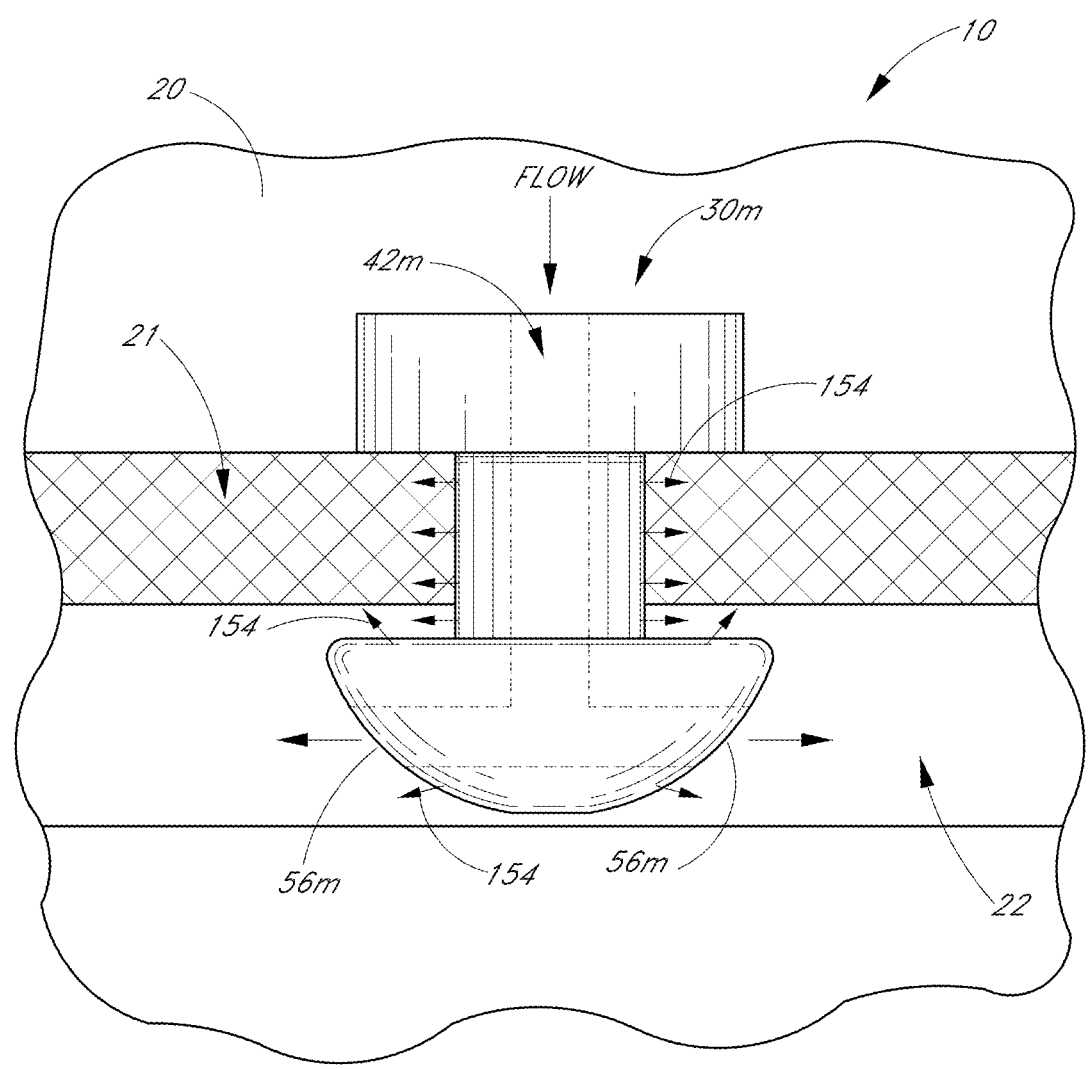
FIG. 39 is a simplified partial view of an eye illustrating the implantation of a glaucoma stent having features and advantages in accordance with one embodiment of the invention.

Hydrophilic Latching Stent:

FIG. 39 illustrates a glaucoma stent device 30m having features and advantages in accordance with one embodiment. This embodiment of the trabecular stent 30m is fabricated from a hydrophilic material that expands with absorption of water. Desirably, this would enable the device 30m to be inserted through a smaller incision in the trabecular meshwork 21. The subsequent expansion (illustrated by the smaller arrows 154) of the stent 30m would advantageously enable it to latch in place in the trabecular meshwork 21. As discussed above, correct orientation of the stent 30m is ensured by appropriate fiducial marks, indicia or the like and by positioning of the stent in a preloaded applicator.

Referring to FIG. 39, the aqueous flows from the anterior chamber 20, through the lumen 42m, then out through two side-ports 56m to be directed in both directions along Schlemm's canal 22. Alternatively, flow could be directed in only one direction through a single side-port 56m. In other embodiments, more than two outlet ports 56m may be efficaciously used, as needed or desired.

Still referring to FIG. 39, in one embodiment, the stent 30m is inserted through a previously made incision in the trabecular meshwork 21. In other embodiments, the stent 30m may be combined with any of the blade configurations taught or suggested herein to provide self-trephining capability. In these cases, the incision through the trabecular meshwork 21 is made by the self-trephining stent device which has a blade at its base or proximate to the base.

Figure 40:
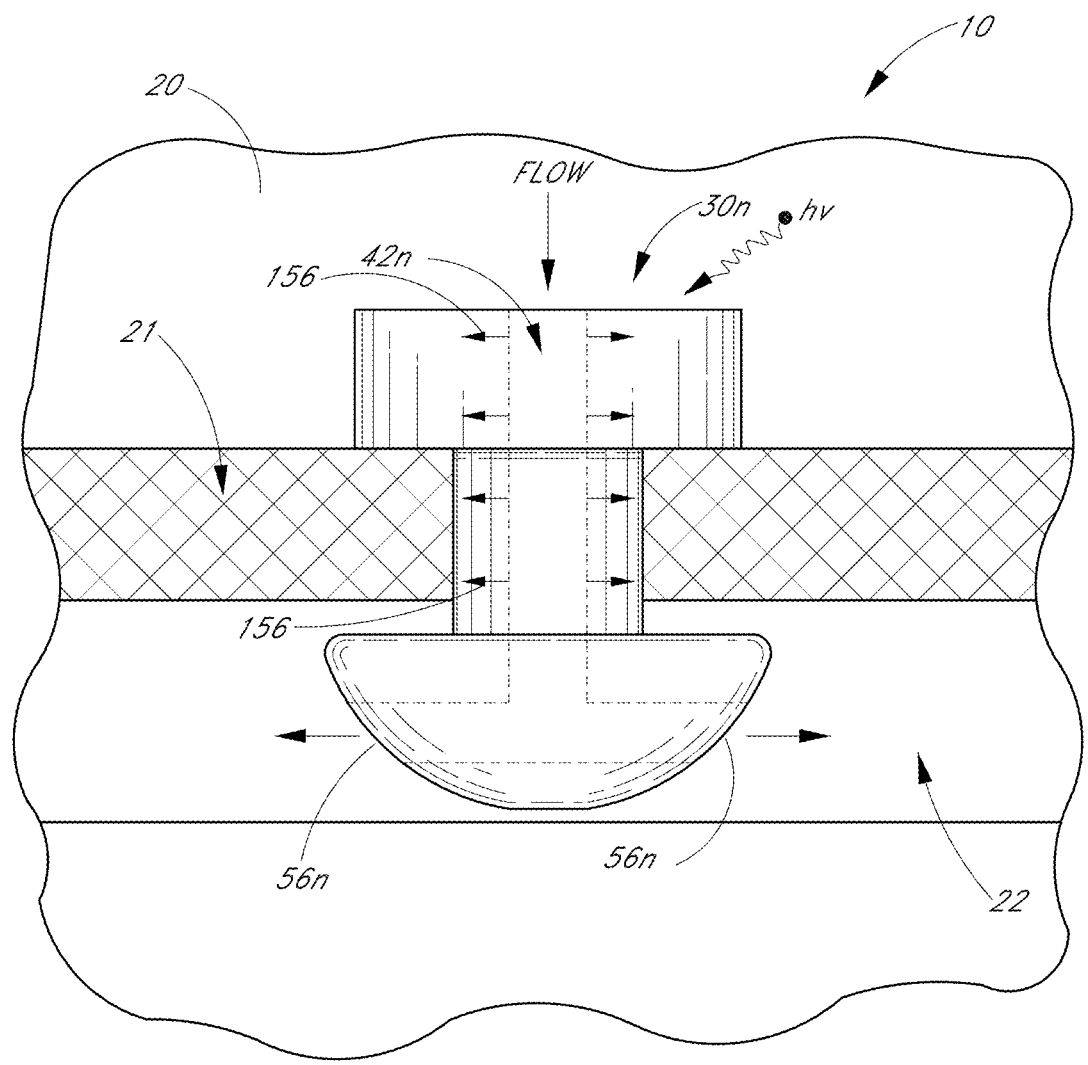
FIG. 40 is a simplified partial view of an eye illustrating the implantation of a glaucoma stent having features and advantages in accordance with one embodiment of the invention.

Photodynamic Stent:

FIG. 40 illustrates a glaucoma stent device 30n having features and advantages in accordance with one embodiment. This embodiment of the trabecular stent 30n is fabricated from a photodynamic material that expands on exposure to light.

It is commonly known that there is a diurnal variation in the aqueous humor production by the eye—it is higher during the day than it is at night. The lumen 42n of the stent 30n responds to light entering the cornea during the day by expanding and allowing higher flow of aqueous through the lumen 42n and into Schlemm's canal 22. This expansion is generally indicated by the smaller arrows 156 (FIG. 40) which show the lumen 42n (and ports) expanding or opening in response to light stimulus. (The light or radiation energy E is generally given by E=hv, where h is Planck's constant and v is the frequency.) At night, in darkness, the lumen diameter decreases and reduces the flow allowed through the lumen 42n. In one embodiment, an excitation wavelength that is different from that commonly encountered is provided on an as-needed basis to provide higher flow of aqueous to Schlemm's canal 22.

This photodynamic implementation is shown in FIG. 40 for the self-latching style of stent 30n, but can be efficaciously used with any of the other stent embodiments, as needed or desired. As discussed above, correct orientation of the stent 30n is ensured by appropriate fiducial marks, indicia or the like and by positioning of the stent in a preloaded applicator.

Referring to FIG. 40, the aqueous flows from the anterior chamber 20, through the lumen 42n, then out through two side-ports 56n to be directed in both directions along Schlemm's canal 22. Alternatively, flow could be directed in only one direction through a single side-port 56n. In other embodiments, more than two outlet ports 56n may be efficaciously used, as needed or desired.

Still referring to FIG. 40, in one embodiment, the stent 30n is inserted through a previously made incision in the trabecular meshwork 21. In other embodiments, the stent 30n may be combined with any of the blade configurations taught or suggested herein to provide self-trephining capability. In these cases, the incision through the trabecular meshwork 21 is made by the self-trephining stent device which has a blade at its base or proximate to the base.

Figure 41:
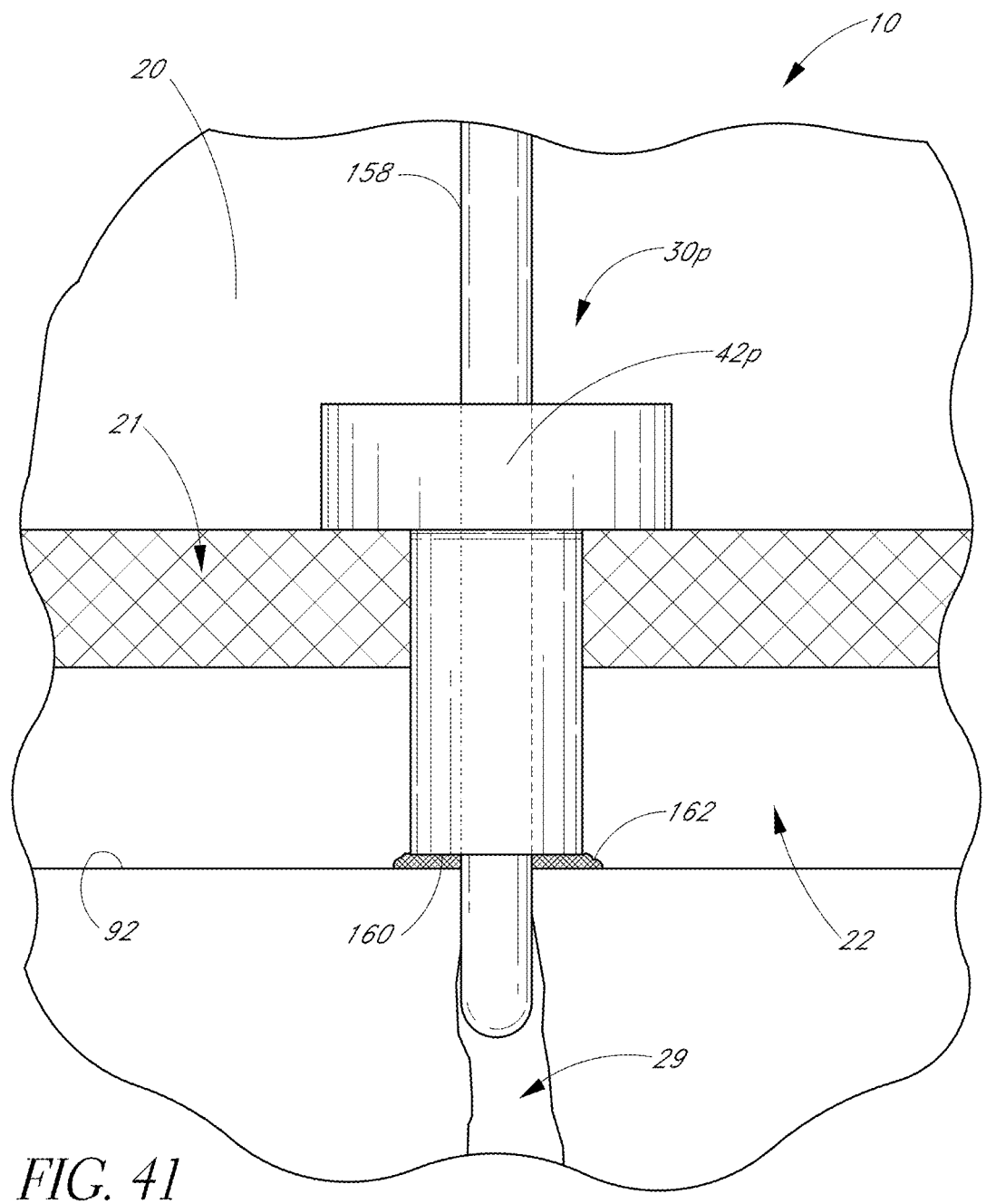
FIG. 41 is a simplified partial view of an eye illustrating the implantation of a glaucoma stent having features and advantages in accordance with one embodiment of the invention.

Collector Channel Alignment Stent:

FIG. 41 illustrates a glaucoma stent device 30p having features and advantages in accordance with one embodiment. This figure depicts an embodiment of a stent 30p that directs aqueous from the anterior chamber 20 directly into a collector channel 29 which empties into aqueous veins. The stent 30p has a base or distal end 160.

In the illustrated embodiment of FIG. 41, a removable alignment pin 158 is utilized to align the stent lumen 42p with the collector channel 29. In use, the pin 158 extends through the stent lumen 42p and protrudes through the base 160 and extends into the collector channel 29 to center and/or align the stent 30p over the collector channel 29. The stent 30p is then pressed firmly against the back wall 92 of Schlemm's canal 22. A permanent bio-glue 162 is used between the stent base and the back wall 92 of Schlemm's canal 22 to seat and securely hold the stent 30p in place. Once positioned, the pin 158 is withdrawn from the lumen 42p to allow the aqueous to flow directly from the anterior chamber 20 into the collector duct 29. The collector ducts are nominally 20 to 100 micrometers (μm) in diameter and are visualized with a suitable microscopy method (such as ultrasound biomicroscopy (UBM)) or laser imaging to provide guidance for placement of the stent 30p.

Referring to FIG. 41, in one embodiment, the stent 30p is inserted through a previously made incision in the trabecular meshwork 21. In other embodiments, the stent 30p may be combined with any of the blade configurations taught or suggested herein to provide self-trephining capability. In these cases, the incision through the trabecular meshwork 21 is made by the self-trephining stent device which has a blade at its base or proximate to the base.

Figure 42:
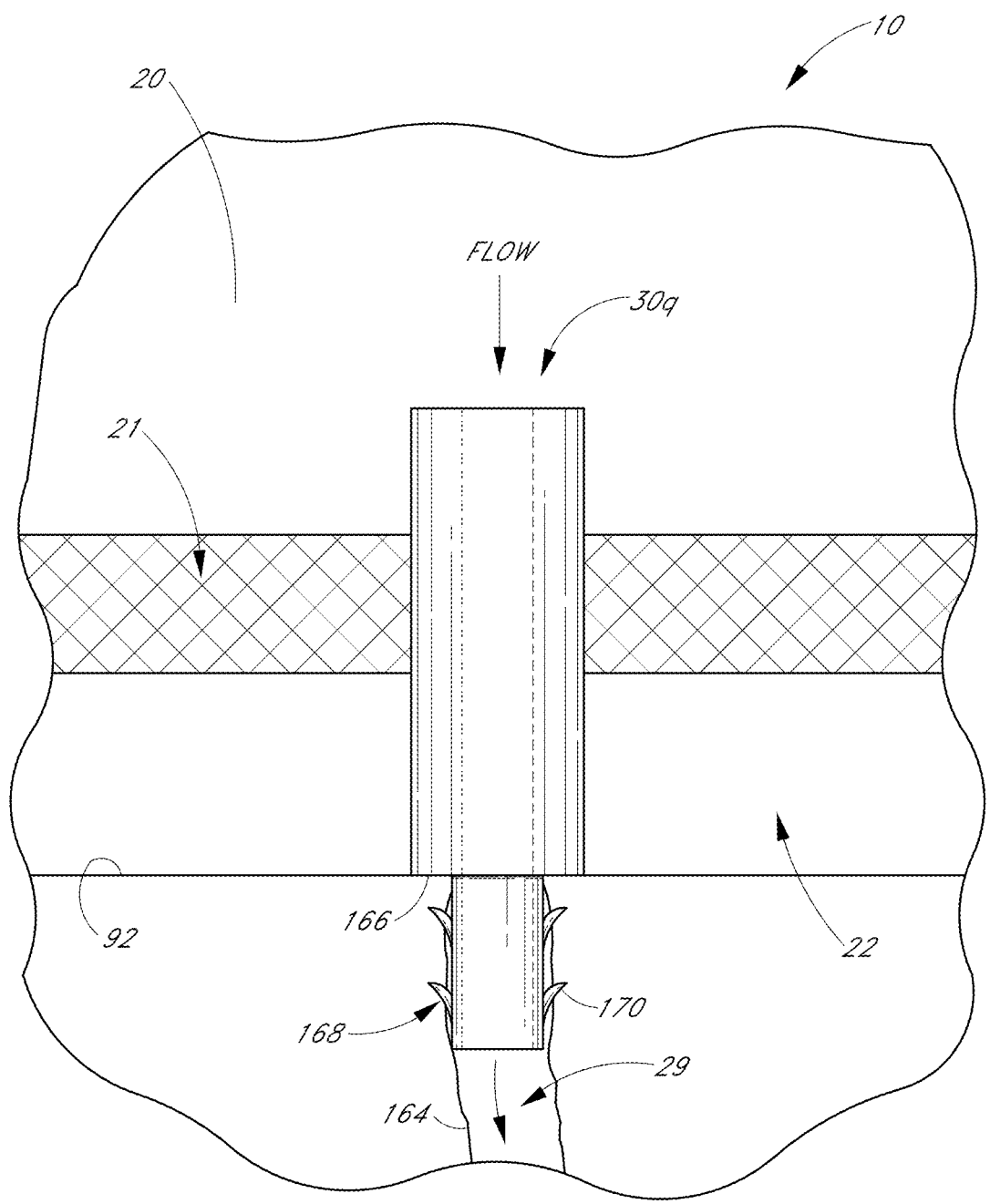
FIG. 42 is a simplified partial view of an eye illustrating the implantation of a glaucoma stent having features and advantages in accordance with one embodiment of the invention.

Barbed Stent (Anterior Chamber to Collector Channel):

FIG. 42 illustrates a glaucoma stent device 30q having features and advantages in accordance with one embodiment. This figure depicts an embodiment of a stent 30q that directs aqueous from the anterior chamber 20 directly into a collector channel 29 which empties into aqueous veins. The stent 30q has a base or distal end 166 and the channel 29 has wall(s) 164.

In the illustrated embodiment of FIG. 42, a barbed, small-diameter extension or pin 168 on the stent base 166 is guided into the collector channel 29 and anchors on the wall(s) 164 of the channel 29. The pin 168 has barbs 170 which advantageously provide anchoring of the stent 30q. The collector ducts 29 are nominally 20 to 100 micrometers (μm) in diameter and are visualized with a suitable microscopy method (such as ultrasound biomicroscopy (UBM)) or laser imaging to provide guidance for placement of the stent.

Referring to FIG. 42, in one embodiment, the stent 30q is inserted through a previously made incision in the trabecular meshwork 21. In other embodiments, the stent 30q may be combined with any of the blade configurations taught or suggested herein to provide self-trephining capability. In these cases, the incision through the trabecular meshwork 21 is made by the self-trephining stent device which has a blade at its base or proximate to the base.

Figure 43:
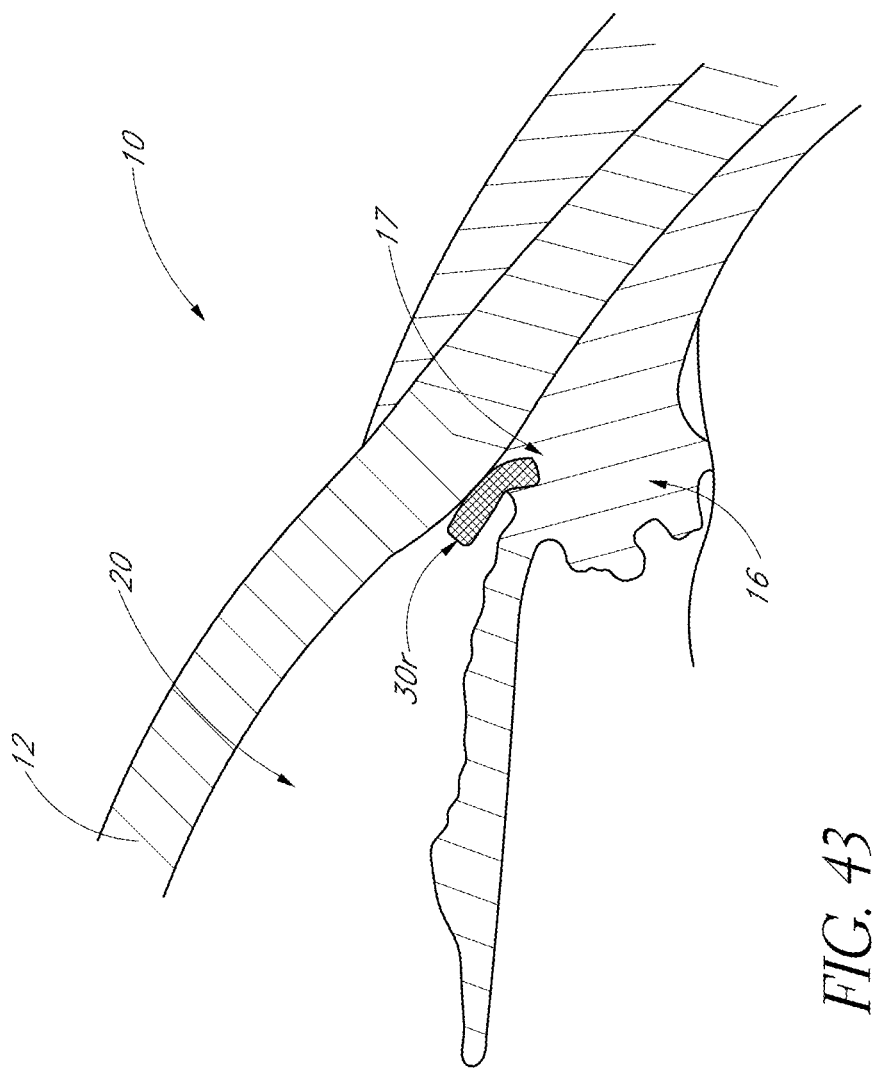
FIG. 43 is a simplified partial view of an eye illustrating the implantation of a valved tube stent device having features and advantages in accordance with one embodiment of the invention.

Valved Tube Stent (Anterior Chamber to Choroid):

FIG. 43 illustrates a valved tube stent device 30r having features and advantages in accordance with one embodiment. This is an embodiment of a stent 30r that provides a channel for flow between the anterior chamber 20 and the highly vascular choroid 17. Clinically, the choroid 17 can be at pressures lower than those desired for the eye 10. Therefore, this stent 30r includes a valve with an opening pressure equal to the desired pressure difference between the choroid 17 and the anterior chamber 10 or a constriction that provide the desired pressure drop.

Figure 44:
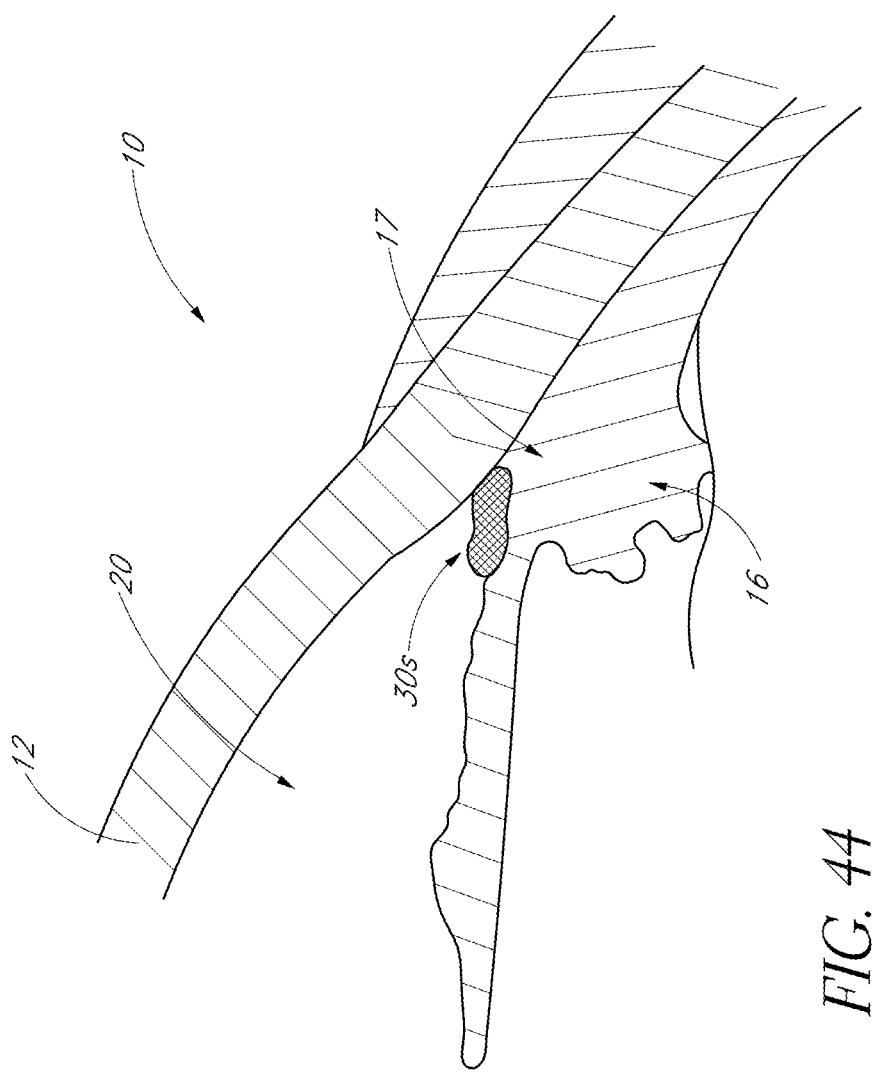
FIG. 44 is a simplified partial view of an eye illustrating the implantation of an osmotic membrane device having features and advantages in accordance with one embodiment of the invention.

Osmotic Membrane (Anterior Chamber to Choroid):

FIG. 44 illustrates an osmotic membrane device 30s having features and advantages in accordance with one embodiment. This embodiment provides a channel for flow between the anterior chamber 20 and the highly vascular choroid 17. The osmotic membrane 30s is used to replace a portion of the endothelial layer of the choroid 17. Since the choroid 17 is highly vascular with blood vessels, the concentration of water on the choroid side is lower than in the anterior chamber 20 of the eye 10. Therefore, the osmotic gradient drives water from the anterior chamber 20 into the choroid 17.

Clinically, the choroid 17 (FIG. 44) can be at pressures lower than those desired for the eye 10. Therefore, desirably, both osmotic pressure and the physical pressure gradient are in favor of flow into the choroid 17. Flow control is provided by proper sizing of the area of the membrane,—the larger the membrane area is the larger the flow rate will be. This advantageously enables tailoring to tune the flow to the desired physiological rates.

Figure 45:
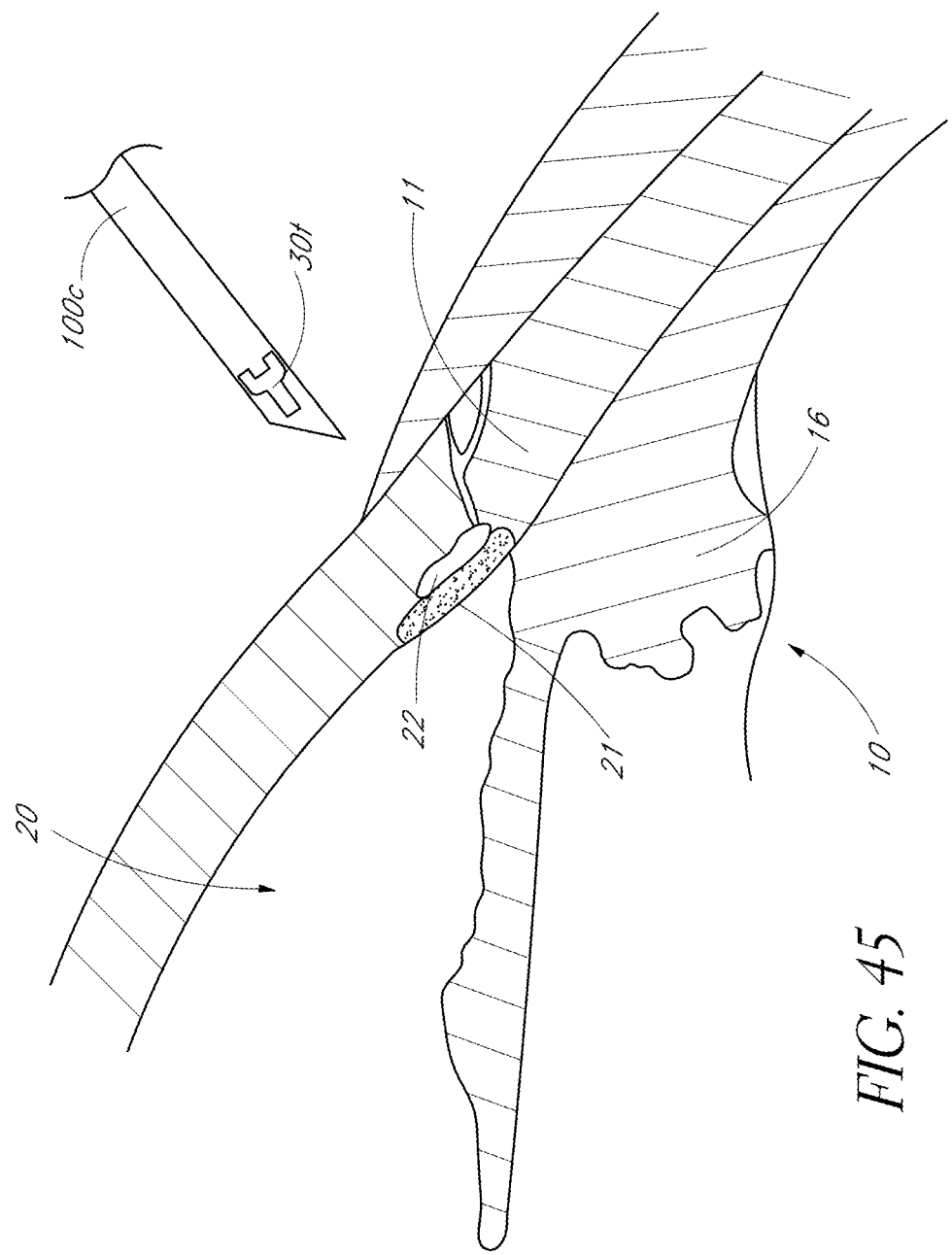
FIG. 45 is a simplified partial view of an eye illustrating the implantation of a glaucoma stent using ab externo procedure having features and advantages in accordance with one embodiment of the invention.

Ab Externo Insertion of Stent via Small Puncture:

FIG. 45 illustrates the implantation of a stent 30t using an ab externo procedure having features and advantages in accordance with one embodiment. In the ab externo procedure of FIG. 45, the stent 30t is inserted into Schlemm's canal 21 with the aid of an applicator or delivery apparatus 100c that creates a small puncture into the eye 10 from outside.

Referring to FIG. 45, the stent 30t is housed in the applicator 100c, and pushed out of the applicator 100c once the applicator tip is in position within the trabecular meshwork 21. Since the tissue surrounding the trabecular meshwork 21 is optically opaque, an imaging technique, such as ultrasound biomicroscopy (UBM) or a laser imaging technique, is utilized. The imaging provides guidance for the insertion of the applicator tip and the deployment of the stent 30t. This technique can be used with a large variety of stent embodiments with slight modifications since the trabecular meshwork 21 is punctured from the scleral side rather than the anterior chamber side in the ab externo insertion.

Figure 46:
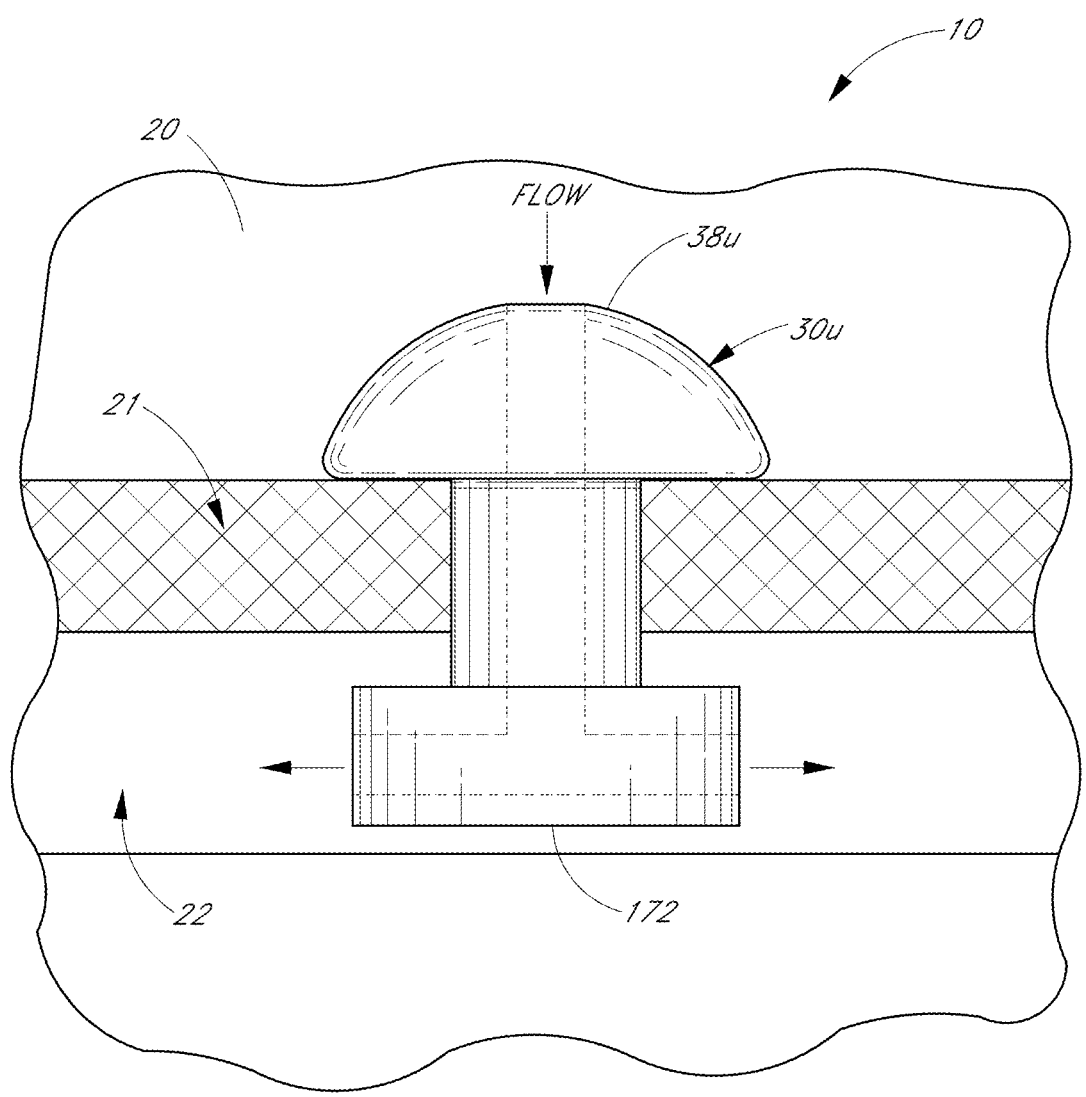
FIG. 46 is a simplified partial view of an eye illustrating the implantation of a glaucoma stent having features and advantages in accordance with a modified embodiment of the invention.

FIG. 46 a glaucoma stent device 30u having features and advantages in accordance with a modified embodiment. This grommet-style stent 30u for ab externo insertion is a modification of the embodiment of FIG. 36A. In the embodiment of FIG. 46, the upper part or head 38u is tapered while the lower part or base 172 is flat, as opposed to the embodiment of FIG. 36A. The stent 30u is inserted from the outside of the eye 10 through a puncture in the sclera. Many of the other embodiments of stents taught or suggested herein can be modified for similar implantation.

This ultra-microscopic device 30u (FIG. 46) can be used with (1) a targeting Lasik-type laser, or with (2) contact on eyes or with (3) combined ultrasound microscope or (4) other device insertor handpiece.

Figure 47:
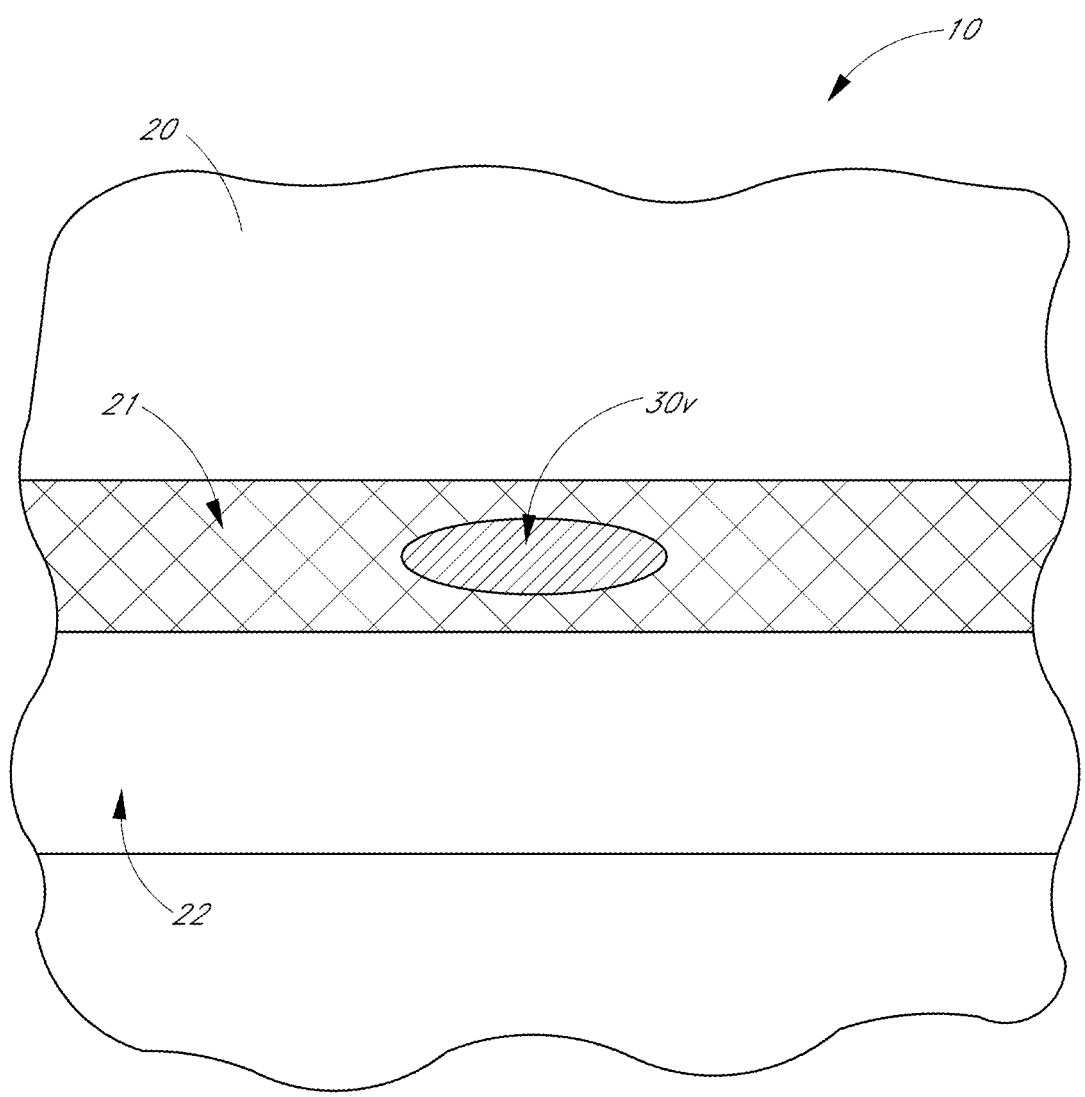
FIG. 47 is a simplified partial view of an eye illustrating the implantation of a drug release implant having features and advantages in accordance with one embodiment of the invention.
Figure 48:
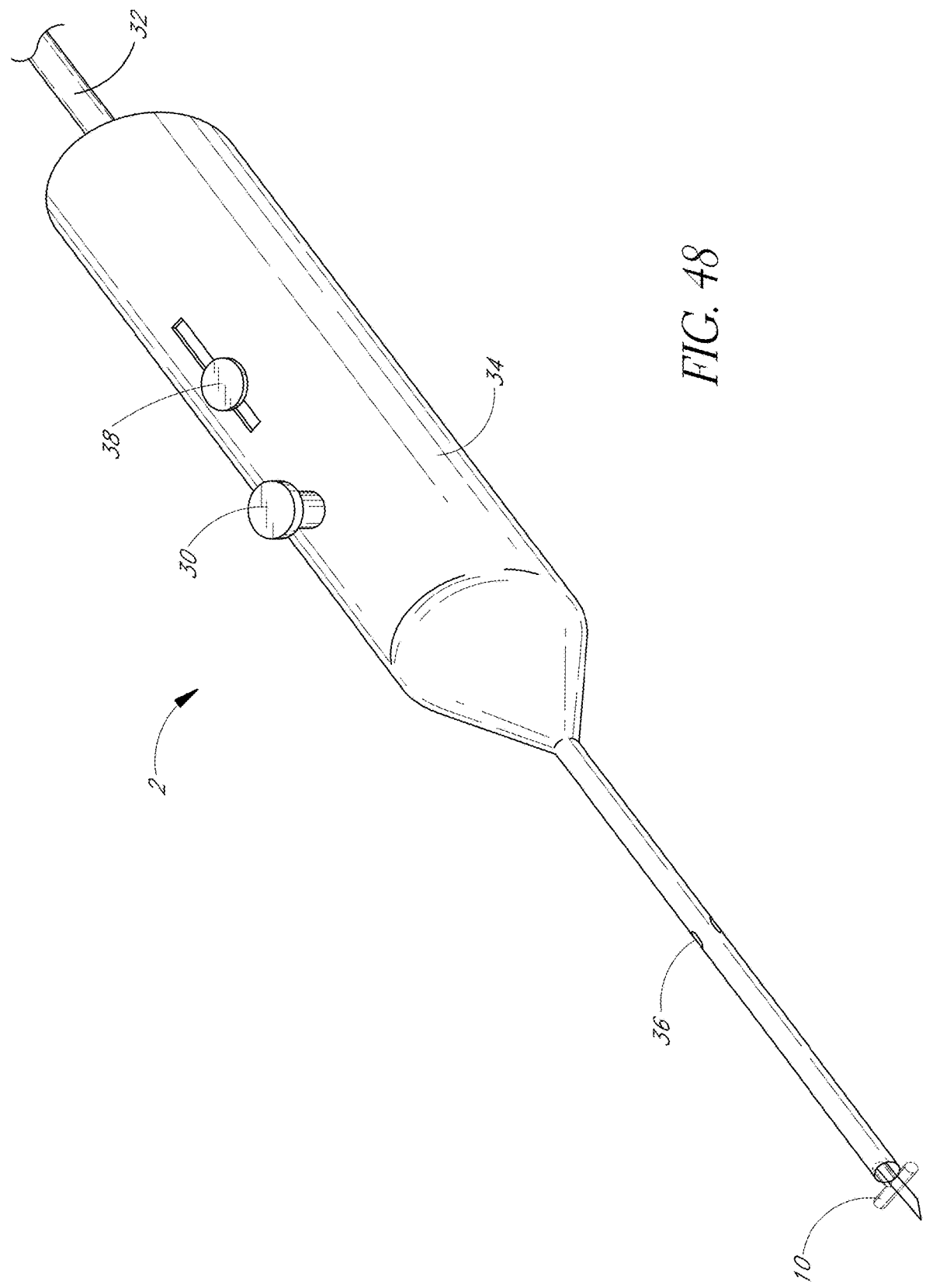
FIG. 48 is an oblique elevational view of a trabecular shunt applicator with a retractable blade mechanism.
Figure 49A:
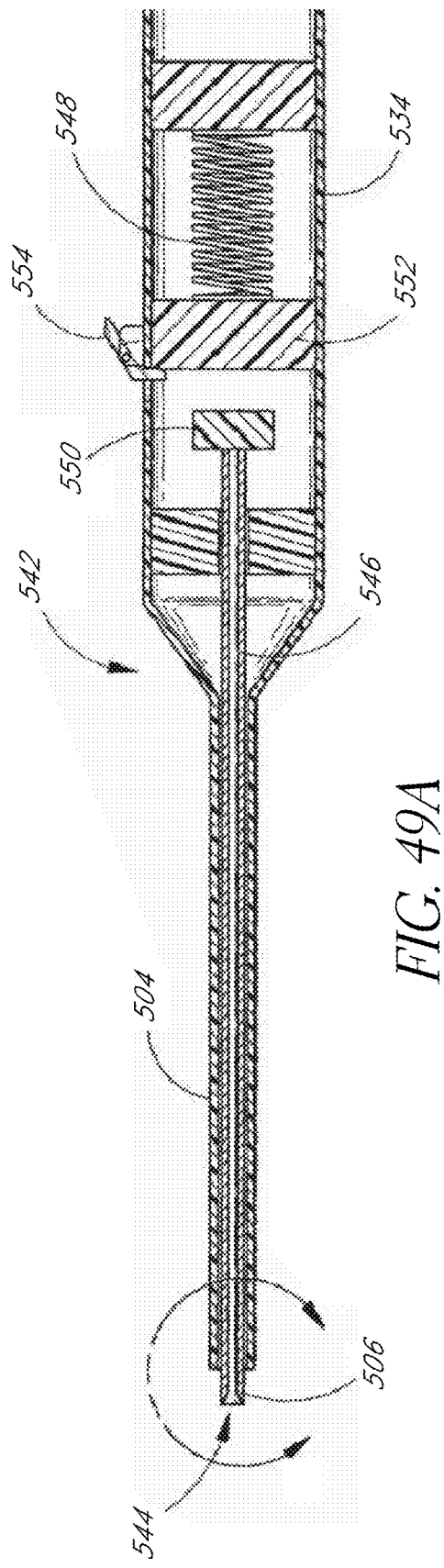
FIGS. 49A and 49B are schematic cross sections of a trabecular punch device.
Figure 49B:
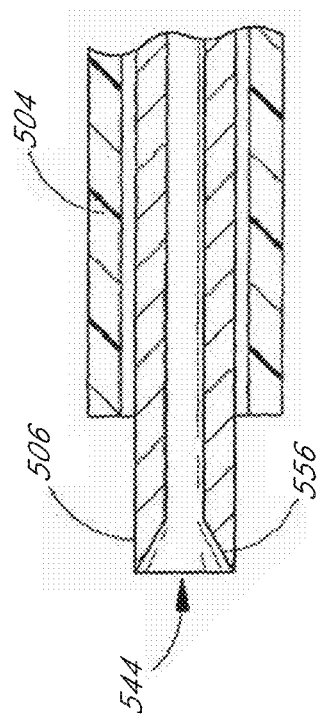
Figure 50A:
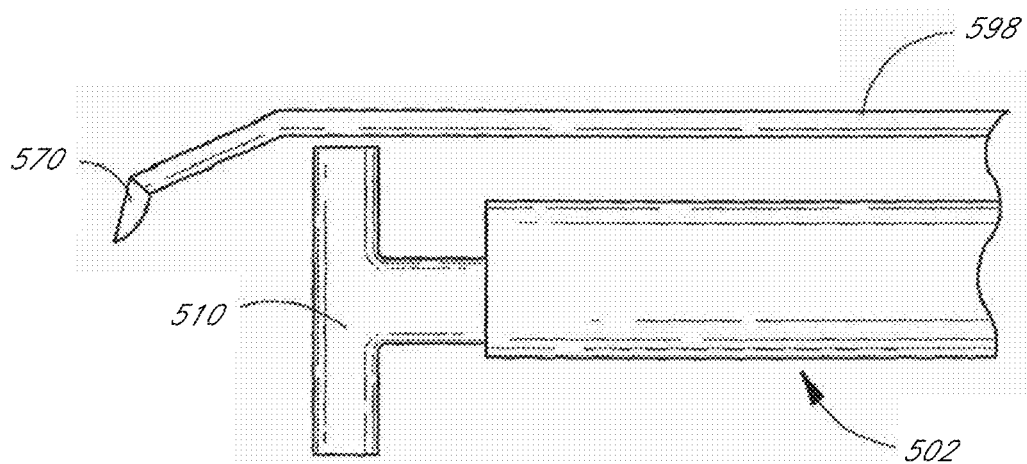
FIGS. 50A and 50B are elevational views of a control arm and trabeculotomy device for the trabecular shunt applicator.
Figure 50B:
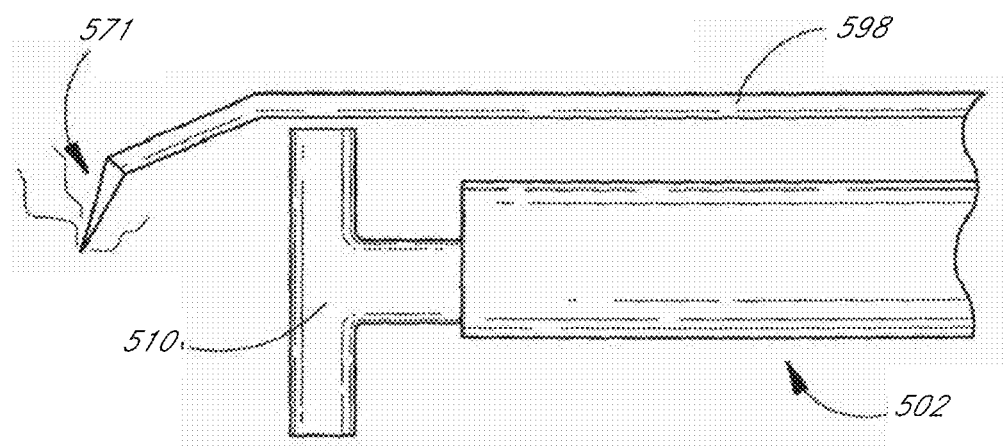
Figure 51A:
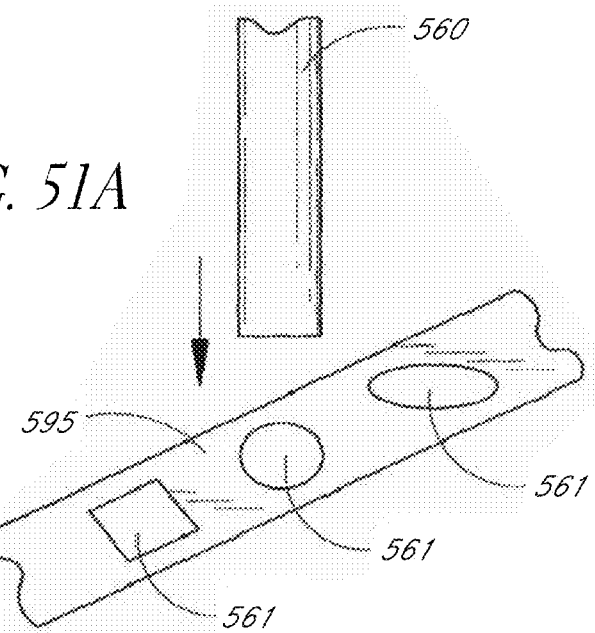
FIGS. 51A through 51C are schematic oblique elevational views of various trabecular meshwork punching and drilling devices.
Figure 51B:
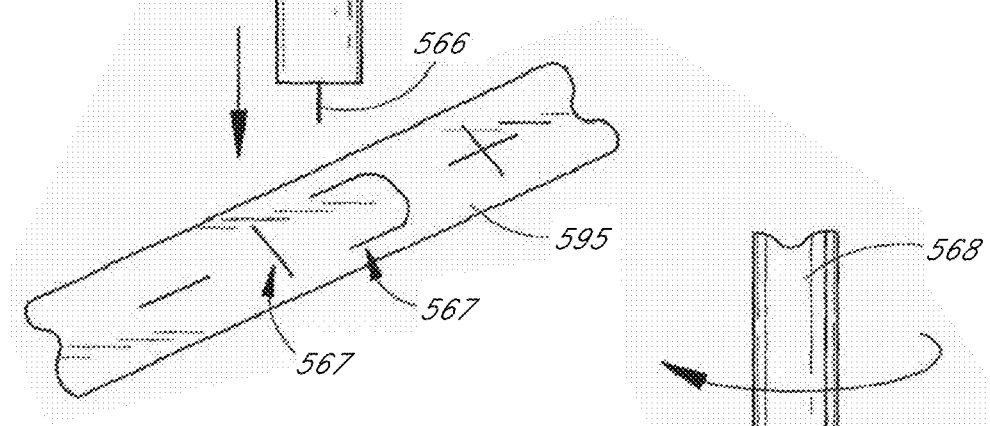
Figure 51C:
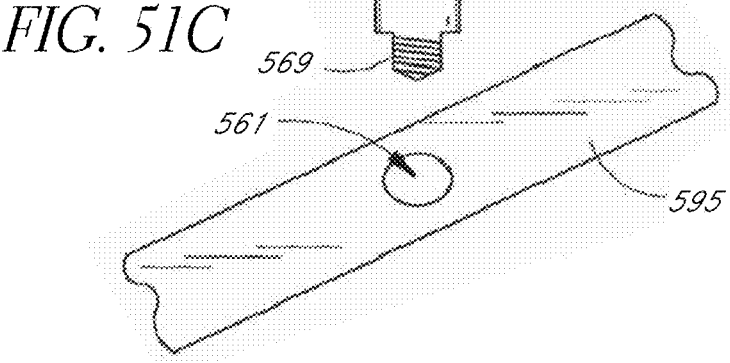

Targeted Drug Delivery to the Trabecular Meshwork:

FIG. 47 illustrates a targeted drug delivery implant 30v having features and advantages in accordance with one embodiment. This drawing is a depiction of a targeted drug delivery concept. The slow release implant 30v is implanted within the trabecular meshwork 21.

A drug that is designed to target the trabecular meshwork 21 to increase its porosity, or improve the active transport across the endothelial layer of Schlemm's canal 22 can be stored in this small implant 30v (FIG. 47). Advantageously, slow release of the drug promotes the desired physiology at minimal dosage levels since the drug is released into the very structure that it is designed to modify.

While the components and techniques of the invention have been described with a certain degree of particularity, it is manifest that many changes may be made in the specific designs, constructions and methodology herein above described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A system for treating an ocular disorder in a patient, the system comprising:
    a delivery device, said delivery device comprising a handpiece and an elongate delivery member; and
    a plurality of glaucoma stents, each of the plurality of glaucoma stents comprising:
        a head portion comprising an inlet port;
        a base portion, the base portion comprising at least one port and a tapered portion;
        a waist portion attached to the head portion at a first end and to the base portion at a second end, the waist portion having an external diameter less than that of both an external diameter of a largest part of the base portion and an external diameter of a largest part of the head portion; and
        a lumen at least partially passing through the head portion, base portion, and the waist portion, the lumen in communication with the at least one port,
        wherein the external diameter of the largest part of the head portion is greater than the external diameter of the largest part of the base portion.

2. The system of claim 1, wherein the external diameter of the largest part of the head portion is between 350 μm and 2500 μm.

3. The system of claim 1, wherein the elongate delivery member extends through at least a portion of the lumen.

4. The system of claim 1, wherein each of the stents is composed of titanium.

5. The system of claim 1, wherein a surface material of each of the stents comprises heparin.

6. The system of claim 1, wherein the handpiece of the delivery device further comprises an actuator configured to cause deployment of the plurality of stents from the delivery device.

7. The system of claim 1, wherein the stents are preloaded on the elongate delivery member.

8. A method of treating an ocular disorder in a patient, the method comprising:
    providing an anesthetic to an eye of the patient;
    forming a corneal incision in the eye of the patient;
    inserting an elongate delivery member of a delivery device through the corneal incision and advancing a distal tip of the elongate delivery member within an anterior chamber of the eye toward a desired implantation site,
    wherein the elongate delivery member comprises a plurality of glaucoma stents,
    wherein each of the plurality of glaucoma stents comprises a tapered base portion, an intermediate waist portion, and a head,
    wherein the tapered base portion comprises a plurality of outlet ports,
    wherein a minimum cross-sectional diameter of the head is greater than a maximum cross-sectional diameter of the tapered base portion; and
    causing a tapered base portion of a first glaucoma stent of the plurality of glaucoma stents to be delivered through trabecular meshwork and into a Schlemm's canal of the eye with the head of the first glaucoma stent remaining in the anterior chamber, thereby facilitating flow of aqueous through the first glaucoma stent from the anterior chamber to the Schlemm's canal.

9. The method of claim 8, further comprising withdrawing the delivery device from the eye.

10. The method of claim 8, wherein a depth of the waist portion is approximately equal to a thickness of the trabecular meshwork.

11. The method of claim 8, wherein the minimum cross-sectional diameter of the head is the same as a maximum cross-sectional diameter of the head such that the diameter of the head is uniform.

12. The method of claim 11, wherein the uniform diameter of the head is between 300 μm and 2750 μm.

13. A method of treating an ocular disorder in a patient, the method comprising:
    inserting an elongate delivery member of a delivery device through an incision in an eye and advancing a distal tip of the elongate delivery member within an anterior chamber of the eye toward a desired implantation site,
    wherein the elongate delivery member comprises a plurality of stents,
    wherein each of the plurality of stents comprises a tapered base portion, an intermediate waist portion, and a head,
    wherein the tapered base portion comprises a plurality of outlet ports,
    wherein a minimum cross-sectional diameter of the head is greater than a maximum cross-sectional diameter of the tapered base portion; and
    causing a tapered base portion of a first stent of the plurality of stents to be delivered through trabecular meshwork and into a Schlemm's canal of the eye with the head of the first stent remaining in the anterior chamber, thereby facilitating flow of aqueous through the first stent from the anterior chamber to the Schlemm's canal.

14. The method of claim 13, further comprising withdrawing the delivery device from the eye.

15. The method of claim 13, wherein a depth of the waist portion is approximately equal to a thickness of the trabecular meshwork.

16. The method of claim 13, wherein the minimum cross-sectional diameter of the head is the same as a maximum cross-sectional diameter of the head such that the diameter of the head is uniform.

17. The method of claim 16, wherein the uniform diameter of the head is between 300 μm and 2750 μm.

* * * * *